US008309604B2

(12) United States Patent
Dasseux et al.

(10) Patent No.: US 8,309,604 B2
(45) Date of Patent: Nov. 13, 2012

(54) CYCLOALKYL-HYDROXYL COMPOUNDS AND COMPOSITIONS FOR CHOLESTEROL MANAGEMENT AND RELATED USES

(75) Inventors: Jean-Louis Henri Dasseux, Brighton, MI (US); Carmen Daniela Oniciu, Ann Arbor, MI (US)

(73) Assignee: Esperion Therapeutics, Inc., Plymouth, MI (US)

( * ) Notice: Subject to any disclaimer, the term of this patent is extended or adjusted under 35 U.S.C. 154(b) by 0 days.

(21) Appl. No.: 13/414,855

(22) Filed: Mar. 8, 2012

(65) Prior Publication Data

US 2012/0172337 A1    Jul. 5, 2012

Related U.S. Application Data

(60) Continuation of application No. 13/270,297, filed on Oct. 11, 2011, now Pat. No. 8,153,690, which is a continuation of application No. 12/135,504, filed on Jun. 9, 2008, now Pat. No. 8,067,466, which is a continuation of application No. 11/426,380, filed on Jun. 26, 2006, now Pat. No. 7,405,226, which is a division of application No. 10/743,287, filed on Dec. 23, 2003, now Pat. No. 7,119,221.

(60) Provisional application No. 60/441,795, filed on Jan. 23, 2003.

(51) Int. Cl.
*A61K 31/194*  (2006.01)
*A61K 31/225*  (2006.01)

(52) U.S. Cl. ........................ 514/529; 514/557

(58) Field of Classification Search .................. 514/529, 514/557
See application file for complete search history.

(56) References Cited

U.S. PATENT DOCUMENTS

| | | | |
|---|---|---|---|
| 3,152,148 A | 10/1964 | Easterly et al. | |
| 3,441,605 A | 4/1969 | Blake et al. | |
| 3,773,946 A | 11/1973 | Creger | |
| 3,930,024 A | 12/1975 | Creger | |
| 4,287,200 A | 9/1981 | Kawamatsu et al. | |
| 4,584,321 A | 4/1986 | Manghisi et al. | |
| 4,613,593 A | 9/1986 | Yamatsu et al. | |
| 4,634,719 A | 1/1987 | Takaishi et al. | |
| 4,689,344 A | 8/1987 | Bar-Tana et al. | |
| 4,711,896 A | 12/1987 | Bar-Tana et al. | |
| 4,714,762 A | 12/1987 | Hoefle et al. | |
| 5,166,174 A | 11/1992 | Ueno et al. | |
| 5,225,439 A | 7/1993 | Ueno et al. | |
| 5,284,858 A | 2/1994 | Ueno et al. | |
| 5,380,709 A | 1/1995 | Ueno et al. | |
| 5,428,062 A | 6/1995 | Ueno et al. | |
| 5,502,198 A | 3/1996 | Picard et al. | |
| 5,504,073 A | 4/1996 | Horman | |
| 5,578,639 A | 11/1996 | Horman | |
| 5,633,287 A | 5/1997 | Lee et al. | |
| 5,648,387 A | 7/1997 | Bisgaier et al. | |
| 5,750,569 A | 5/1998 | Bisgaier et al. | |
| 5,756,344 A | 5/1998 | Onda et al. | |
| 5,756,544 A | 5/1998 | Bisgaier et al. | |
| 5,783,600 A | 7/1998 | Bisgaier et al. | |
| 5,834,596 A | 11/1998 | Ageland et al. | |
| 5,886,034 A | 3/1999 | Ueno et al. | |
| 5,968,963 A | 10/1999 | Horman | |
| 5,981,595 A | 11/1999 | Picard et al. | |
| 6,004,925 A | 12/1999 | Dasseux et al. | |
| 6,017,905 A | 1/2000 | Roark et al. | |
| 6,037,323 A | 3/2000 | Dasseux et al. | |
| 6,093,719 A | 7/2000 | Bocan | |
| 6,093,744 A | 7/2000 | Lee et al. | |
| 6,124,309 A | 9/2000 | Bocan | |
| 6,143,755 A | 11/2000 | Bocan | |
| 6,410,802 B1 | 6/2002 | Dasseux et al. | |
| 6,459,003 B1 | 10/2002 | Dasseux et al. | |
| 6,506,799 B1 | 1/2003 | Dasseux et al. | |
| 6,646,170 B2 | 11/2003 | Dasseux et al. | |
| 6,673,780 B2 | 1/2004 | Dasseux et al. | |
| 6,699,910 B2 | 3/2004 | Dasseux et al. | |
| 6,703,422 B2 | 3/2004 | Dasseux et al. | |
| 6,713,507 B2 | 3/2004 | Dasseux et al. | |
| 6,790,953 B2 | 9/2004 | Dasseux et al. | |
| 6,831,105 B2 | 12/2004 | Dasseux et al. | |

(Continued)

FOREIGN PATENT DOCUMENTS

| | | |
|---|---|---|
| EP | 0 284 108 | 8/1993 |
| FR | 1 545 224 A | 11/1968 |
| GB | 1196594 | 7/1970 |
| GB | 1196595 | 7/1970 |
| GB | 1196596 | 7/1970 |
| GB | 1196597 | 7/1970 |
| GB | 1196598 | 7/1970 |
| WO | WO 96/30328 | 10/1996 |
| WO | WO 98/30530 A | 7/1998 |
| WO | WO 99/00116 | 1/1999 |

OTHER PUBLICATIONS

Bicking, et al., "11,12-Secoprostaglandins. 1. Acylhydroxyalkanoic acids and related compounds", J. Med. Chem., 1977, pp. 35-43, vol. 20.

(Continued)

*Primary Examiner* — Taofiq A Solola
(74) *Attorney, Agent, or Firm* — Brinks Hofer Gilson & Lione

(57) ABSTRACT

The present invention relates to novel cycloalkyl-hydroxyl compounds, compositions comprising hydroxyl compounds, and methods useful for treating and preventing a variety of diseases and conditions such as, but not limited to aging, Alzheimer's Disease, cancer, cardiovascular disease, diabetic nephropathy, diabetic retinopathy, a disorder of glucose metabolism, dyslipidemia, dyslipoproteinemia, hypertension, impotence, inflammation, insulin resistance, lipid elimination in bile, obesity, oxysterol elimination in bile, pancreatitis, Parkinson's disease, a peroxisome proliferator activated receptor-associated disorder, phospholipid elimination in bile, renal disease, septicemia, Syndrome X, thrombotic disorder. Compounds and methods of the invention can also be used to modulate C reactive protein or enhance bile production in a patient. In certain embodiments, the compounds, compositions, and methods of the invention are useful in combination therapy with other therapeutics, such as hypocholesterolemic and hypoglycemic agents.

20 Claims, No Drawings

U.S. PATENT DOCUMENTS

| | | |
|---|---|---|
| 6,909,014 B2 | 6/2005 | Dasseux et al. |
| 7,119,221 B2 | 10/2006 | Dasseux et al. |
| 7,192,940 B2 | 3/2007 | Dasseux et al. |
| 7,304,093 B2 | 12/2007 | Dasseux et al. |
| 7,335,689 B2 | 2/2008 | Dasseux et al. |
| 7,335,799 B2 | 2/2008 | Dasseux et al. |
| 7,405,226 B2 | 7/2008 | Dasseux et al. |
| 7,576,130 B2 | 8/2009 | Dasseux et al. |
| 2005/0043278 A1 | 2/2005 | Dasseux et al. |
| 2005/0119333 A1 | 6/2005 | Dasseux et al. |
| 2005/0214887 A1 | 9/2005 | Emori et al. |
| 2007/0155704 A1 | 7/2007 | Dasseux et al. |
| 2007/0179120 A1 | 8/2007 | Dasseux et al. |
| 2009/0247489 A1 | 10/2009 | Dasseux et al. |

OTHER PUBLICATIONS

Nagano H., et al., "Stereoselectivitiy in the formation and radical reduction of cyclic bromoacetals, key intermediates for the synthesis of delta-hydroxy-and epilson-hydroxy-alpha-methylcarboxylic acid esters", Tetrahedron Letters, 2003, pp. 6867-6870, vol. 44, No. 36.
Bobrova, et al., abstract, J. Org. Chem., 1983, pp. 259-261, vol. 19.
Narasaka, et al., abstract, Bull. Chem. Soc., 1987, pp. 1457-1464, vol. 60, No. 4.
Rieke, et al., abstract, J. Org. Chem., 1996, pp. 2726-2730, vol. 61 No. 8.
Pechmann, abstract, Chem. Ber., 1904, p. 3819, vol. 37.
Lardelli, et al., abstract, Recl. Tray. Chim., 1967, pp. 481-503, vol. 86.
Crisan, abstract, Ann. Chim., 1956, pp. 436-459, vol. 13, No. 1.
Blatt, et al., "The reducing action of Grignard reagent and the synthesis of tertiary aliphatic carbinols", J. Org. Chem., 1932, pp. 1495-1499, vol. 54.
Brown, et al., "Hydroboration 67. Cyclic hydroboration of acyclic alpha, omega-dienes with 9-Borabicyclo '3.3.1 !nonane/borane-dimethyl sulfide", J. Org. Chem. pp. 1072-1078, vol. 49, No. 6, (1984).
Weber, et al., abstract, J. Med. Chem., 1992, pp. 3755-3773, vol. 35, No. 21.
Yamamoto, "Asymmetric synthesis of 5-and 6-membered lactones from cyclic substrates bearing a c2-chiral auziliary", J. Org. Chem., 1991, pp. 1112-1119, vol. 35, No. 21.
Ooit, et al., abstract, Angewandte Chemie., 2001, vol. 40, No. 19.
English, J. Am. Chem. Soc., 1941, p. 942, vol. 63.
Gleiter, et al., Synthesis of 5,510,10-tetramethyl-1-oxacyclotridecane-6,7,8,9-tetrone-on the mechanism of the Rubotom reaction, 1995, (9), pp. 1655-1661.
Gleiter, et al., Synthesis and properties of 4,4,9,9-tetramethyl-1-oxa-cycloundecane-5,6,7,8-tetrone and 9-tetramethyl-1-oxa-cyclotridecane-6,7,8,9-tetrone, 1996, 2(3), pp. 271-277.
Momenteau, et al., abstract, J. Chem. Soc. Perkin Trans. 1985, pp. 221-232.
Silverman, The Organic Chemistry of Drug Design and Drug Interaction, 1992, pp. 15-22.
Bohme, V. and Lener, W., 1955, Annalen der Chemle, 595;169-178 (English language abstract).
Xu, et al., 1989, "The retinoblastoma susceptibility gene product: a characteristic pattern in normal cells and abnormal expression in malignant cells", Onocogene 4: 807-812.
Ackerly, et al., 1995, "A novel approach to dual-acting thromboxane receptor antagonist/synthase inhibitors based on the link of 1.3-dioxane-thrombaxane receptor antagonists and -thromboxane synthase inhibitors", J. Med. Chem. 38:1608-1628.
Acton, et al., 1996, "Identification of scavenger receptor SR-B1 as high density lipoprotein receptor", Science. 271(5248):518-20.
Ahrens, et al., 1967, "A direct method for preparing pyridoxal and 4-pyridoxic acid (1)", J. Heterocyl. Chem. 4:625-26.
Alexander, K., et al., 1948, "4.4-Dichlorodibutyl ether and its derivatives from tetrahydrofuran", J. Am. Chem. Soc. 70:1839-42.
Badimon, et al., 1992, "Role of High density lipoproteins in the regression of atherosclerosis", Circulation 85 (Suppl);11186-94.

Bailey, et al., 1990, "Convenient general method for the preparation of primary alkeyllithiums by lithium-iodine exchange", J. Org. Chem. 55:5404-06.
Barrans, et al., 1996, "Pre-beta HDL; structure and metabolism", Biochim, Biophys. Acta. 1300(2):73-85.
Becker, et al., 1982, "Intramolecular photoaddition of terminal allenes to conjugated cyclohexenones", J. Org. Chem. 47:3297-3310.
Bernady, et al., 1979, "Prostaglandins and congeners. 20..sup.1,2 Synthesis of prostaglandins via conjugate addition of lithiummm trans-1-alkenyltrialkylatanate reagents. A novel regent for conjugate 1,4-additions", J. Org. Chem. 44:1438-47.
Bhanot, et al., 1977, "Synthetic studies on Tarpenoids.5.Syntheses of . gamma.—and delta.—Lactones from beta.-(2,7-Dimethyl-1,2-dihdroxycycloheptyl)propionic Acid", J. Org. Chem. 42:1623-1627.
Bisgaier, et al., 1998, "A novel compound that elevates high density lipoprotein and activates the peroxisome prolifarator activated receptor", J. Lipid Res. 39(1):17-30.
Bisgaier, et al., 1997, "Attenuation of plasma low density lipoprotein cholesterol by select 3-hydroxy-3-methylglutaryl coenzyme A reductase inhibitors in mice of low density lipoprotein receptors", J. Lipid Res. 38 (12):2502-2515.
Bongini, et al., 1979 "A simple and practical method for tetrahydropyranylation of alcohols and phenols", Synthesis 618-620.
Brown, et al., 1965, "Selective reductions. VII. Reaction of lithium trimethoxyluminohydride with selected organic compounds containing representative functional groups", J. Am. Chem. Soc. 87:5614-20.
Brown, et al., 1980, "Selective reductions. 26 Lithuim triethylborohydride as an exceptionally powerful and selective reducing agent in organic synthesis. Exploration of the reactions with selected organic compounds containing representative functional groups sup.1,2", J. Org. Chem 45:1-12.
Bruce, et al., 1998, "Plasma lipid transfer proteins, high-density lipoproteins, and reverse cholesterol transport", Annu Rev Nutr. 1998;18:297-330.
Campagna, et al., 1994, "Cyclic Amidine Analogues of Taurine and Homotaurine; Synthesis and Effects on Rat Skeletal Muscle", Farmaco, Ed. Sci 49:653-658.
Corothers, 1924, "Platinum oxide as a catalyst in the reduction of organic compounds. V. The preparation of primary alcohols by the catalytic hydrogenation of aldehydes.sup.1", J. Am. Chem. Soc. 46:1675-83.
Cerny, et al., 1969, "Properties of Sodium Bis-(2-Methoxyethoxy_ Aluminum Hydride", Collect Czech Chem Commn. 34:1025-33.
Chadwick, et al., 1979, "Reaction between N-Alkylpyroles and Alkylithium Reagents" J. Chem Soc., Perkin Trans. 12845.
Chaikin, et al., 1949, "Lithium Borohydride as a Reducing Agent", J. Am. Chem. Soc. 71:3245-48.
Chen, et al., 1998, "Asymetic total synthesis of phosphatidylinositol 3-phosphate and 4-phosphate derivatives", J. Org. Chem. 63:6511-22.
Comins, et al., 1981, "A one pot synthesis of unsymmetrical secondary alcohols from two grignard reagents", Tetrahadron Lett. 22:1085-88.
Corbridge, 1985, "Phosphorus: An Outline of its Chemistry, Biochemistry and Technology", Studies in Inorganic Chemistry, 3.sup. rd. ed, pp. 357-395.
Corey, et al., 1979, "Useful procedures for the oxidation of alcohols involving pyridinum dichromate in aprotic media", Tetrahadron Lett. 5:399-402.
Corey, et al., 1967, "A useful method for the conversion of alcohols into iodides", J. Org. Chem. 32:4160-4161.
Danheiser, et al., 1991, "A Practical and Efficient Method for Synthesis of .beta.-Lactones", J. Org. Chem. 58:1176-65.
Dansky HM, Fisher Ea, 1999, "High-density lipoprotein and plaque regression: the good cholesterol gets even better", Circulation 100(17): 1762-3.
Decossin, et al., 1997, "Subclasses of LpA-I in coronary artery disease: distribution and cholesterol efflux ability", Eur J Clin Invest. 27(4):299-307.
Desarlo, et al., 1971, "Isoxazolin-5-one", J. Chem Soc. 88-89.
Eaton, et al., 1972, "Hydroxypropylation", J. Org. Chem. 37:1947-50.

Ehlinger, et al., 1980, "Silicon in Synthesis. 10. The (trimethylsiyl)allyl Anion: A. .beta.-Acyl anion equivalent for the conversion of aldehydes and ketones into .lambda.-lactone", J. Am. Chem. Soc. 102:5004-11.

Fielding & Fielding, 1995, "Molecular physiology of reverse cholesterol transport", J. Lipid Res. 36(2):211-28.

Fraser, et al., 1985, "Acidity measurements in THF.V . . .sup. 1 Heteroaromatic compounds containing 5-membered rings", Can J. Chem. 63:3505-09.

Garegg, et al., 1980, "Novel Reagent System for converting a Hydroxy-group into an Iodo-group in carbohydrates with inversion of Configuration", J.C.S. Perkin I 2866-2868.

Gearing, et al., 1993, "Interaction of the peroxisome-proliferator-activated receptor and retinold X receptor", Proc. Natl. Acad. Sci. USA 90(4):14440-1444.

Gigg, et al., 1967, "The Prepartion of Unsymmetrical Diglycerides", J. Chem. Soc., C. 431-434.

Green and Kehinde, 1975, "An established predispose cell line and its differentiation in culture II. Factors affecting the adipose conversion", Cell. 5(1):19-27.

Gren, T.W., 1999, "Protection for the Hydroxyl Group, Including 1,2-and 1,3-Diols", Protective Groups in O.

Harris and Kletzien, 1994, "Localization of ploglitazone response element in the adipocyte fatty acid-binding protein gene", Mol Pharmacol. 45(3):439-45.

Hayden and Ma, 1992, "Molecular genetics of human lipoprotein lipase deficiency", Mol Cell Biochem. 113(2):171-6.

Heyman, et al., 1992, "9-cis retilnoic acid is high affinity ligand for the retinoid X receptor", Cell 68(2):397-406.

Hidaka and Fidge, 1992, "Affinity purification of the hepatic high-density lipoprotein receptor identifies two acidic glycoproteins and enables further characterization of their binding properties", Biochem. J. 15(Pt1):161-7.

Hirano, et al., 1997, "Genetic cholesteryl ester transfer deficiency is extremely frequent in the Omagari area of Japan. Marked hyperalphalipoproteinema caused by CETP gene mutation is not associated with longevity", Arterioscler. Thromb. Vasc. Biol. 17(6):1053-1059.

Hoyer, et al., 1986, "Catalysis by acidic clay of the protective tetrahydropyranylation of alcohols and phenols", Synthesis 655-57.

Hudlicky, M., 1996, "Reduction of esters and lactones of coraboxylic acids", Reduction in Organic Chemistry 2.sup.nd Ed. pp. 212-217.

Hudilicy, M., 1996, "Reduction of aldehydes and their derivatives", Reductions in Organic Chemistry, 2.sup. nd ed. pp. 137-139.

Ishibashi, et al., 1994, "Massive xanthomatosis and atherosclerosis in cholesterol-fed low density lipoprotein receptor-negative mice", J. Clin Invest. 93(5):1885-93.

Ishibashi, et al., 1993, "Hypercholesterolemia in low density lipoprotein receptor knockout mice and its reversal by adenovirus-mediated gene delivery", J. Clin. Invest. 92(2):883-93.

Isseman and Green, 1990, "Activation of a member of the steroid hormone receptor superfamily by peroxisome proliferators", Nature 347(6294):645-650.

Iwai, et al, 1966, "Studies on acelytenic compounds. XLIV..sup..1 Synthesis of 3-aminoisoxazoles and 3-hydroxyisoxazoles (2-Isoxazolones)", Chem. Pharm. Bull. 14:1277-88.

Johnston, et al., 1988, "A new, mild heterogeneous catalyst for the tetrahydropyranylation of alcohols andphelos", Synthesis 393-4.

Katritzky, et al., 1993, "Generation and Reactions of sp.sup.2-Carbanionic Centers in the Vicinity of Heterocyclic Nitrogen Atoms", Adv. Het. Chem. 56:155-303.

Keller and Wahli, 1993, "Peroxisome proliferator-activated receptors—A link between endocrinology and Nurition?" TEM, 4:291-295.

Keller, et al., 1993, "Fatty acids and retinolds control lipid metabolism through activation of peroxisome proliferator-activated receptor-ratinoid X receptor heterodimers", Proc. Natl. Acad. Sci. USA 90(6):2160-2164.

Kessar, et al., 1997, "Lewis acid complexion of tertiary animes and related compounds: A strategy for a alpha-deprotonation and stereocontrol", Chem. Rev. 97:721-37.

Kurz, et al., 1985, "Anomalous selectivities in methyl transfers to water: An explanation using free energy surfaces which model the effects of non-equilibrium solvation", Isr. J. Chem. 26:339-48.

Kletzein, et al., 1991, "Enhancement of adipocyte differentiation by an insulin-sensitizing agent", Mol Pharmacol 41(2):393-398.

Kliewer, et al., 1992, "Convergence of 9-cis retinoic acid and peroxisome proliferator signalling pathways through heterodimer formation of their receptors", Nature 27;358(6389):771-4.

Kurata, et al., 1998, "A candidate high density lipoprotein (HDL) receptor, HB2, with possible multiple functions shows sequence homology with adhesion molecules", J. Atherosclerosis and Thrombosis 4(3):112-7.

Kurz, et al., 1986, "Evidence for rate-determining salvation change in methyl transfer to water. Solvent dependence of $H_2O/D_2O$ kinetic isotope effects", J. Am. Chem 108:2960-68.

Lagrost, et al., 1996, "Opposite effects of cholesteryl ester transfer protein and phospholipid transfer protein on the size distribution of plasma high density lipoproteins. Physiological relevance in alcoholic patients", J. Biol. Chem. 271(32):19058-65.

Landshultz, et al., 1996, "Regulation of scavenger receptor, class B, type I, a high density lipoprotein receptor, in liver and steroidogenic tissues of the rat", J. Clin. Invest. 98(4):984-995.

Larock, 1989, Comprehensive Organic Transformations; Ch. 6, VCH: New York, pp. 446-448.

Lazarow and Fujiki, 1985, "Biogenesis of peroxisomes", Annu Rev Cell Biol. 1:489-530.

Levin, et al., 1992, "9-cis retinoic acid stereoisomer binds and activates the nuclear receptor RXR alpha", nature 355(6358):359-61.

Ludwig, et al., 1989, "Rapid and efficient synthesis of nucleoside 5'-0-(1-thiotriphosphates), 5'-triphosphates and 2',3'-Cyclophosphorothioates using 2-Chloro-4H-1,3,2-benzodioxaphosphorin-4-one", J. Org. Chem. 54:631-35.

Maddaford, et al., 1993, "A general asymmetric synthesis of (−)-alpha-Dimethyretrodendrin and its diastereomers", J. Org. Chem 58:4132-38.

March, J., 1992, Advanced Organic Chemistry; reactions Mechanisms, and Structure 4.sup.th ed., pp. 248-272, 1196-98, 437-438, 920-929.

Masamune, et al., 1976, "Tylonolide hemiacetal, the aglycone of tylosin, and its partial synthesis [letter]". J Am Chem Soc. 98(24):7874-5.

Masayuma, et al., 2000, "Regio-and diastereocontrol in carbonyl allylation by 1-halobut-2-enes with Tin(II) halides", J Org Chem. 65(2):494-8.

Menger, et al., 1981, "Synthetically useful oxidations at solid sodium permanganate surfaces", Tetrahedron Lett. 22:1655-56.

Miyashita, et al., 1977, "Pyridinium .rho.-Toluenesulfonate. A mild and efficient catalyst for the tetrahydropyranylation of alcohols", J. Org. Chem 42:3772-74.

Moffet, et al., 1963, "2-(1-Pyrrolidyl)Propanol", Org. Synth. Collect 4:834-5.

Myers, et al., 1992, "Studies on the thermal generation and reactivity of a class of (.alpha., .pi.)-1,4-biradicals", J. Am. Chem. Soc. 114:9369-86.

Nemali, et al., 1988, "Comparison of constitutive and Inducible levels of expression of paroxisomal beta-oxidation and catalase genes in liver and extrahepatic tissues of rat", Cancer Res. 48(18):5316-24.

Nystrom, et al., 1947, "Reduction of Organic Compounds by Lithium Aluminum Hyride", J. Am. Chem. Soc. 69:1197-1199.

Nystrom, et al., 1949, "Lithium borohydride as a reducing agent", J. Am. Chem. 71:3245-47.

Ogata, et al., 1969, "Kinetics of the Baeyer-Villiger reaction of benzaldehydes with perbenzoic acid in aquoorganic solvents", J. Org. Chem. 34:3985-91.

Okamoto, et al., 1985, "Synthesis of Alkyl Dihydrogenphosphate by the Reaction of Alcohols and Silyl Polyphosphate", Bull Chem. Soc. Jpn. 58:3393-3394.

Olah, et al., 1984, "N-Fomylmorpholine: A New and Effective Formylating Agent for the Preparation of Aldehydes and Dialkyl(1-Formylalkyl)phosphonates from Grignard or Organolithium Reagents", J. Org. Chem. 4.

Olah, et al., 1987, "Formylating Agents", Chem. Rec. 87:4, 671-686.

Olah, et al., 1979, "Transformations with Chlorotrimethylsilane/Sodium Iodide, a Convenient in Situ Ioditrimathylsilane Reagent", J. Org. Chem 44:8, 1247-1251.

Oster, et al., 1983, "Generation and Reactions of the Dianion of 3-Hydroxy-5-methylisoxazole, a convenient .beta.-keto Amide Synthon", J. Org. Chem 48:4307-4311.

Parra, et al., 1992, "A case-control study of lipoprotein particles in two populations at contrasting risk for coronary heart disease. The ECTIM Study", Arterioscler Thromb. 12:701-707.

Pop, et al., 1997, "Allylic and Phenolic Phosphate Esters of Dexanabinol", Org. Prep. and Proc. Int. 29:341-347.

Ramirez, et al., 1978, "Phosphorylation by means of cyclic enediol phosphates.sup.1", Acc. Chem. Res. 11:239.

Raunio, et al., 1957, "Addition of Propargyl Acetal to Cyclohexanone in the Presence of Sodamide", J. Org. Chem 22:570.

Reaven, 1993, "Role of Insulin resistance in human disease (syndrome X): an expanded definition", Annu Rev Med. 44:121-31.

Reddy and Lalwani, 1983, "Carcinogenesis by hepatic paroxisome proliferators: evaluation of the risk of hypolipidemic drugs and industrial plasticizers to humans", Crit Rev Toxicol. 12(1):1-58.

Rigotti, et al., 1996, Regulation by adrenocorticotropic hormone of the in vivo expression of scavenger receptor class B type I (SR-BI), a high density lipoprotein receptor, in steroidogenic cells of the murine adrenal.

Robins and Fasulo, 1997, "High density lipoproteins, but not other lipoproteins, provide a vehicle for sterol transport to bile", J Cln Invest. 98(3):380-4.

Sam, et al., 1972, "Crown Polyether Chemistry, Postassium Permanganate Oxidations in Benzene", J. Am. Chem. Soc. 94:4024.

Saulnier, et al., 1982, "Generation and Reactions of 3-Lithio-1-(phenylsulfonyl)Indole", J. Org. Chem 47:757.

Shirley, et al., 1995, "Metalation of pyrrole, 1-methylpyrrole, and 1-phenylpyrrola with n-Butyllithium", J. Org. Chem 20:225-31.

Sianesi, et al., 1971, "2.4-dihydro-1H-2.1-, 3.4-Dihydro-2H-1.2-und. 3.4-Dihydro-1H-2.3-benzothiazin-S.S-dioxid", Chem. Ber. 104:1880-91.

Skinner, et al., 1995, "Benzoylcyanamide from ethyl benzoylitioncarbomate", J. Am. Chem. Soc. 77:5440-42.

Smith, et al., 1957, "Nitrogen Compounds of the phosphoric and Phosphonic Acids, III, Preparation and Properties of Amides of Phenylphosphonic and Phenylphosphonothiolic Acids", J. Org. Chem. 22:265-267.

Song, et al., 1999, "Practical asymatic synthesis of an endothelin receptor antagonist", J. Org. Chem. 64:9658-67.

Staels and Auwerx, 1998, "Regulation of apo A-I gene expression by fibrates", Atherosclerosis 137 Suppl:S19-23.

Stevens, et al., 1982, "Further studies on the utility of sodium hypochlrite in organic synthesis. Selective oxidation of diols and direct conversion of aldehydes to esters", Tetrahedon Lett. 23:4647-4650.

Stowell, et al., 1995, "A new method for the phosphorylation of alcohols and phenols", Tetrahedron Lett. 36(11):1825-26.

Sundararaman, et al., 1978, "One step conversion of aldehydas to esters", Tetrahedron Lett. 19:1627-1628.

Tomroka, et al., 1995, "Catalytic Asymmetric Conjugate Addition of Grignard Reagents Mediated by Copper (I)-Chiral Bedentate Phosphine Complex", Tetrahedron Lett. 36:4275-4278.

Tontonoz, et al., 1994, "Adipocyte-specific transcription factor ARF6 is a heterodimeric complex of two nuclear hormone receptors, PPAR gamma and RXR alpha", Nucleic Acids Res. 22(5):5628-34.

Uhlmann, et al., 1986, "Chemical 5'-phosphorylation of oligonucleotides valuable in automated dna synthesis", Tetrahedron Lett. 27:1023-26.

Ulrich, et al., 1995, "Cultured hepatocytes as investigational models for heptic toxicity: practical applications in drug discovery and development", Toxicol Lett. 82/83:107-15.

Urata, et al., 1991, "Transition metal complex catalyzed carbonylation od organic halides in the presence of molecular sieves instead of base", tetrahedron Lett. 32:36, 4733-36.

Vogtle, et al., 1987, "Doubly Clamped Cope Systems", J. Org. Chem. 52:5560-5564.

Blatt ed., 1943, "Gilbert Sulfonation and Related Reactions" pp. 135-142, 160-165; Org. Synth. Coll. vol. II, Wiley, NY and Org. Synth. Coll. vol. IV, 1963, Wiley NY 529-531.

Williams, et al., 1988, "Bromine as an oxidant for direct conversion of aldehydes to esters", Tetrahedron Lett. 29:5087-90.

Wilson, et al., 1982, "A novel, nonoxidative method for the conversion of aldehydes to esters", J. Org. Chem. 47:1360-61.

Wroblewski and Ladue, 1995, "Lactic dehydrogenase activity in blood", Proc. Soc. Exp. Biol. Med. 90:210-213.

Yanagisawa, et al., 1994, "Allylbarium Reagents: Unprecedented regio- and stereoselectiv eallylation reactions of carbonyl compounds", J. Am. Chem. Soc. 116:6130-6141.

Yoshikawa, et al., 1986, "Ruthenium Complex Catalyzed Regioselective Dehydrogenation of Unsymmetrical alpha. Omega.-Diols", J. Org. Chem. 51:2034.

Yoshikawa, et al., 1983, "Catalytic Regioselective Dehydrogenation of Unsymmetrical .alpha., .Omega.-Diols Using Ruthenium Complexes", Tetrahedron Lell 26:2677-2680.

Yu, et al., 1988, "A novel reagent for the synthesis of myo-inositol phasphates: n, n-diisopropyl dibenzyl phosphoramidite", Tetrahedron Lett. 29:979-82.

Nan F, et al., "Dual Function Glutamata-Related Ligands: Discovery of a Novel, Potent Inhibitor of Glutamate Carboxypeptidase II Possessing mGluR3 Agonist Activity" Journal of Medicinal Chemistry 2000, 43:pp. 772-774.

Yunker, et al., 1978, "Alpha-oxygenated fatty acids occurring as amides of 2-methylene .beta.-alanine in a marina sponge", Tetrahedron Lett. 47:4651-52.

Taravel, et al., 1988, "Interglycosidic .sup. 13 C-sup.1 H Coupling Constants", Tetrahedron Lett. 29:199-200.

Vamecq and Draye, 1989, "Pathophysiology of peroxisomal beta-oxidation", Essays Biochem 24:115-225.

Mulzer, 1995, Comprehensive Organic Functional Group Tranformations Oxford 5 pp. 161.

Sweeney, 1995, "Comprehensive Organic Functional Group Transformations", Oxford, vol. 2, pp. 104-109.

Eisch, et al. 1978, "Synthesis of lactones via the titanium-catalyzed hydromagnesiation of alkenols", J. Organo. Mel. Chem. 160:C8-C12.

CYCLOALKYL-HYDROXYL COMPOUNDS AND COMPOSITIONS FOR CHOLESTEROL MANAGEMENT AND RELATED USES

CROSS REFERENCE TO RELATED APPLICATIONS

This application is a continuation of U.S. Ser. No. 13/270,297, filed Oct. 11, 2011, now allowed; which is a continuation of U.S. Ser. No. 12/135,504, filed Jun. 9, 2008, now U.S. Pat. No. 8,067,466; which is a continuation of U.S. Ser. No. 11/426,380, filed Jun. 26, 2006, now U.S. Pat. No. 7,405,226; which is a division of U.S. Ser. No. 10/743,287, filed Dec. 23, 2003, now U.S. Pat. No. 7,119,221; which claims benefit of U.S. Provisional Ser. No. 60/441,795, filed Jan. 23, 2003; all of which are incorporated herein by reference in their entirety.

1. FIELD OF THE INVENTION

The invention relates to cycloalkyl-hydroxyl compounds and pharmaceutically acceptable salts, hydrates, solvates, and mixtures thereof; compositions comprising a hydroxyl compound or a pharmaceutically acceptable salt, hydrate, solvate, or mixtures thereof; and methods for treating or preventing a disease or disorder such as, but not limited to, aging, Alzheimer's Disease, cancer, cardiovascular disease, diabetic nephropathy, diabetic retinopathy, a disorder of glucose metabolism, dyslipidemia, dyslipoproteinemia, enhancing bile production, enhancing reverse lipid transport, hypertension, impotence, inflammation, insulin resistance, lipid elimination in bile, modulating C reactive protein, obesity, oxysterol elimination in bile, pancreatitis, Parkinson's disease, a peroxisome proliferator activated receptor-associated disorder, phospholipid elimination in bile, renal disease, septicemia, metabolic syndrome disorders (e.g., Syndrome X), and a thrombotic disorder, which method comprise administering a hydroxyl compound or composition of the invention. The compounds of the invention can also treat or prevent inflammatory processes and diseases like gastrointestinal disease, irritable bowel syndrome (IBS), inflammatory bowel disease (e.g., Crohn's Disease, ulcerative colitis), arthritis (e.g., rheumatoid arthritis, osteoarthritis), autoimmune disease (e.g., systemic lupus erythematosus), scleroderma, ankylosing spondylitis, gout and pseudogout, muscle pain: polymyositis/polymyalgia rheumatica/fibrositis; infection and arthritis, juvenile rheumatoid arthritis, tendonitis, bursitis and other soft tissue rheumatism.

2. BACKGROUND OF THE INVENTION

Obesity, hyperlipidemia, and diabetes have been shown to play a causal role in atherosclerotic cardiovascular diseases, which currently account for a considerable proportion of morbidity in Western society. Further, one human disease, termed "Syndrome X" or "Metabolic Syndrome", is manifested by defective glucose metabolism (insulin resistance), elevated blood pressure (hypertension), and a blood lipid imbalance (dyslipidemia). See e.g. Reaven, 1993, *Annu. Rev. Med.* 44:121-131.

The evidence linking elevated serum cholesterol to coronary heart disease is overwhelming. Circulating cholesterol is carried by plasma lipoproteins, which are particles of complex lipid and protein composition that transport lipids in the blood. Low density lipoprotein (LDL) and high density lipoprotein (HDL) are the major cholesterol-carrier proteins. LDL is believed to be responsible for the delivery of cholesterol from the liver, where it is synthesized or obtained from dietary sources, to extrahepatic tissues in the body. The term "reverse cholesterol transport" describes the transport of cholesterol from extrahepatic tissues to the liver, where it is catabolized and eliminated. It is believed that plasma HDL particles play a major role in the reverse transport process, acting as scavengers of tissue cholesterol. HDL is also responsible for the removal of non-cholesterol lipid, oxidized cholesterol and other oxidized products from the bloodstream.

Atherosclerosis, for example, is a slowly progressive disease characterized by the accumulation of cholesterol within the arterial wall. Compelling evidence supports the belief that lipids deposited in atherosclerotic lesions are derived primarily from plasma apolipoprotein B (apo B)-containing lipoproteins, which include chylomicrons, very low density lipoproteins (VLDL), intermediate-density lipoproteins (IDL), and LDL. The apo B-containing lipoprotein, and in particular LDL, has popularly become known as the "bad" cholesterol. In contrast, HDL serum levels correlate inversely with coronary heart disease. Indeed, high serum levels of HDL are regarded as a negative risk factor. It is hypothesized that high levels of plasma HDL are not only protective against coronary artery disease, but may actually induce regression of atherosclerotic plaque (e.g., see Badimon et al., 1992, Circulation 86:(Suppl. 111)86-94; Dansky and Fisher, 1999, Circulation 100:1762 3). Thus, HDL has popularly become known as the "good" cholesterol.

2.1 Cholesterol Transport

The fat-transport system can be divided into two pathways: an exogenous one for cholesterol and triglycerides absorbed from the intestine and an endogenous one for cholesterol and triglycerides entering the bloodstream from the liver and other non-hepatic tissue.

In the exogenous pathway, dietary fats are packaged into lipoprotein particles called chylomicrons, which enter the bloodstream and deliver their triglycerides to adipose tissue for storage and to muscle for oxidation to supply energy. The remnant of the chylomicron, which contains cholesteryl esters, is removed from the circulation by a specific receptor found only on liver cells. This cholesterol then becomes available again for cellular metabolism or for recycling to extrahepatic tissues as plasma lipoproteins.

In the endogenous pathway, the liver secretes a large, very-low-density lipoprotein particle (VLDL) into the bloodstream. The core of VLDL consists mostly of triglycerides synthesized in the liver, with a smaller amount of cholesteryl esters either synthesized in the liver or recycled from chylomicrons. Two predominant proteins are displayed on the surface of VLDL, apolipoprotein B-100 (apo B-100) and apolipoprotein E (apo E), although other apolipoproteins are present, such as apolipoprotein CIII (apo CIII) and apolipoprotein CII (apo CII). When VLDL reaches the capillaries of adipose tissue or of muscle, its triglyceride is extracted. This results in the formation of a new kind of particle called intermediate-density lipoprotein (IDL) or VLDL remnant, decreased in size and enriched in cholesteryl esters relative to a VLDL, but retaining its two apoproteins.

In human beings, about half of the IDL particles are removed from the circulation quickly, generally within two to six hours of their formation. This is because IDL particles bind tightly to liver cells, which extract IDL cholesterol to make new VLDL and bile acids. The IDL not taken up by the liver is catabolized by the hepatic lipase, an enzyme bound to the proteoglycan on liver cells. Apo E dissociates from IDL as it is transformed to LDL. Apo B-100 is the sole protein of LDL.

Primarily, the liver takes up and degrades circulating cholesterol to bile acids, which are the end products of cholesterol metabolism. The uptake of cholesterol-containing particles is mediated by LDL receptors, which are present in high concentrations on hepatocytes. The LDL receptor binds both apo E and apo B-100 and is responsible for binding and removing both IDL and LDL from the circulation. In addition, remnant receptors are responsible for clearing chylomicrons and VLDL remnants (i.e., IDL). However, the affinity of apo E for the LDL receptor is greater than that of apo B-100. As a result, the LDL particles have a much longer circulating life span than IDL particles; LDL circulates for an average of two and a half days before binding to the LDL receptors in the liver and other tissues. High serum levels of LDL, the "bad" cholesterol, are positively associated with coronary heart disease. For example, in atherosclerosis, cholesterol derived from circulating LDL accumulates in the walls of arteries. This accumulation forms bulky plaques that inhibit the flow of blood until a clot eventually forms, obstructing an artery and causing a heart attack or stroke.

Ultimately, the amount of intracellular cholesterol liberated from the LDL controls cellular cholesterol metabolism. The accumulation of cellular cholesterol derived from VLDL and LDL controls three processes. First, it reduces the ability of the cell to make its own cholesterol by turning off the synthesis of HMGCoA reductase, a key enzyme in the cholesterol biosynthetic pathway. Second, the incoming LDL-derived cholesterol promotes storage of cholesterol by the action of cholesterol acyltransferase ("ACAT"), the cellular enzyme that converts cholesterol into cholesteryl esters that are deposited in storage droplets. Third, the accumulation of cholesterol within the cell drives a feedback mechanism that inhibits cellular synthesis of new LDL receptors. Cells, therefore, adjust their complement of LDL receptors so that enough cholesterol is brought in to meet their metabolic needs, without overloading (for a review, see Brown & Goldstein, in *The Pharmacological Basis Of Therapeutics*, 8th Ed., Goodman & Gilman, Pergamon Press, New York, 1990, Ch. 36, pp. 874-896).

High levels of apo B-containing lipoproteins can be trapped in the subendothelial space of an artery and undergo oxidation. The oxidized lipoprotein is recognized by scavenger receptors on macrophages. Binding of oxidized lipoprotein to the scavenger receptors can enrich the macrophages with cholesterol and cholesteryl esters independently of the LDL receptor. Macrophages can also produce cholesteryl esters by the action of ACAT. LDL can also be complexed to a high molecular weight glycoprotein called apolipoprotein (a), also known as apo(a), through a disulfide bridge. The LDL-apo(a) complex is known as Lipoprotein(a) or Lp(a). Elevated levels of Lp(a) are detrimental, having been associated with atherosclerosis, coronary heart disease, myocardial infarction, stroke, cerebral infarction, and restenosis following angioplasty.

2.2 Reverse Cholesterol Transport

Peripheral (non-hepatic) cells predominantly obtain their cholesterol from a combination of local synthesis and uptake of preformed sterol from VLDL and LDL. Cells expressing scavenger receptors, such as macrophages and smooth muscle cells, can also obtain cholesterol from oxidized apo B-containing lipoproteins. In contrast, reverse cholesterol transport (RCT) is the pathway by which peripheral cell cholesterol can be returned to the liver for recycling to extrahepatic tissues, hepatic storage, or excretion into the intestine in bile. The RCT pathway represents the only means of eliminating cholesterol from most extrahepatic tissues and is crucial to the maintenance of the structure and function of most cells in the body.

The enzyme in blood involved in the RCT pathway, lecithin:cholesterol acyltransferase (LCAT), converts cell-derived cholesterol to cholesteryl esters, which are sequestered in HDL destined for removal. LCAT is produced mainly in the liver and circulates in plasma associated with the HDL fraction. Cholesterol ester transfer protein (CETP) and another lipid transfer protein, phospholipid transfer protein (PLTP), contribute to further remodeling the circulating HDL population (see for example Bruce et al., 1998, *Annu. Rev. Nutr.* 18:297 330). PLTP supplies lecithin to HDL, and CETP can move cholesteryl esters made by LCAT to other lipoproteins, particularly apoB-containing lipoproteins, such as VLDL. HDL triglycerides can be catabolized by the extracellular hepatic triglyceride lipase, and lipoprotein cholesterol is removed by the liver via several mechanisms.

Each HDL particle contains at least one molecule, and usually two to four molecules, of apolipoprotein A I (apo A I). Apo A I is synthesized by the liver and small intestine as preproapolipoprotein, which is secreted as a proprotein that is rapidly cleaved to generate a mature polypeptide having 243 amino acid residues. Apo A I consists mainly of a 22 amino acid repeating segment, spaced with helix-breaking proline residues. Apo A I forms three types of stable structures with lipids: small, lipid-poor complexes referred to as pre-beta-1 HDL; flattened discoidal particles, referred to as pre-beta-2 HDL, which contain only polar lipids (e.g., phospholipid and cholesterol); and spherical particles containing both polar and nonpolar lipids, referred to as spherical or mature HDL (HDL3 and HDL2). Most HDL in the circulating population contains both apo A I and apo A II, a second major HDL protein. This apo A I- and apo A II-containing fraction is referred to herein as the AI/AII-HDL fraction of HDL. But the fraction of HDL containing only apo A I, referred to herein as the AI HDL fraction, appears to be more effective in RCT. Certain epidemiologic studies support the hypothesis that the AI-HDL fraction is antiartherogenic (Parra et al., 1992, *Arterioscler. Thromb.* 12:701-707; Decossin et al., 1997, *Eur. I Clin. Invest.* 27:299-307).

Although the mechanism for cholesterol transfer from the cell surface is unknown, it is believed that the lipid-poor complex, pre-beta-1 HDL, is the preferred acceptor for cholesterol transferred from peripheral tissue involved in RCT. Cholesterol newly transferred to pre-beta-1 HDL from the cell surface rapidly appears in the discoidal pre-beta-2 HDL. PLTP may increase the rate of disc formation (Lagrost et al., 1996, *J. Biol. Chem.* 271:19058-19065), but data indicating a role for PLTP in RCT is lacking. LCAT reacts preferentially with discoidal and spherical HDL, transferring the 2-acyl group of lecithin or phosphatidylethanolamine to the free hydroxyl residue of fatty alcohols, particularly cholesterol, to generate cholesteryl esters (retained in the HDL) and lysolecithin. The LCAT reaction requires an apolipoprotein such as apo A I or apo A-N as an activator. ApoA-I is one of the natural cofactors for LCAT. The conversion of cholesterol to its HDL-sequestered ester prevents re-entry of cholesterol into the cell, resulting in the ultimate removal of cellular cholesterol. Cholesteryl esters in the mature HDL particles of the AI-HDL fraction are removed by the liver and processed into bile more effectively than those derived from the AI/AII-HDL fraction. This may be due, in part, to the more effective binding of AI-HDL to the hepatocyte membrane. Several HDL receptors have been identified, the most well characterized of which is the scavenger receptor class B, type I (SR BI) (Acton et al., 1996, *Science* 271:518-520). The SR-BI is expressed most abundantly in steroidogenic tissues (e.g., the adrenals), and in the liver (Landshulz et al., 1996, *J. Clin. Invest.* 98:984-995; Rigotti et al., 1996, *J. Biol. Chem.* 271: 33545-33549). Other proposed HDL receptors include HB1 and HB2 (Hidaka and Fidge, 1992, *Biochem J.* 15:161 7; Kurata et al., 1998, *J. Atherosclerosis and Thrombosis* 4:112 7).

While there is a consensus that CETP is involved in the metabolism of VLDL- and LDL-derived lipids, its role in RCT remains controversial. However, changes in CETP activity or its acceptors, VLDL and LDL, play a role in "remodeling" the HDL population. For example, in the absence of CETP, the HDL becomes enlarged particles that are poorly removed from the circulation (for reviews on RCT and HDL, See Fielding & Fielding, 1995, *J. Lipid Res.* 36:211-228; Barrans et al., 1996, *Biochem. Biophys. Acta.* 1300:73-85; Hirano et al., 1997, *Arterioscler. Thromb. Vasc. Biol.* 17:1053-1059).

2.3 Reverse Transport of Other Lipids

HDL is not only involved in the reverse transport of cholesterol, but also plays a role in the reverse transport of other lipids, i.e., the transport of lipids from cells, organs, and tissues to the liver for catabolism and excretion. Such lipids include sphingomyelin, oxidized lipids, and lysophophatidylcholine. For example, Robins and Fasulo (1997, *J. Clin. Invest.* 99:380 384) have shown that HDL stimulates the transport of plant sterol by the liver into bile secretions.

2.4 Peroxisome Proliferator Activated Receptor Pathway

Peroxisome proliferators are a structurally diverse group of compounds that, when administered to rodents, elicit dramatic increases in the size and number of hepatic and renal peroxisomes, as well as concomitant increases in the capacity of peroxisomes to metabolize fatty acids via increased expression of the enzymes required for the β-oxidation cycle (Lazarow and Fujiki, 1985, *Ann. Rev. Cell Biol.* 1:489 530; Vamecq and Draye, 1989, *Essays Biochem.* 24:1115 225; and Nelali et al., 1988, *Cancer Res.* 48:5316 5324). Chemicals included in this group are the fibrate class of hypolipidemic drugs, herbicides, and phthalate plasticizers (Reddy and Lalwani, 1983, *Crit. Rev. Toxicol.* 12:1 58). Peroxisome proliferation can also be elicited by dietary or physiological factors, such as a high fat diet and cold acclimatization.

Insight into the mechanism whereby peroxisome proliferators exert their pleiotropic effects was provided by the identification of a member of the nuclear hormone receptor superfamily activated by these chemicals (Isseman and Green, 1990, *Nature* 347:645 650). This receptor, termed peroxisome proliferator activated receptor a (PPARα), was subsequently shown to be activated by a variety of medium and long chain fatty acids. PPARα activates transcription by binding to DNA sequence elements, termed peroxisome proliferator response elements (PPRE), in the form of a heterodimer with the retinoid X receptor (RXR). RXR is activated by 9-cis retinoic acid (see Kliewer et al., 1992, *Nature* 358:771 774; Gearing et al., 1993, *Proc. Natl. Acad. Sci. USA* 90:1440 1444, Keller et al., 1993, *Proc. Natl. Acad. Sci. USA* 90:2160 2164; Heyman et al., 1992, *Cell* 68:397 406, and Levin et al., 1992, *Nature* 355:359 361). Since the discovery of PPARα, additional isoforms of PPAR have been identified, e.g., PPARβ, PPARγ and PPARδ, which have similar functions and are similarly regulated.

PPARs have been identified in the enhancers of a number of gene-encoding proteins that regulate lipid metabolism. These proteins include the three enzymes required for peroxisomal β-oxidation of fatty acids; apolipoprotein A-I; medium chain acyl-CoA dehydrogenase, a key enzyme in mitochondrial β-oxidation; and aP2, a lipid binding protein expressed exclusively in adipocytes (reviewed in Keller and Whali, 1993, *TEM*, 4:291 296; see also Staels and Auwerx, 1998, *Atherosclerosis* 137 Suppl:S19 23). The nature of the PPAR target genes coupled with the activation of PPARs by fatty acids and hypolipidemic drugs suggests a physiological role for the PPARs in lipid homeostasis.

Pioglitazone, an antidiabetic compound of the thiazolidinedione class, was reported to stimulate expression of a chimeric gene containing the enhancer/promoter of the lipid binding protein aP2 upstream of the chloroamphenicol acetyl transferase reporter gene (Harris and Kletzien, 1994, *Mol. Pharmacol.* 45:439 445). Deletion analysis led to the identification of an approximately 30 bp region accounting for pioglitazone responsiveness. In an independent study, this 30 bp fragment was shown to contain a PPRE (Tontonoz et al., 1994, *Nucleic Acids Res.* 22:5628 5634). Taken together, these studies suggested the possibility that the thiazolidinediones modulate gene expression at the transcriptional level through interactions with a PPAR and reinforce the concept of the interrelatedness of glucose and lipid metabolism.

2.5 Current Cholesterol Management Therapies

In the past two decades or so, the segregation of cholesterolemic compounds into HDL and LDL regulators and recognition of the desirability of decreasing blood levels of the latter has led to the development of a number of drugs. However, many of these drugs have undesirable side effects and/or are contraindicated in certain patients, particularly when administered in combination with other drugs.

Bile-acid-binding resins are a class of drugs that interrupt the recycling of bile acids from the intestine to the liver. Examples of bile-acid-binding resins are cholestyramine (QUESTRAN LIGHT, Bristol-Myers Squibb), and colestipol hydrochloride (COLESTID, Pharmacia & Upjohn Company). When taken orally, these positively charged resins bind to negatively charged bile acids in the intestine. Because the resins cannot be absorbed from the intestine, they are excreted, carrying the bile acids with them. The use of such resins, however, at best only lowers serum cholesterol levels by about 20%. Moreover, their use is associated with gastrointestinal side-effects, including constipation and certain vitamin deficiencies. Moreover, since the resins bind to drugs, other oral medications must be taken at least one hour before or four to six hours subsequent to ingestion of the resin, complicating heart patients' drug regimens.

The statins are inhibitors of cholesterol synthesis. Sometimes, the statins are used in combination therapy with bile-acid-binding resins. Lovastatin (MEVACOR, Merck & Co., Inc.), a natural product derived from a strain of Aspergillus; pravastatin (PRAVACHOL, Bristol-Myers Squibb Co.); and atorvastatin (LIPITOR, Warner Lambert) block cholesterol synthesis by inhibiting HMGCoA reductase, the key enzyme involved in the cholesterol biosynthetic pathway. Lovastatin significantly reduces serum cholesterol and LDL-serum levels. However, serum HDL levels are only slightly increased following lovastatin administration. The mechanism of the LDL-lowering effect may involve both reduction of VLDL concentration and induction of cellular expression of LDL-receptor, leading to reduced production and/or increased catabolism of LDL. Side effects, including liver and kidney dysfunction are associated with the use of these drugs.

Nicotinic acid, also known as niacin, is a water-soluble vitamin B-complex used as a dietary supplement and antihyperlipidemic agent. Niacin diminishes the production of VLDL and is effective at lowering LDL. It is used in combination with bile-acid-binding resins. Niacin can increase HDL when administered at therapeutically effective doses; however, its usefulness is limited by serious side effects.

Fibrates are a class of lipid-lowering drugs used to treat various forms of hyperlipidemia, elevated serum triglycerides, which may also be associated with hypercholesterolemia. Fibrates appear to reduce the VLDL fraction and modestly increase HDL; however, the effects of these drugs on serum cholesterol is variable. In the United States, fibrates have been approved for use as antilipidemic drugs, but have not received approval as hypercholesterolemia agents. For example, clofibrate (ATROMID-S, Wyeth-Ayerst Laboratories) is an antilipidemic agent that acts to lower serum triglycerides by reducing the VLDL fraction. Although ATROMID-S may reduce serum cholesterol levels in certain patient subpopulations, the biochemical response to the drug is variable, and is not always possible to predict which patients will obtain favorable results. ATROMID-S has not been shown to be effective for prevention of coronary heart disease. The chemically and pharmacologically related drug, gemfibrozil (LOPID, Parke-Davis), is a lipid regulating agent which moderately decreases serum triglycerides and VLDL cholesterol. LOPED also increases HDL cholesterol, particularly the HDL2 and HDL3 subfractions, as well as both the AI/AII-HDL fractions. However, the lipid response to LOPID is heterogeneous, especially among different patient populations. Moreover, while prevention of coronary heart disease was observed in male patients between the ages of 40 and 55 without history or symptoms of existing coronary heart disease, it is not clear to what extent these findings can be extrapolated to other patient populations (e.g., women, older and younger males). Indeed, no efficacy was observed in patients with established coronary heart disease. Serious side-effects are associated with the use of fibrates, including toxicity; malignancy, particularly malignancy of gastrointestinal cancer; gallbladder disease; and an increased incidence in non-coronary mortality. These drugs are not indicated for the treatment of patients with high LDL or low HDL as their only lipid abnormality.

Oral estrogen replacement therapy may be considered for moderate hypercholesterolemia in post-menopausal women. However, increases in HDL may be accompanied with an increase in triglycerides. Estrogen treatment is, of course, limited to a specific patient population, postmenopausal women, and is associated with serious side effects, including induction of malignant neoplasms; gall bladder disease; thromboembolic disease; hepatic adenoma; elevated blood pressure; glucose intolerance; and hypercalcemia.

Long chain carboxylic acids, particularly long chain $\alpha,\omega$-dicarboxylic acids with distinctive substitution patterns, and their simple derivatives and salts, have been disclosed for treating atherosclerosis, obesity, and diabetes (See, e.g., Bisgaier et al., 1998, *J. Lipid Res.* 39:17-30, and references cited therein; International Patent Publication WO 98/30530; U.S. Pat. No. 4,689,344; International Patent Publication WO 99/00116; and U.S. Pat. No. 5,756,344). However, some of these compounds, for example the $\alpha,\omega$-dicarboxylic acids substituted at their $\alpha,\alpha'$-carbons (U.S. Pat. No. 3,773,946), while having serum triglyceride and serum cholesterol-lowering activities, have no value for treatment of obesity and hypercholesterolemia (U.S. Pat. No. 4,689,344).

U.S. Pat. No. 4,689,344 discloses $\beta,\beta,\beta',\beta'$-tetrasubstituted-$\alpha,\omega$-alkanedioic acids that are optionally substituted at their $\alpha,\alpha,\alpha',\alpha'$-positions, and alleges that they are useful for treating obesity, hyperlipidemia, and diabetes. According to this reference, both triglycerides and cholesterol are lowered significantly by compounds such as 3,3,14,14-tetramethylhexadecane-1,16-dioic acid. U.S. Pat. No. 4,689,344 further discloses that the $\beta,\beta,\beta',\beta'$-tetramethyl-alkanediols of U.S. Pat. No. 3,930,024 also are not useful for treating hypercholesterolemia or obesity.

Other compounds are disclosed in U.S. Pat. No. 4,711,896. In U.S. Pat. No. 5,756,544, $\alpha,\omega$-dicarboxylic acid-terminated dialkane ethers are disclosed to have activity in lowering certain plasma lipids, including Lp(a), triglycerides, VLDL-cholesterol, and LDL-cholesterol, in animals, and elevating others, such as HDL-cholesterol. The compounds are also stated to increase insulin sensitivity. In U.S. Pat. No. 4,613,593, phosphates of dolichol, a polyprenol isolated from swine liver, are stated to be useful in regenerating liver tissue, and in treating hyperuricuria, hyperlipemia, diabetes, and hepatic diseases in general.

U.S. Pat. No. 4,287,200 discloses azolidinedione derivatives with anti-diabetic, hypolipidemic, and anti-hypertensive properties. However, the administration of these compounds to patients can produce side effects such as bone marrow depression, and both liver and cardiac cytotoxicity. Further, the compounds disclosed by U.S. Pat. No. 4,287,200 stimulate weight gain in obese patients.

It is clear that none of the commercially available cholesterol management drugs has a general utility in regulating lipid, lipoprotein, insulin and glucose levels in the blood. Thus, compounds that have one or more of these utilities are clearly needed. Further, there is a clear need to develop safer drugs that are efficacious at lowering serum cholesterol, increasing HDL serum levels, preventing coronary heart disease, and/or treating existing disease such as atherosclerosis, obesity, diabetes, and other diseases that are affected by lipid metabolism and/or lipid levels. There is also a clear need to develop drugs that may be used with other lipid-altering treatment regimens in a synergistic manner. There is still a further need to provide useful therapeutic agents whose solubility and Hydrophile/Lipophile Balance (HLB) can be readily varied.

Citation or identification of any reference in Section 2 of this application is not an admission that such reference is available as prior art to the present invention.

3. SUMMARY OF THE INVENTION

The invention encompasses hydroxyl compounds useful in treating various disorders.

The invention further encompasses pharmaceutical compositions comprising one or more compounds of the invention and a pharmaceutically acceptable vehicle, excipient, or diluent. A pharmaceutically acceptable vehicle can comprise a carrier, excipient, diluent, or a mixture thereof.

The invention encompasses a method for treating or preventing aging, Alzheimer's Disease, cancer, cardiovascular disease, diabetic nephropathy, diabetic retinopathy, a disorder of glucose metabolism, dyslipidemia, dyslipoproteinemia, enhancing bile production, enhancing reverse lipid transport, hypertension, impotence, inflammation, insulin resistance, lipid elimination in bile, modulating C reactive protein, obesity, oxysterol elimination in bile, pancreatitis, Parkinson's disease, a peroxisome proliferator activated receptor-associated disorder, phospholipid elimination in bile, renal disease, septicemia, metabolic syndrome disorders (e.g., Syndrome X), and a thrombotic disorder, comprising administering to a patient in need of such treatment or prevention a therapeutically effective amount of a compound of the invention or a pharmaceutical composition comprising a compound of the invention and a pharmaceutically acceptable vehicle, excipient, or diluent.

The invention also encompasses a method for inhibiting hepatic fatty acid and sterol synthesis comprising administering to a patient in need thereof a therapeutically effective amount of a compound of the invention or a pharmaceutical composition comprising a compound of the invention and a pharmaceutically acceptable vehicle, excipient, or diluent.

The invention also encompasses a method of treating or preventing a disease or disorder that is capable of being treated or prevented by increasing HDL levels, which comprises administering to a patient in need of such treatment or prevention a therapeutically effective amount of a compound of the invention and a pharmaceutically acceptable vehicle, excipient, or diluent.

The invention also encompasses a method of treating or preventing a disease or disorder that is capable of being treated or prevented by lowering LDL levels, which comprises administering to such patient in need of such treatment or prevention a therapeutically effective amount of a compound of the invention and a pharmaceutically acceptable vehicle, excipient, or diluent.

The compounds of the invention favorably alter lipid metabolism in animal models of dyslipidemia at least in part by enhancing oxidation of fatty acids through the ACC/malonyl-CoA/CPT-I regulatory axis and therefore the invention also encompasses methods of treatment or prevention of metabolic syndrome disorders.

The invention further encompasses a method for reducing the fat content of meat in livestock comprising administering to livestock in need of such fat-content reduction a therapeutically effective amount of a compound of the invention or a pharmaceutical composition comprising a compound of the invention and a pharmaceutically acceptable vehicle, excipient, or diluent.

The invention encompasses a method for reducing the cholesterol content of a fowl egg comprising administering to a fowl species a therapeutically effective amount of a compound of the invention or a pharmaceutical composition comprising a compound of the invention and a pharmaceutically acceptable vehicle, excipient, or diluent.

The present invention may be understood more fully by reference to the detailed description and examples, which are intended to exemplify non-limiting embodiments of the invention.

4. DEFINITIONS AND ABBREVIATIONS

Apo(a): apolipoprotein(a)
Apo A-I: apolipoprotein A-I
Apo B: apolipoprotein B
Apo E: apolipoprotein E
FH: Familial hypercholesterolemia
FCH: Familial combined hyperlipidemia
GDM: Gestational diabetes mellitus
HDL: High density lipoprotein
IDL: Intermediate density lipoprotein
IDDM: Insulin dependent diabetes mellitus
LDH: Lactate dehdyrogenase
LDL: Low density lipoprotein
Lp(a): Lipoprotein (a)
MODY: Maturity onset diabetes of the young
NIDDM: Non-insulin dependent diabetes mellitus
PPAR: Peroxisome proliferator activated receptor
RXR: Retinoid X receptor
VLDL: Very low density lipoprotein As used herein, the phrase "compounds of the invention" means compounds disclosed herein. Particular compounds of the invention are compounds of formulas I, II, III, IV, and V, and pharmaceutically acceptable salts, hydrates, enantiomers, diastereomer, racemates or mixtures of stereoisomers thereof. The compounds of the invention are identified herein by their chemical structure and/or chemical name. Where a compound is referred to by both a chemical structure and a chemical name, and the chemical structure and chemical name conflict, the chemical structure is to be accorded more weight.

The compounds of the invention can contain one or more chiral centers and/or double bonds and, therefore, exist as stereoisomers, such as double-bond isomers (i.e., geometric isomers), enantiomers, or diastereomers. According to the invention, the chemical structures depicted herein, and therefore the compounds of the invention, encompass all of the corresponding compounds' enantiomers and stereoisomers, that is, both the stereomerically pure form (e.g., geometrically pure, enantiomerically pure, or diastereomerically pure) and enantiomeric and stereoisomeric mixtures.

As used herein, a composition that "substantially" comprises a compound means that the composition contains more than about 80% by weight, more preferably more than about 90% by weight, even more preferably more than about 95% by weight, and most preferably more than about 97% by weight of the compound.

As used herein, a reaction that is "substantially complete" means that the reaction contains more than about 80% by weight of the desired product, more preferably more than about 90% by weight of the desired product, even more preferably more than about 95% by weight of the desired product, and most preferably more than about 97% by weight of the desired product.

A compound of the invention is considered optically active or enantiomerically pure (i.e., substantially the R-form or substantially the S-form) with respect to a chiral center when the compound is about 90% ee (enantiomeric excess) or greater, preferably, equal to or greater than 95% ee with respect to a particular chiral center. A compound of the invention is considered to be in enantiomerically-enriched form when the compound has an enantiomeric excess of greater than about 1% ee, preferably greater than about 5% ee, more preferably, greater than about 10% ee with respect to a particular chiral center. A compound of the invention is considered diastereomerically pure with respect to multiple chiral centers when the compound is about 90% de (diastereomeric excess) or greater, preferably, equal to or greater than 95% de with respect to a particular chiral center. A compound of the invention is considered to be in diastereomerically-enriched form when the compound has an diastereomeric excess of greater than about 1% de, preferably greater than about 5% de, more preferably, greater than about 10% de with respect to a particular chiral center. As used herein, a racemic mixture means about 50% of one enantiomer and about 50% of is corresponding enantiomer relative to all chiral centers in the molecule. Thus, the invention encompasses all enantiomerically-pure, enantiomerically-enriched, diastereomerically pure, diastereomerically enriched, and racemic mixtures of compounds of Formulas I through V.

Enantiomeric and diastereomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic methods.

The compounds of the invention are defined herein by their chemical structures and/or chemical names. Where a compound is referred to by both a chemical structure and a chemical name, and the chemical structure and chemical name conflict, the chemical structure is determinative of the compound's identity.

When administered to a patient, e.g., to an animal for veterinary use or for improvement of livestock, or to a human for clinical use, the compounds of the invention are administered in isolated form or as the isolated form in a pharmaceutical composition. As used herein, "isolated" means that the compounds of the invention are separated from other components of either (a) a natural source, such as a plant or cell, preferably bacterial culture, or (b) a synthetic organic chemical reaction mixture. Preferably, via conventional techniques, the compounds of the invention are purified. As used herein, "purified" means that when isolated, the isolate contains at least 95%, preferably at least 98%, of a single hydroxy compound of the invention by weight of the isolate.

The phrase "pharmaceutically acceptable salt(s)," as used herein includes, but is not limited to, salts of acidic or basic groups that may be present in the compounds of the invention. Compounds that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds of the invention that include an amino moiety also can form pharmaceutically acceptable salts with various amino acids, in addition to the acids mentioned above. Compounds of the invention that are acidic in nature are capable of forming base salts with various pharmacologically acceptable cations. Examples of such salts include alkali metal or alkaline earth metal salts and, particularly, calcium, magnesium, sodium lithium, zinc, potassium, and iron salts.

As used herein, the term "hydrate" means a compound of the invention or a salt thereof, that further includes a stoichiometric or non-stoichiometric amount of water bound by non-covalent intermolecular forces. The term hydrate includes solvates, which are stoichiometric or non-stoichiometric amounts of a solvent bound by non-covalent intermolecular forces. Preferred solvents are volatile, non-toxic, and/or acceptable for administration to humans in trace amounts.

As used herein, the term "altering lipid metabolism" indicates an observable (measurable) change in at least one aspect of lipid metabolism, including but not limited to total blood lipid content, blood HDL cholesterol, blood LDL cholesterol, blood VLDL cholesterol, blood triglyceride, blood Lp(a), blood apo A-I, blood apo E and blood non-esterified fatty acids.

As used herein, the term "altering glucose metabolism" indicates an observable (measurable) change in at least one aspect of glucose metabolism, including but not limited to total blood glucose content, blood insulin, the blood insulin to blood glucose ratio, insulin sensitivity, and oxygen consumption.

As used herein, the term "alkyl group" means a saturated, monovalent unbranched or branched hydrocarbon chain. Examples of alkyl groups include, but are not limited to, $(C_1-C_6)$alkyl groups, such as methyl, ethyl, propyl, isopropyl, 2-methyl-1-propyl, 2 methyl 2-propyl, 2-methyl-1-butyl, 3-methyl-1-butyl, 2 methyl-3-butyl, 2,2 dimethyl 1-propyl, 2-methyl-1-pentyl, 3 methyl-1-pentyl, 4 methyl-1-pentyl, 2-methyl-2-pentyl, 3-methyl-2-pentyl, 4 methyl 2 pentyl, 2,2 dimethyl 1 butyl, 3,3-dimethyl-1-butyl, 2-ethyl-1-butyl, butyl, isobutyl, t-butyl, pentyl, isopentyl, neopentyl, and hexyl, and longer alkyl groups, such as heptyl, and octyl. An alkyl group can be unsubstituted or substituted with one or two suitable substituents.

As used herein, the term an "alkenyl group" means a monovalent unbranched or branched hydrocarbon chain having one or more double bonds therein. The double bond of an alkenyl group can be unconjugated or conjugated to another unsaturated group. Suitable alkenyl groups include, but are not limited to $(C_2-C_6)$alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl group can be unsubstituted or substituted with one or two suitable substituents.

As used herein, the term an "alkynyl group" means monovalent unbranched or branched hydrocarbon chain having one or more triple bonds therein. The triple bond of an alkynyl group can be unconjugated or conjugated to another unsaturated group. Suitable alkynyl groups include, but are not limited to, $(C_2-C_6)$alkynyl groups, such as ethynyl, propynyl, butynyl, pentynyl, hexynyl, methylpropynyl, 4-methyl-1-butynyl, 4-propyl-2-pentynyl, and 4-butyl-2-hexynyl. An alkynyl group can be unsubstituted or substituted with one or two suitable substituents.

As used herein, the term an "aryl group" means a monocyclic or polycyclic-aromatic radical comprising carbon and hydrogen atoms. Examples of suitable aryl groups include, but are not limited to, phenyl, tolyl, anthacenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or two suitable substituents. Preferably, the aryl group is a monocyclic ring, wherein the ring comprises 6 carbon atoms, referred to herein as "$(C_6)$aryl".

As used herein, the term an "heteroaryl group" means a monocyclic- or polycyclic aromatic ring comprising carbon atoms, hydrogen atoms, and one or more heteroatoms, preferably 1 to 3 heteroatoms, independently selected from nitrogen, oxygen, and sulfur. Illustrative examples of heteroaryl groups include, but are not limited to, pyridinyl, pyridazinyl, pyrimidinyl, pyrazyl, triazinyl, pyrrolyl, pyrazolyl, imidazolyl, (1,2,3)- and (1,2,4)-triazolyl, pyrazinyl, pyrimidinyl, tetrazolyl, furyl, thiophenyl, isoxazolyl, thiazolyl, furyl, phenyl, isoxazolyl, and oxazolyl. A heteroaryl group can be unsubstituted or substituted with one or two suitable substituents. Preferably, a heteroaryl group is a monocyclic ring, wherein the ring comprises 2 to 5 carbon atoms and 1 to 3 heteroatoms, referred to herein as "$(C_2-C_5)$heteroaryl".

As used herein, the term "cycloalkyl group" means a monocyclic or polycyclic saturated ring comprising carbon and hydrogen atoms and having no carbon-carbon multiple bonds. Examples of cycloalkyl groups include, but are not limited to, $(C_3-C_7)$cycloalkyl groups, such as cyclopropyl, cyclobutyl, cyclopentyl, cyclohexyl, and cycloheptyl, and saturated cyclic and bicyclic terpenes. A cycloalkyl group can be unsubstituted or substituted by one or two suitable substituents. Preferably, the cycloalkyl group is a monocyclic ring or bicyclic ring.

As used herein, the term "heterocycloalkyl group" means a monocyclic or polycyclic ring comprising carbon and hydrogen atoms and at least one heteroatom, preferably, 1 to 3 heteroatoms selected from nitrogen, oxygen, and sulfur, and having no unsaturation. Examples of heterocycloalkyl groups include pyrrolidinyl, pyrrolidino, piperidinyl, piperidino, piperazinyl, piperazino, morpholinyl, morpholino, thiomorpholinyl, thiomorpholino, and pyranyl. A heterocycloalkyl group can be unsubstituted or substituted with one or two suitable substituents. Preferably, the heterocycloalkyl group is a monocyclic or bicyclic ring, more preferably, a monocyclic ring, wherein the ring comprises from 3 to 6 carbon atoms and form 1 to 3 heteroatoms, referred to herein as $(C_1-C_6)$ heterocycloalkyl.

As used herein, the terms "heterocyclic radical" or "heterocyclic ring" mean a heterocycloalkyl group or a heteroaryl group.

As used herein, the term "alkoxy group" means an —O-alkyl group, wherein alkyl is as defined above. An alkoxy group can be unsubstituted or substituted with one or two suitable substituents. Preferably, the alkyl chain of an alkyloxy group is from 1 to 6 carbon atoms in length, referred to herein as "$(C_1-C_6)$alkoxy".

As used herein, the term "aryloxy group" means an —O-aryl group, wherein aryl is as defined above. An aryloxy group can be unsubstituted or substituted with one or two suitable substituents. Preferably, the aryl ring of an aryloxy group is a monocyclic ring, wherein the ring comprises 6 carbon atoms, referred to herein as "$(C_6)$aryloxy".

As used herein, the term "benzyl" means —$CH_2$-phenyl.

As used herein, the term "phenyl" means —$C_6H_5$. A phenyl group can be unsubstituted or substituted with one or two suitable substituents, wherein the substituent replaces an H of the phenyl group. As used herein, "Ph," represents a phenyl group or a substituted phenyl group.

As used herein, the term "hydrocarbyl" group means a monovalent group selected from $(C_1-C_8)$alkyl, $(C_2-C_8)$alkenyl, and $(C_2-C_8)$alkynyl, optionally substituted with one or two suitable substituents. Preferably, the hydrocarbon chain of a hydrocarbyl group is from 1 to 6 carbon atoms in length, referred to herein as "$(C_1-C_6)$hydrocarbyl".

As used herein, a "carbonyl" group is a divalent group of the formula C(O).

As used herein, the term "alkoxycarbonyl" group means a monovalent group of the formula —C(O)-alkoxy. Preferably, the hydrocarbon chain of an alkoxycarbonyl group is from 1 to 8 carbon atoms in length, referred to herein as a "lower alkoxycarbonyl" group.

As used herein, a "carbamoyl" group means the radical —C(O)N(R')$_2$,
wherein R' is chosen from the group consisting of hydrogen, alkyl, and aryl.

As used herein, "halogen" means fluorine, chlorine, bromine, or iodine. Accordingly, the meaning of the terms "halo" and "Hal" encompass fluoro, chloro, bromo, and iodo.

As used herein, a "suitable substituent" means a group that does not nullify the synthetic or pharmaceutical utility of the compounds of the invention or the intermediates useful for preparing them. Examples of suitable substituents include, but are not limited to: $(C_1-C_8)$alkyl; $(C_1-C_8)$alkenyl; $(C_1-C_8)$alkylynyl; $(C_6)$aryl; $(C_2-C_5)$heteroaryl; $(C_3-C_7)$cycloalkyl; $(C_1-C_8)$alkoxy; $(C_6)$aryloxy; —CN; —OH; oxo; halo, —$CO_2$H; —$NH_2$; —NH($(C_1-C_8)$alkyl); —N($(C_1-C_8)$alkyl)$_2$; —NH($(C_6)$aryl); —N($(C_6)$aryl)$_2$; —CHO; —CO($(C_1-C_8)$alkyl); —CO($(C_6)$aryl); —$CO_2$($(C_1-C_8)$alkyl); and —$CO_2$ (($C_6$)aryl). One of skill in the art can readily choose a suitable substituent based on the stability and pharmacological and synthetic activity of the compound of the invention.

As used herein, a composition that is "substantially free" of a compound means that the composition contains less than about 20% by weight, more preferably less than about 10% by weight, even more preferably less than about 5% by weight, and most preferably less than about 3% by weight of the compound.

5. DETAILED DESCRIPTION OF THE INVENTION

The compounds of the invention are useful in medical applications for treating or preventing a variety of diseases and disorders such as, but not limited to, cardiovascular disease, stroke, and peripheral vascular disease; dyslipidemia; dyslipoproteinemia; a disorder of glucose metabolism; Alzheimer's Disease; Parkinson's Disease, diabetic nephropathy, diabetic retinopathy, insulin resistance, Syndrome X; a peroxisome proliferator activated receptor-associated disorder; septicemia; a thrombotic disorder; obesity; pancreatitis; hypertension; renal disease; cancer; inflammation; inflammatory muscle diseases, such as polymylagia rheumatica, polymyositis, and fibrositis; impotence; gastrointestinal disease; irritable bowel syndrome; inflammatory bowel disease; inflammatory disorders, such as asthma, vasculitis, ulcerative colitis, Crohn's disease, Kawasaki disease, Wegener's granulomatosis, (RA), systemic lupus erythematosus (SLE), multiple sclerosis (MS), and autoimmune chronic hepatitis; arthritis, such as rheumatoid arthritis, juvenile rheumatoid arthritis, and osteoarthritis; osteoporosis, soft tissue rheumatism, such as tendonitis; bursitis; autoimmune disease, such as systemic lupus and erythematosus; scleroderma; ankylosing spondylitis; gout; pseudogout; non-insulin dependent diabetes mellitus; polycystic ovarian disease; hyperlipidemias, such as familial hypercholesterolemia (FH), familial combined hyperlipidemia (FCH); lipoprotein lipase deficiencies, such as hypertriglyceridemia, hypoalphalipoproteinemia, and hypercholesterolemia; lipoprotein abnormalities associated with diabetes; lipoprotein abnormalities associated with obesity; and lipoprotein abnormalities associated with Alzheimer's Disease. The compounds and compositions of the invention are useful for treatment or prevention of high levels of blood triglycerides, high levels of low density lipoprotein cholesterol, high levels of apolipoprotein B, high levels of lipoprotein Lp(a) cholesterol, high levels of very low density lipoprotein cholesterol, high levels of fibrinogen, high levels of insulin, high levels of glucose, and low levels of high density lipoprotein cholesterol. The compounds and compositions of the invention also have utility for treatment of NIDDM without increasing weight gain. The compounds of the invention may also be used to reduce the fat content of meat in livestock and reduce the cholesterol content of eggs.

The invention provides novel compounds particularly useful for treating or preventing a variety of diseases and conditions, which include, but are not limited to aging, Alzheimer's Disease, cancer, cardiovascular disease, diabetic nephropathy, diabetic retinopathy, a disorder of glucose metabolism, dyslipidemia, dyslipoproteinemia, enhancing bile production, hypertension, impotence, inflammation, insulin resistance, lipid elimination in bile, modulating C reactive protein, obesity, oxysterol elimination in bile, pancreatitis, pancreatitius, Parkinson's disease, a peroxisome proliferator activated receptor-associated disorder, phospholipid elimination in bile, renal disease, septicemia, metabolic syndrome disorders (e.g., Syndrome X), and a thrombotic disorder.

The invention encompasses compounds of formula I:

or a pharmaceutically acceptable salt, hydrate, solvate or a mixture thereof, wherein:
(a) each occurrence of m is independently an integer ranging from 0 to 5;
(b) each occurrence of n is independently an integer ranging from 3 to 7;
(c) X is $(CH_2)_z$ or Ph, wherein z is an integer from 0 to 4;
(d) each occurrence of $R^1$ and $R^2$ is independently $(C_1$-$C_6)$ alkyl, $(C_2$-$C_6)$alkenyl, $(C_2$-$C_6)$alkynyl, phenyl, benzyl, or $R^1$ and $R^2$ and the carbon to which they are both attached are taken together to form a $(C_3$-$C_7)$cycloakyl group;
(e) each occurrence of $R^{11}$ and $R^{12}$ and the carbon to which they are both attached are taken together to form a $(C_3$-$C_7)$ cycloakyl group;
(f) each occurrence of $Y^1$ and $Y^2$ is independently $(C_1$-$C_6)$ alkyl, OH, COOH, $COOR^S$, $SO_3H$, wherein:
(i) $R^3$ is $(C_1$-$C_6)$alkyl, $(C_2$-$C_6)$alkenyl, $(C_2$-$C_6)$alkynyl, phenyl, or benzyl and is unsubstituted or substituted with one or more halo, OH, $(C_1$-$C_6)$alkoxy, or phenyl groups,
(ii) each occurrence of $R^4$ is independently H, $(C_1$-$C_6)$ alkyl, $(C_2$-$C_6)$alkenyl, or $(C_2$-$C_6)$alkynyl and is unsubstituted or substituted with one or two halo, OH, $C_1$-$C_6$ alkoxy, or phenyl groups; and
(iii) each occurrence of $R^5$ is independently H, $(C_1$-$C_6)$ alkyl, $(C_2$-$C_6)$alkenyl, or $(C_2$-$C_6)$alkynyl.

In an exemplary compound of formula I, each occurrence of Y is independently OH, $COOR^S$, or COOH.

Other compounds of formula I are those wherein m is 0.
Other compounds of formula I are those wherein m is 1.
Other compounds of formula I are those wherein n is 4.
Other compounds of formula I are those wherein n is 5.
Other compounds of formula I are those wherein z is 0.
Other compounds of formula I are those wherein z is 1.
Other compounds of formula I are those wherein $Y^1$ and $Y^2$ are each independently $(C_1$-$C_6)$alkyl.
Other compounds of formula I are those wherein $Y^1$ and $Y^2$ are each methyl.
Other compounds of formula I are those wherein each occurrence $R^1$ and $R^2$ and the carbon to which they are both attached are taken together to form a $(C_3$-$C_7)$cycloakyl group.

In another embodiment, the invention encompasses compounds of the formula II:

or a pharmaceutically acceptable salt, hydrate, solvate, or mixture thereof, wherein (a) each occurrence of $R^1$ and $R^2$ is independently $(C_1-C_6)$ alkyl, $(C_2-C_6)$alkenyl, $(C_2-C_6)$alkynyl, phenyl, benzyl, or $R^1$ and $R^2$ and the carbon to which they are both attached are taken together to form a $(C_3-C_7)$cycloakyl group;

(b) each occurrence of $R^{11}$ and $R^{12}$ and the carbon to which they are both attached are taken together to form a $(C_3-C_7)$ cycloakyl group;

(c) each occurrence of n is independently an integer ranging from 1 to 7;

(d) X is $(CH_2)_z$ or Ph, wherein z is an integer from 0 to 4;

(e) each occurrence of m is independently an integer ranging from 0 to 4;

(f) each occurrence of $Y^1$ and $Y^2$ is independently $(C_1-C_6)$ alkyl, $CH_2OH$, $C(O)OH$, $OC(O)R^3$, $C(O)OR^3$, $SO_3H$,

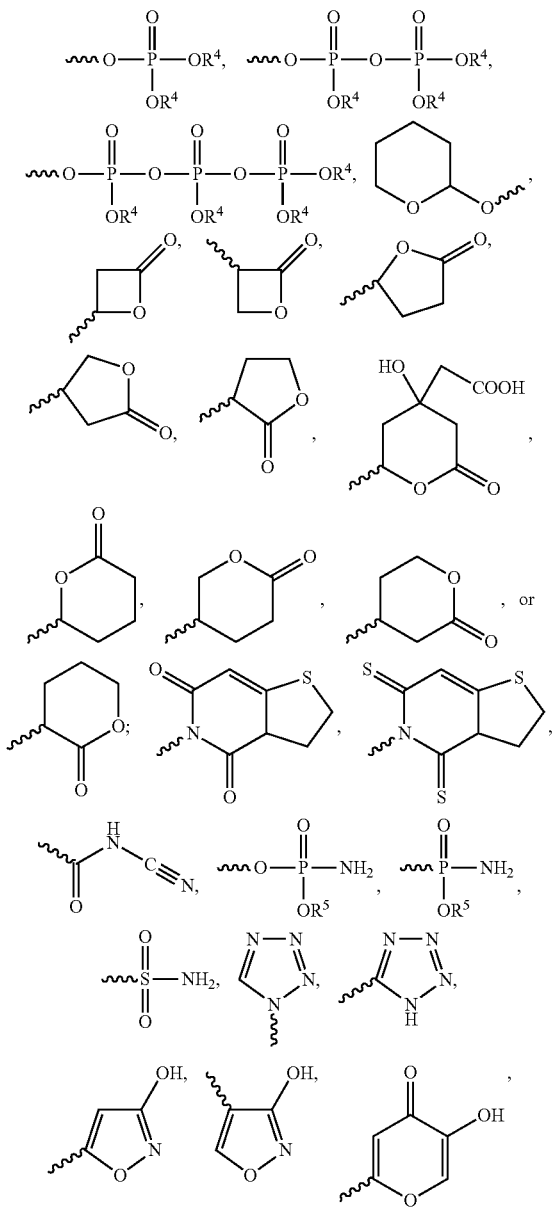

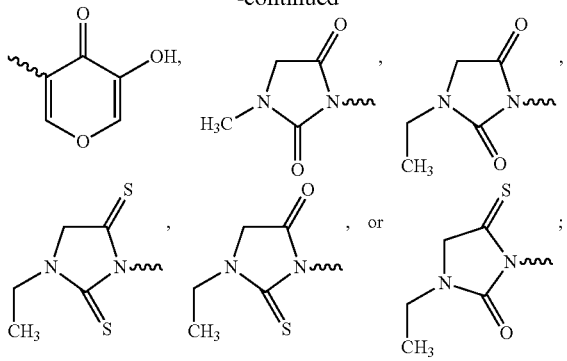

wherein:

(i) $R^3$ is $(C_1-C_6)$alkyl, $(C_2-C_6)$alkenyl, $(C_2-C_6)$alkynyl, phenyl, or benzyl and is unsubstituted or substituted with one or more halo, OH, $(C_1-C_6)$alkoxy, or phenyl groups, (ii) each occurrence of $R^4$ is independently H, $(C_1-C_6)$ alkyl, $(C_2-C_6)$alkenyl, or $(C_2-C_6)$alkynyl and is unsubstituted or substituted with one or two halo, OH, $C_1-C_6$ alkoxy, or phenyl groups;

(iii) each occurrence of $R^5$ is independently H, $(C_1-C_6)$ alkyl, $(C_2-C_6)$alkenyl, or $(C_2-C_6)$alkynyl; and (g) b is 0 or 1 or optionally the presence of one or more additional carbon-carbon bonds that when present complete one or more carbon-carbon double bonds.

Exemplary compounds of formula II are those in which each occurrence of $R^1$ and $R^2$ and the carbon to which they are both attached are taken together to form a $(C_3-C_7)$cycloakyl group.

In another embodiment, the invention encompasses compounds of formula III:

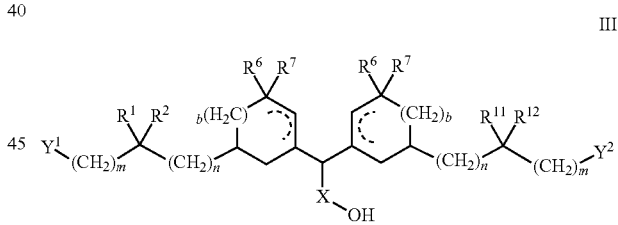

III or a pharmaceutically acceptable salt, hydrate, solvate, or mixtures thereof, wherein:

(a) each occurrence of $R^1$ and $R^2$ is independently $(C_1-C_6)$ alkyl, $(C_2-C_6)$alkenyl, $(C_2-C_6)$alkynyl, phenyl, benzyl, or $R^1$ and $R^2$ and the carbon to which they are both attached are taken together to form a $(C_3-C_7)$cycloakyl group;

(b) each occurrence of $R^{11}$ and $R^{12}$ and the carbon to which they are both attached are taken together to form a $(C_3-C_7)$ cycloakyl group;

(c) each occurrence of n is independently an integer ranging from 1 to 7;

(d) X is $(CH_2)_z$ or Ph, wherein z is an integer from 0 to 4;

(e) each occurrence of m is independently an integer ranging from 0 to 4;

(f) each occurrence of $Y^1$ and $Y^2$ is independently $(C_1-C_6)$ alkyl, $CH_2OH$, $C(O)OH$, $OC(O)R^3$, $C(O)OR^3$, $SO_3H$,

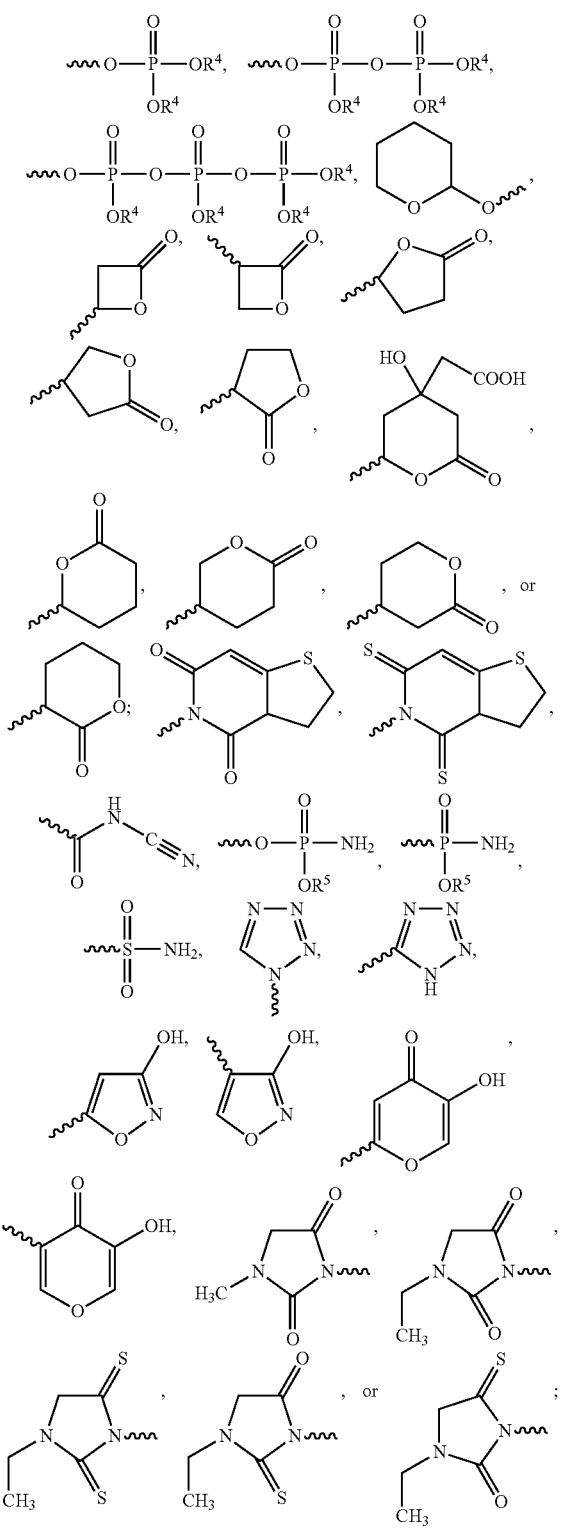

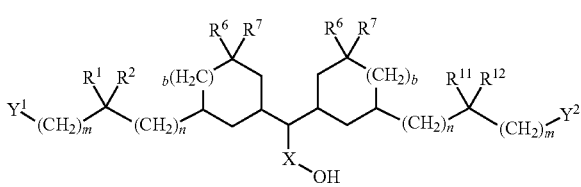

wherein:
(i) $R^3$ is $(C_1-C_6)$alkyl, $(C_2-C_6)$alkenyl, $(C_2-C_6)$alkynyl, phenyl, or benzyl and is unsubstituted or substituted with one or more halo, OH, $(C_1-C_6)$alkoxy, or phenyl groups,
(ii) each occurrence of $R^4$ is independently H, $(C_1-C_6)$ alkyl, $(C_2-C_6)$alkenyl, or $(C_2-C_6)$alkynyl and is unsubstituted or substituted with one or two halo, OH, $C_1-C_6$ alkoxy, or phenyl groups;
(iii) each occurrence of $R^5$ is independently H, $(C_1-C_6)$ alkyl, $(C_2-C_6)$alkenyl, or $(C_2-C_6)$alkynyl; and
(f) each occurrence of b is independently 0 or 1 or optionally the presence of one or more additional carbon-carbon bonds that when present complete one or more carbon-carbon double bonds.

In another embodiment, the invention encompasses compounds of formula IV:

$$Y^1_{(CH_2)_m} \underset{(CH_2)_n}{\overset{R^1 R^2}{|}} \underset{(CH_2)_n}{\overset{b(H_2C)}{|}} \overset{R^6 R^7}{\underset{X}{|}} \overset{R^6 R^7}{\underset{OH}{|}} \overset{(CH_2)_b}{\underset{(CH_2)_n}{|}} \overset{R^{11} R^{12}}{\underset{(CH_2)_m}{|}} Y^2$$

IV or a pharmaceutically acceptable salt, hydrate, solvate, or mixture thereof, wherein
(a) each occurrence of $R^1$ and $R^2$ is independently $(C_1-C_6)$ alkyl, $(C_2-C_6)$alkenyl, $(C_2-C_6)$alkynyl, phenyl, benzyl, or $R^1$ and $R^2$ and the carbon to which they are both attached are taken together to form a $(C_3-C_7)$cycloakyl group;
(b) each occurrence of $R^{11}$ and $R^{12}$ and the carbon to which they are both attached are taken together to form a $(C_3-C_7)$ cycloakyl group;
(c) each occurrence of n is independently an integer ranging from 1 to 7;
(d) X is $(CH_2)_z$ or Ph, wherein z is an integer from 0 to 4;
(e) each occurrence of m is independently an integer ranging from 0 to 4;
(f) each occurrence of $Y^1$ and $Y^2$ is independently $(C_1-C_6)$ alkyl, $CH_2OH$, $C(O)OH$, $OC(O)R^3$, $C(O)OR^3$, $SO_3H$,

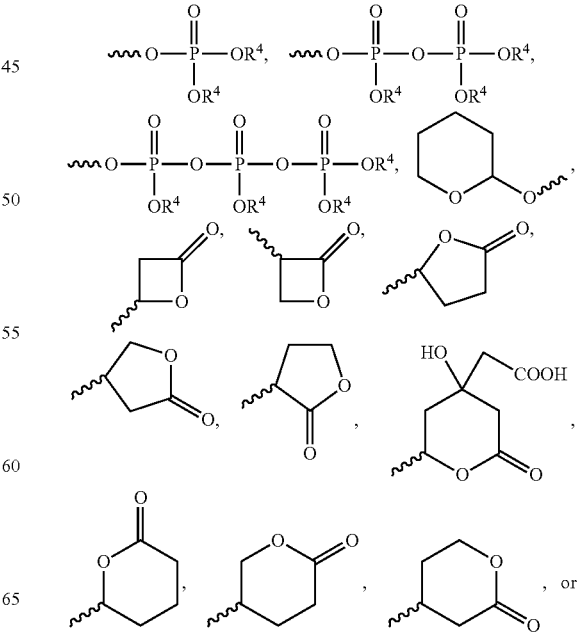

-continued

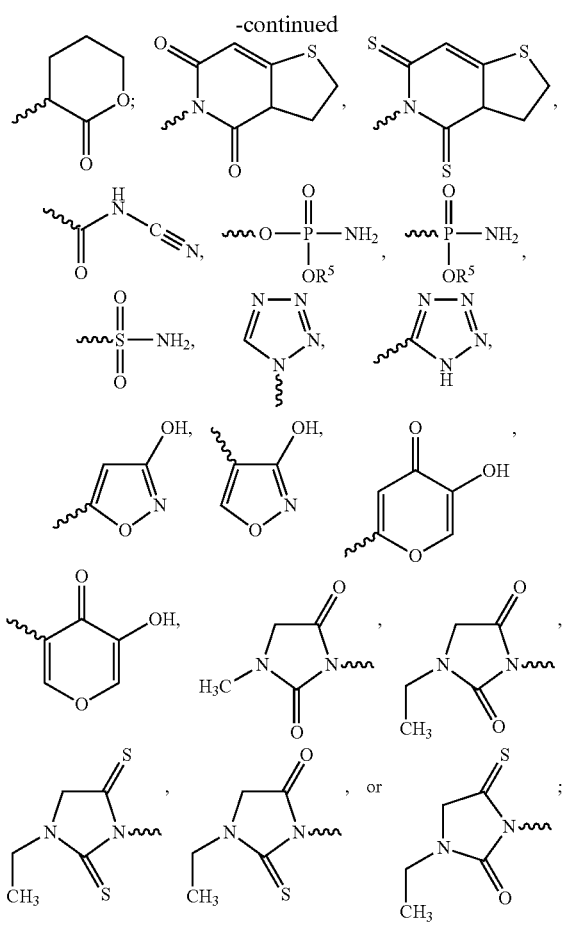

wherein:
(i) $R^3$ is $(C_1-C_6)$alkyl, $(C_2-C_6)$alkenyl, $(C_2-C_6)$alkynyl, phenyl, or benzyl and is unsubstituted or substituted with one or more halo, OH, $(C_1-C_6)$alkoxy, or phenyl groups,
(ii) each occurrence of $R^4$ is independently H, $(C_1-C_6)$ alkyl, $(C_2-C_6)$alkenyl, or $(C_2-C_6)$alkynyl and is unsubstituted or substituted with one or two halo, OH, $C_1-C_6$ alkoxy, or phenyl groups;
(iii) each occurrence of $R^5$ is independently H, $(C_1-C_6)$ alkyl, $(C_2-C_6)$alkenyl, or $(C_2-C_6)$alkynyl; and
(g) b is 0 or 1 or optionally the presence of one or more additional carbon-carbon bonds that when present complete one or more carbon-carbon double bonds.

In another embodiment, the invention encompasses compounds of formula V:

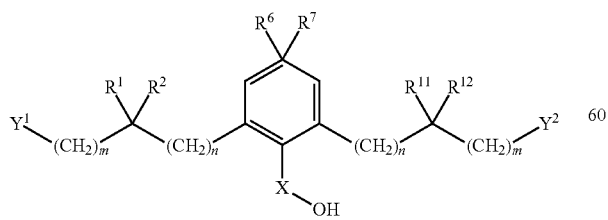

V or a pharmaceutically acceptable salt, hydrate, solvate, or mixture thereof, wherein (a) each occurrence of $R^1$ and $R^2$ is independently $(C_1-C_6)$ alkyl, $(C_2-C_6)$alkenyl, $(C_2-C_6)$alkynyl, phenyl, benzyl, or $R^1$ and $R^2$ and the carbon to which they are both attached are taken together to form a $(C_3-C_7)$cycloakyl group;
(b) each occurrence of $R^{11}$ and $R^{12}$ and the carbon to which they are both attached are taken together to form a $(C_3-C_7)$ cycloakyl group;
(c) each occurrence of n is independently an integer ranging from 1 to 7;
(d) X is $(CH_2)_z$ or Ph, wherein z is an integer from 0 to 4;
(e) each occurrence of m is independently an integer ranging from 0 to 4; and
(f) each occurrence of $Y^1$ and $Y^2$ is independently $(C_1-C_6)$ alkyl, $CH_2OH$, $C(O)OH$, $OC(O)R^3$, $C(O)OR^3$, $SO_3H$,

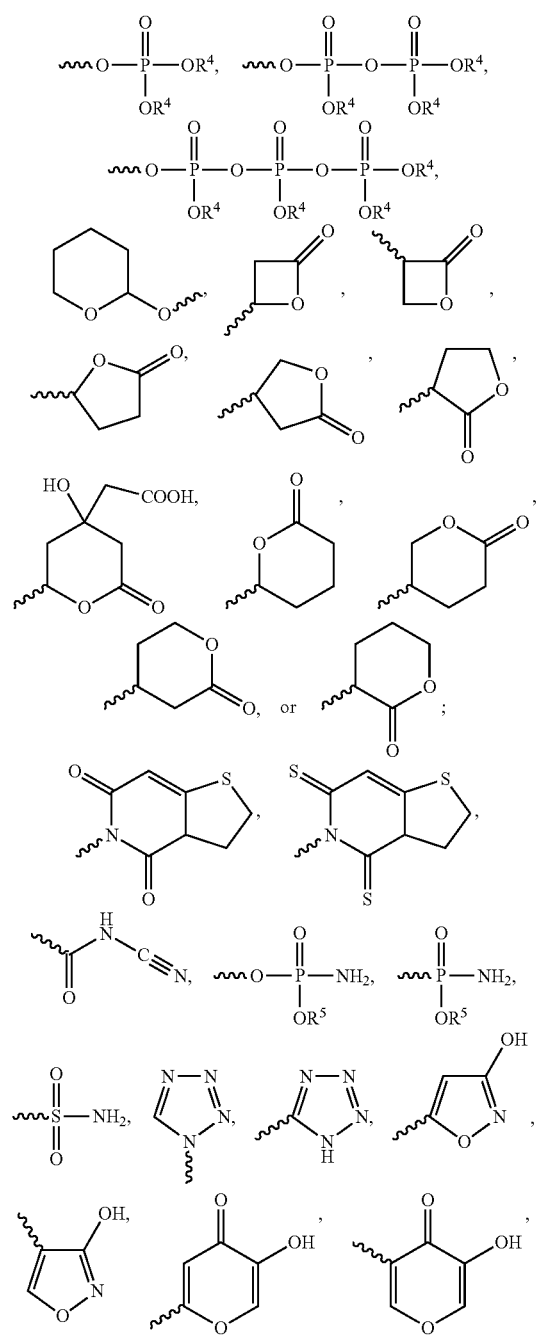

-continued

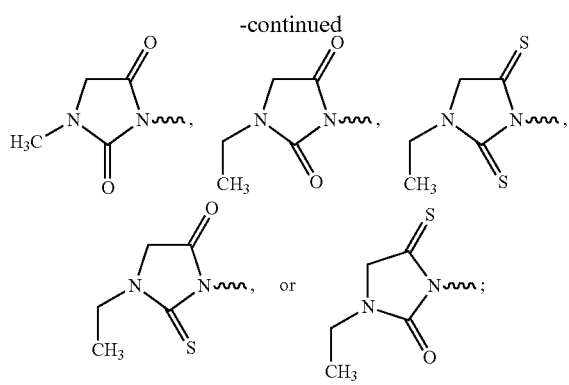

wherein:
(i) $R^3$ is $(C_1-C_6)$alkyl, $(C_2-C_6)$alkenyl, $(C_2-C_6)$alkynyl, phenyl, or benzyl and is unsubstituted or substituted with one or more halo, OH, $(C_1-C_6)$alkoxy, or phenyl groups,
(ii) each occurrence of $R^4$ is independently H, $(C_1-C_6)$ alkyl, $(C_2-C_6)$alkenyl, or $(C_2-C_6)$alkynyl and is unsubstituted or substituted with one or two halo, OH, $C_1-C_6$ alkoxy, or phenyl groups; and
(iii) each occurrence of $R^5$ is independently H, $(C_1-C_6)$ alkyl, $(C_2-C_6)$alkenyl, or $(C_2-C_6)$alkynyl.

The present invention further encompasses pharmaceutical compositions comprising one or more compounds of the invention. Particular pharmaceutical compositions further comprise pharmaceutically acceptable vehicle, which can comprise a carrier, excipient, diluent, or a mixture thereof.

The present invention encompasses a method for treating or preventing aging, Alzheimer's Disease, cancer, cardiovascular disease, diabetic nephropathy, diabetic retinopathy, a disorder of glucose metabolism, dyslipidemia, dyslipoproteinemia, enhancing bile production, enhancing reverse lipid transport, hypertension, impotence, inflammation, insulin resistance, lipid elimination in bile, modulating C reactive protein, obesity, oxysterol elimination in bile, pancreatitis, Parkinson's disease, a peroxisome proliferator activated receptor-associated disorder, phospholipid elimination in bile, renal disease, septicemia, metabolic syndrome disorders (e.g., Syndrome X), and a thrombotic disorder, comprising administering to a patient in need of such treatment or prevention a therapeutically effective amount of a compound of the invention.

The present invention further encompasses a method of treating or preventing a disease or disorder that is capable of being treated or prevented by increasing HDL levels, which comprises administering to a patient in need of such treatment or prevention a therapeutically effective amount of a compound.

The present invention further encompasses a method of treating or preventing a disease or disorder that is capable of being treated or prevented by decreasing LDL levels, which comprises administering to a patient in need of such treatment or prevention a therapeutically effective amount of a compound.

The present invention further encompasses a method for reducing the fat content of meat in livestock comprising administering to livestock in need of such fat-content reduction a therapeutically effective amount of a compound of the invention or a pharmaceutical composition.

The present invention encompasses a method for reducing the cholesterol content of a fowl egg comprising administering to a fowl species a therapeutically effective amount of a compound of the invention.

The compounds of the invention are particularly useful when incorporated in a pharmaceutical composition comprising a carrier, excipient, diluent, or a mixture thereof. However, a compound of the invention need not be administered with excipients or diluents and can be delivered in a gel cap or drug delivery device.

In certain embodiments of the invention, a compound of the invention is administered in combination with another therapeutic agent. The other therapeutic agent provides additive or synergistic value relative to the administration of a compound of the invention alone. Examples of other therapeutic agents include, but are not limited to, a lovastatin; a thiazolidinedione or fibrate; a bile-acid-binding-resin; a niacin; an anti-obesity drug; a hormone; a tyrophostine; a sulfonylurea-based drug; a biguanide; an α-glucosidase inhibitor; an apolipoprotein A-I agonist; apolipoprotein E; a cardiovascular drug; an HDL-raising drug; an HDL enhancer; or a regulator of the apolipoprotein A-I, apolipoprotein A-IV and/or apolipoprotein genes.

Illustrative examples of compounds of the invention include those shown below, and pharmaceutically acceptable salts, hydrates, enantiomers, diastereomers, and geometric isomers thereof:

Compound 1

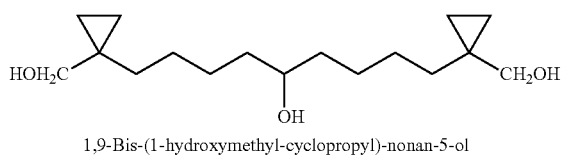

1,9-Bis-(1-hydroxymethyl-cyclopropyl)-nonan-5-ol

Compound 2

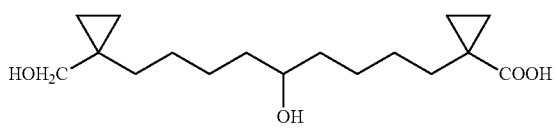

1-[5-Hydroxy-9-(1-hydroxymethyl-cyclopropyl)-nonyl]-cyclopropanecarboxylic acid

Compound 3

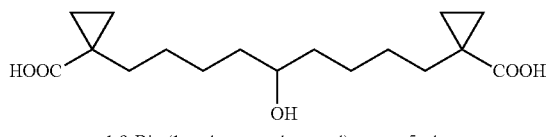

1,9-Bis-(1-carboxy-cyclopropyl)-nonan-5-ol

Compound 4

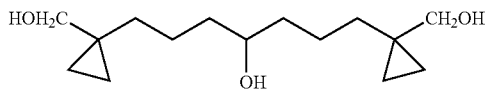

1,7-Bis-(1-hydroxymethyl-cyclopropyl)-heptan-4-ol

-continued

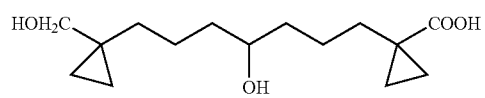

Compound 5
1-[4-Hydroxy-7-(1-hydroxymethyl-cyclopropyl)-heptyl]-cyclopropaneocarboxylic acid

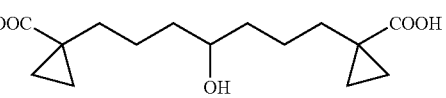

Compound 6
1,7-Bis-(1-carboxy-cyclopropyl)-heptan-4-ol

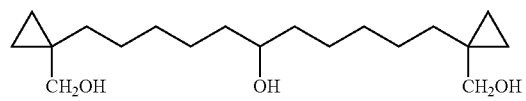

Compound 7
1,11-Bis-(1-hydroxymethyl-cyclopropyl)-undecan-6-ol

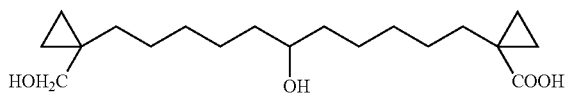

Compound 8
1-[6-Hydroxy-11-(1-hydroxymethyl-cyclopropyl)-undecyl]-cyclopropanecarboxylic acid

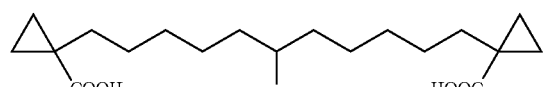

Compound 9
1,11-Bis-(1-carboxy-cyclopropyl)-undecan-6-ol

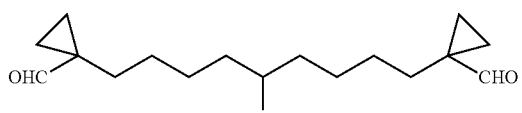

Compound 10
1,9-Bis-(1-oxa-cyclopropyl)-nonan-5-ol

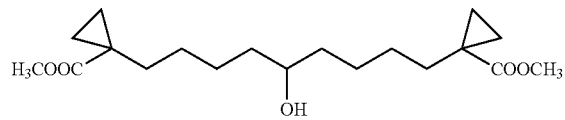

Compound 11
1,9-Bis-(1-carbomethoxy-cyclopropyl)-nonan-5-ol

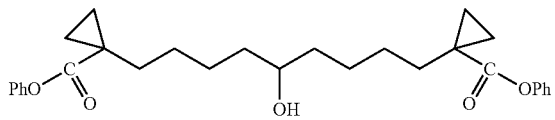

Compound 12
1,9-Bis-(1-phenoxycarbonyl-cyclopropyl)-nonan-5-ol

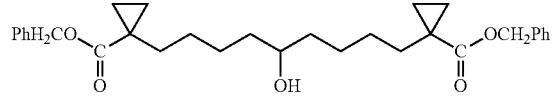

Compound 13
1,9-Bis-(1-benzyloxycarbonyl-cyclopropyl)-nonan-5-ol

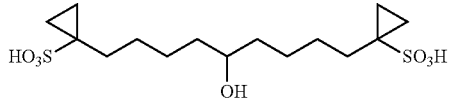

Compound 14
1,9-Bis-(1-sulfonyloxy-cyclopropyl)-nonan-5-ol

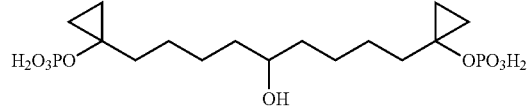

Compound 15
1,9-Bis-(1-phosphonooxy-cyclopropyl)-nonan-5-ol

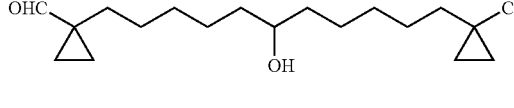

Compound 16
1,11-Bis-(1-oxa-cyclopropyl)-undecan-6-ol

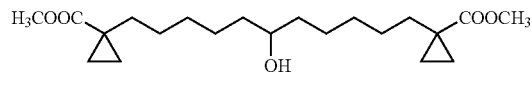

Compound 17
1,11-Bis-(1-carbomethyoxy-cyclopropyl)-undecan-6-ol

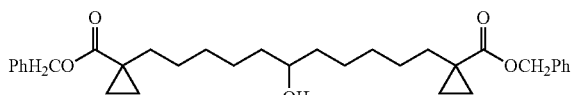

Compound 18
1,11-Bis-(1-benzyloxycarbonyl-cyclopropyl)-undecan-6-ol

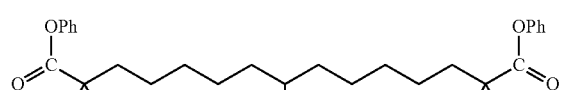

Compound 19
1,11-Bis-(1-phenoxycarbonyl-cyclopropyl)-undecan-6-ol

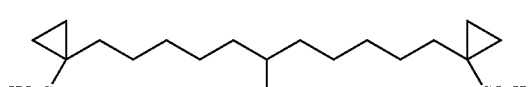

Compound 20
1,11-Bis-(1-sulfonyloxy-cyclopropyl)-undecan-6-ol

-continued

Compound 21

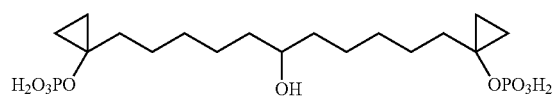

1,9-Bis-(1-phosphonooxy-cyclopropyl)-nonan-5-ol

Compound 22

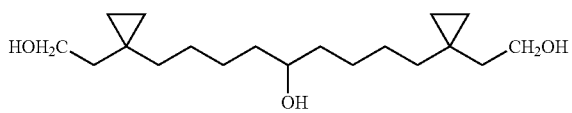

1,9-Bis-[1-(2-hydroxy-ethyl)-cyclopropyl)-nonan-5-ol

Compound 23

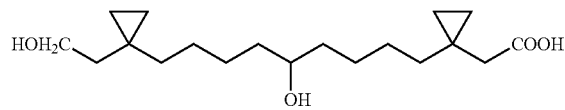

(1-{5-Hydroxy-9-[1-(2-hydroxy-ethyl)-cyclopropyl]-nonyl}-cyclopropyl)-acetic acid Compound 24

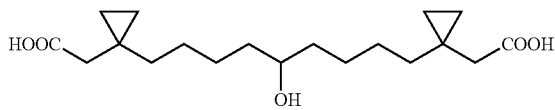

{1-[9-(1-Carboxymethyl-cyclopropyl)-5-hydroxy-nonyl]-cyclopropyl}-acetic acid

Compound 25

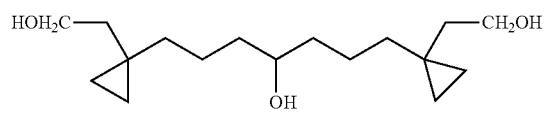

1,7-Bis-[1-(2-hydroxy-ethl)-cyclopropyl]-heptan-4-ol

Compound 26

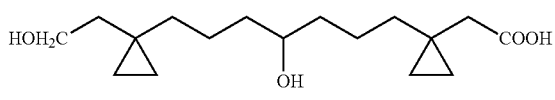

(1-{4-Hydroxy-7-[1-(2-hydroxy-ethyl)-cyclopropyl]-heptyl}-cyclopropyl)-acetic acid Compound 27

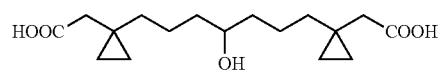

{1-[7-(1-Carboxymethyl-cyclopropyl)-4-hydroxy-heptyl]-cyclopropyl}-acetic acid

Compound 28

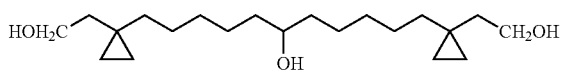

1,11-Bis-[1-2-hydroxy-ethyl)-cyclopropyl]-undecan-6-ol

Compound 29

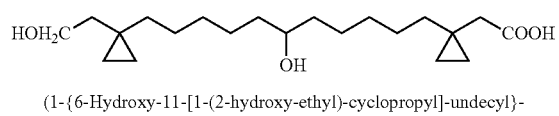

(1-{6-Hydroxy-11-[1-(2-hydroxy-ethyl)-cyclopropyl]-undecyl}-cyclopropyl)-acetic acid Compound 30

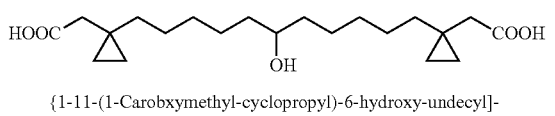

{1-11-(1-Carobxymethyl-cyclopropyl)-6-hydroxy-undecyl]-cyclopropyl}-acetic acid

Compound 31

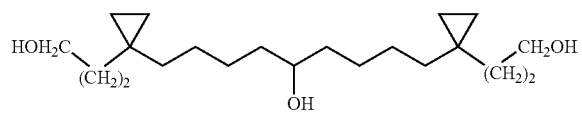

1,9-Bis-[1-(3-hydroxy-propyl)-cyclopropyl]-nonan-5-ol

Compound 32

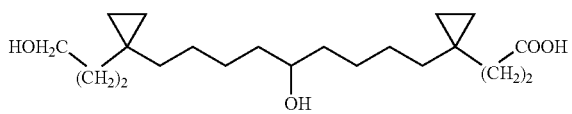

3-(1-{5-Hydroxy-9-[1-(3-hydroxy-propyl)-cyclopropyl]-nonyl}-cyclopropyl)-propionic acid Compound 33

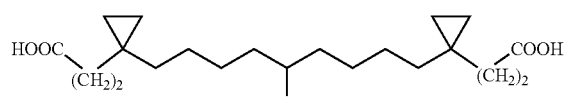

3-(1-{9-[1-(3-Carboxy-ethyl)-5-hydroxy-cyclopropyl]-nonyl}-cyclopropyl)-propionic acid Compound 34

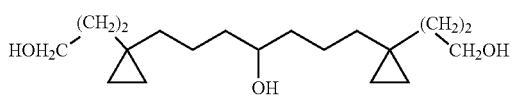

1,7-Bis-[1-(3-hydroxy-propyl)-cyclopropyl]-heptan-4-ol

Compound 35

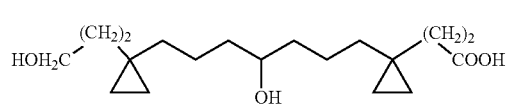

3-(1-{4-Hydroxy-7-[1-(3-hydroxy-propyl)-cyclopropyl]-heptyl}-cyclopropyl)-propionic acid Compound 36

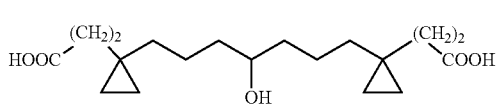

3-(1-{7-[1-(2-Carboxy-ethyl)-cyclopropyl]-4-hydroxy-heptyl}-cyclopropyl)-propionic acid -continued Compound 37

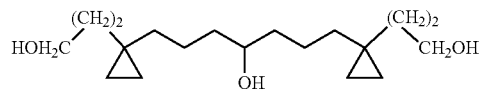

1,11-Bis-[1-(3-hydroxy-propyl)-cyclopropyl]-undecan-6-ol

Compound 38

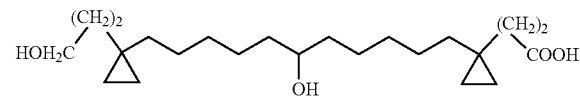

3-(1-{6-Hydroxy-11-[1-(3-hydroxy-propyl)-cyclopropyl]-undecyl}-cyclopropyl)-propionic acid Compound 39

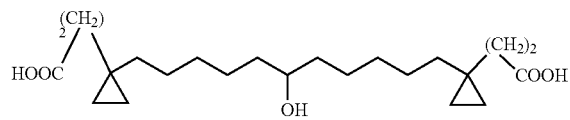

3-(1-{11-[1-(2-Carboxy-ethyl)-cyclopropyl]-6-hydroxy-undecyl}-cyclopropyl)-propionic acid Compound 40

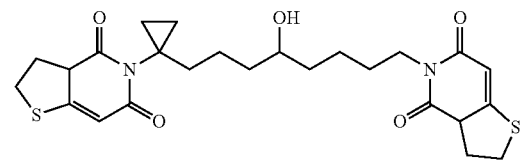

1,7-Bis-(4,6-dioxo-2,3,3a,6a-tetrahydro-4H-thieno[3,2-c]pyridin-5-yl)-1-(cyclopropyl)-6-hydroxy-heptane Compound 41

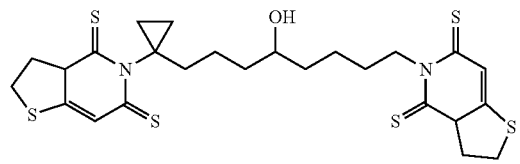

1,7-Bis-(4,6-dithioxo-2,3,3a,6-tetrahydro-4H-thieno[3,2-c]pyridin-5-yl)-1,7-bis-(cyclopropyl)-6-hydroxy-undecane Compound 42

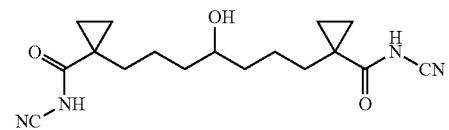

1,7-Bis-[1-dicyanimido-cyclopropyl]-4-hydroxy-heptane

Compound 43

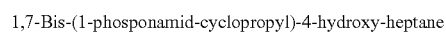

1,7-Bis-(1-phosponamid-cyclopropyl)-4-hydroxy-heptane

Compound 44

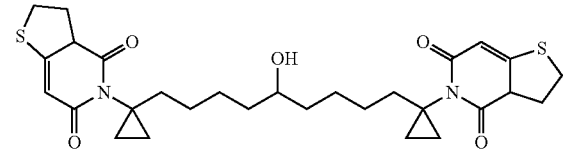

2,9-Bis-(4,6-dioxo-2,3,3a,6-tetrahydro-4H-thieno[3,2-c]pyridin-5-yl)-2,9-bis-(cyclopropyl)-5-hydroxy-nonane Compound 45

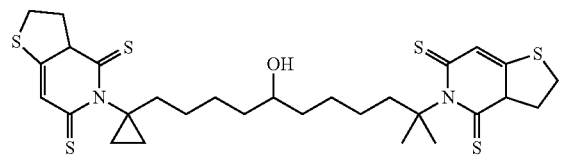

2,12-Bis-(4,6-dithioxo-2,3,3a,6-tetrahydro-4H-thieno[3,2-c]pyridin-5-yl)-2-methyl-12-(cyclopropyl)-7-hydroxy-dodecane Compound 46

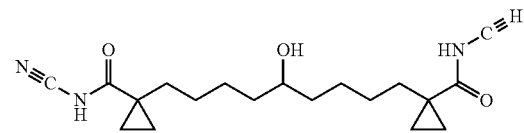

1,7-Bis-(1-dicyanimido-cyclopropyl)-5-hydroxy-nonane

Compound 47

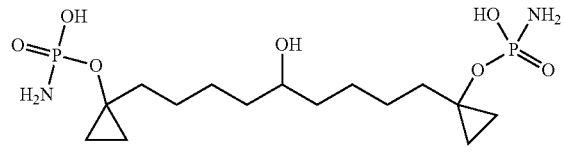

1,7-Bis-(1-phosphonamido-cyclopropyl)-5-hydroxy-nonane

Compound 48

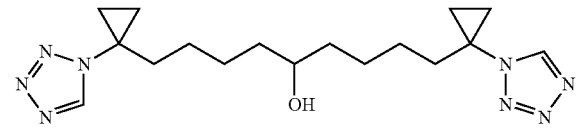

1,9-Bis-(1-tetrazol-1-yl-cyclopropyl)-nonan-5-ol

Compound 49

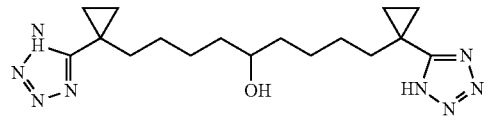

1,9-Bis-[1-(1H-tetrazol-5-yl)-cyclopropyl]-nonan-5-ol

Compound 50

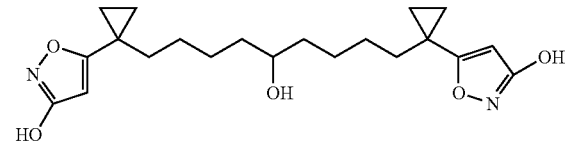

1,9-Bis-[1-(3-hydroxy-isoxazol-5-yl)-cyclopropyl]-nonan-5-ol

Compound 51

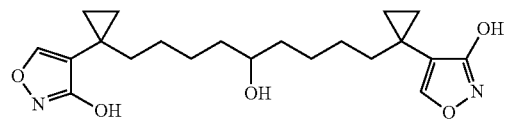

1,9-Bis-[1-(3-hydroxy-isoxazol-4-yl)-cyclopropyl]-nonan-5-ol

Compound 52

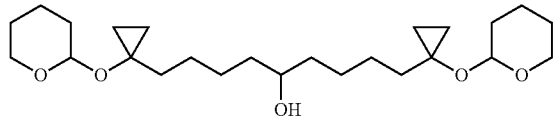

1,9-Bis-[1-tetrahydro-pyran-2-yloxy)-cyclopropyl]-nonan-5-ol

Compound 53

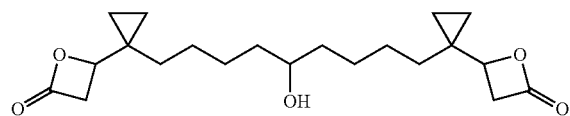

1,9-Bis-[1-(2-oxo-oxoethan-3-yl)-cyclopropyl]-nonan-5-ol

Compound 54

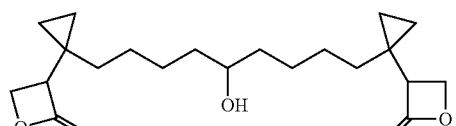

1,9-Bis-[1-(2-oxo-oxoethan-3-yl)-cyclopropyl]-nonan-5-ol

Compound 55

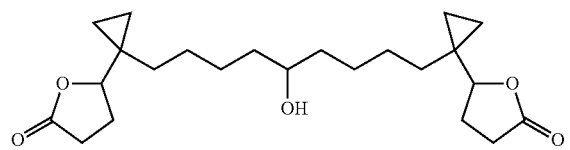

1,9-Bis-[1-(2-oxo-tetrahydrofuran-5-yl)-cyclopropyl]-nonan-5-ol

Compound 56

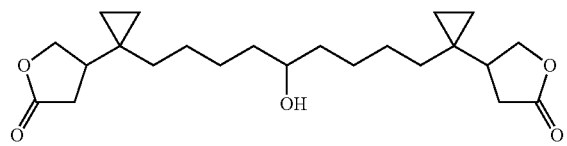

1,9-Bis-[1-(2-oxo-tetrahydrofuran-4-yl)-cyclopropyl]-nonan-5-ol

Compound 57

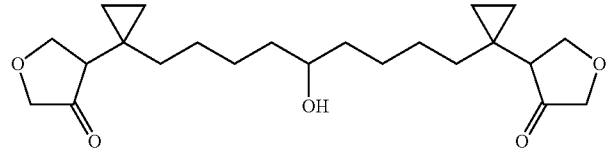

1,9-Bis-[1-(2-oxo-tetrahydrofuran-3-yl)-cyclopropyl]-nonan-5-ol

Compound 58

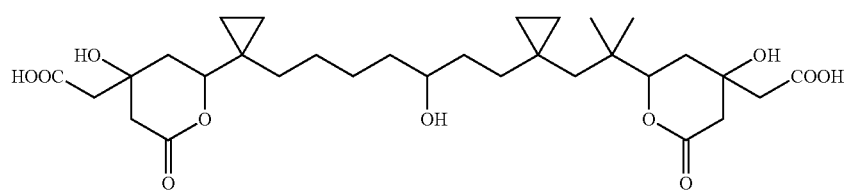

1,9-Bis{1-[9-(4-carboxymethyl-4-hydroxy-6-oxo-tetrahydro-pyran-2-yl)-(cyclopropyl)}-5-hydoxy-nonane Compound 59

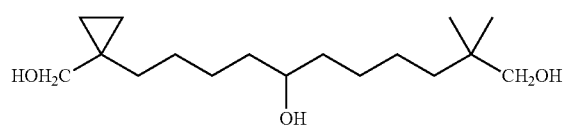

11-(1-Hydroxymethyl-cyclopropyl)-2,2-dimethyl-undecane-1,7-diol

Compound 60

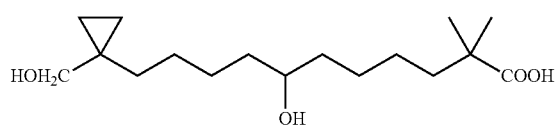

7-Hydroxy-11-(1-hydroxymethyl-cyclopropyl)-2,2-dimethyl-undecanoic acid

Compound 61

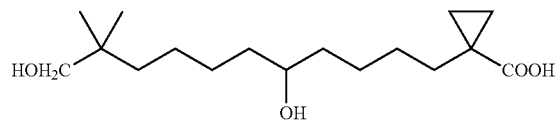

1-(5,11-Dihydroxy-10,10-dimethyl-undecyl)-cyclopropanecarboxylic acid

Compound 62

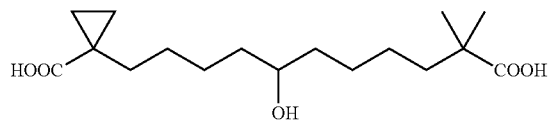

1-(10-Carboxy-5-hydroxy-10-methyl-undecyl)-cyclopropanecarboxylic acid

-continued

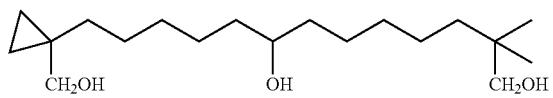

Compound 63

13-(1-Hydroxymethyl-cyclopropyl)-2,2-dimethyl-tridecane-1,8-diol

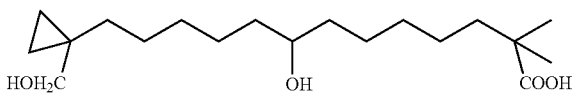

Compound 64

8-Hydroxy-13-(1-hydroxymethyl-cyclopropyl)-2,2-dimethyl-tridecanoic acid

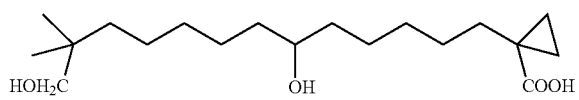

Compound 65

1-(6,13-Dihydroxy-12,12-dimethyl-tridecyl)-cyclopropanecarboxylic acid

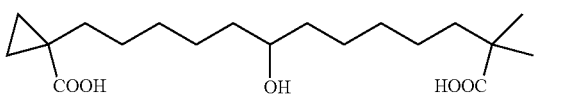

Compound 66

1-(12-Carboxy-6-hydroxy-12-methyl-tridecyl)-cyclopropanecarboxylic acid

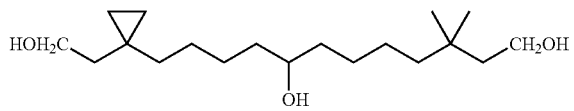

Compound 67

12-[1-(2-Hydroxy-ethyl)-cyclopropyl]-3,3-dimethyl-dodecane-1,8-diol

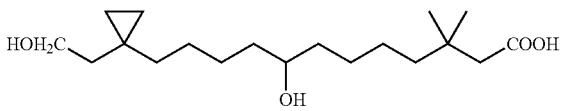

Compound 68

8-Hydroxy-12-[1-(2-hydroxy-ethyl)-cyclopropyl]-3,3-dimethyl-dodecanoic acid

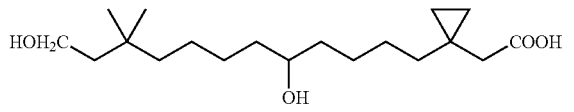

Compound 69

[1-(5,12-Dihydroxy-10,10-dimethyl-dodecyl)-cyclopropyl]-acetic acid

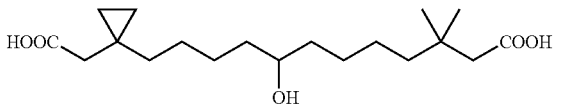

Compound 70

12-(1-Carboxymethyl-cyclopropyl)-8-hydroxy-3,3-dimethyl-dodecanoic acid

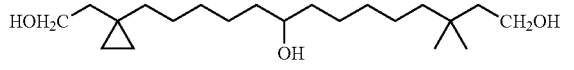

Compound 71

14-[1-(2-Hydroxy-ethyl)-cyclopropyl]-3,3-dimethyl-tetradecane-1,9-diol

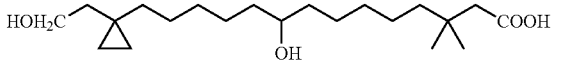

Compound 72

9-Hydroxy-14-[1-(2-hydroxy-ethyl)-cyclopropyl]-3,3-dimethyl-tetradecanoic acid

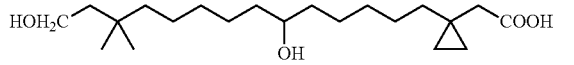

Compound 73

[1-(6,14-Dihydroxy-12,12-dimethyl-tetradecyl)-cyclopropyl]-acetic acid

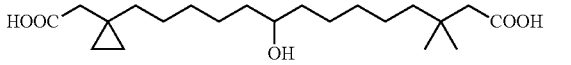

Compound 74

14-(1-Carboxymethyl-cyclopropyl)-9-hydroxy-3,3-dimethyl-tetradecanoic acid

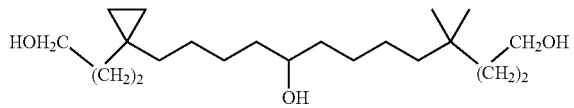

Compound 75

13-[1-(3-Hydroxy-propyl)-cyclopropyl]-4,4-dimethyl-tridecane-1,9-diol

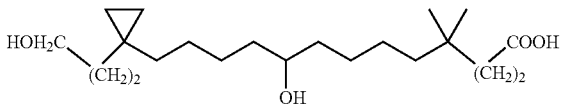

Compound 76

4,4-Dimethyl-9-hydroxy-13-[1-(3-hydroxypropyl)-cyclopropyl]-tridecanoic acid

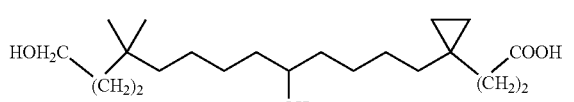

Compound 77

3-[1-(5,13-Dihydroxy-10,10-dimethyl-tridecyl)-cyclopropyl]-propionic acid

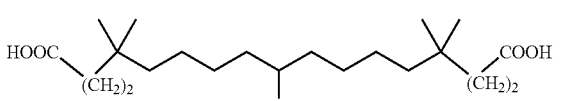

Compound 78

13-[1-(2-Carboxyethyl)-cyclopropyl]-9-hydroxy-4,4-dimethyl-tridecanoic acid

Compound 79

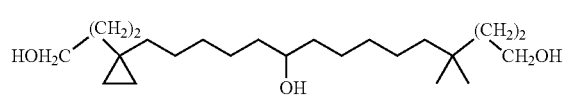

15-[1-(3-Hydroxy-propyl)-cyclopropyl]-4,4-dimethyl-pentadecane-1,10-diol

Compound 81

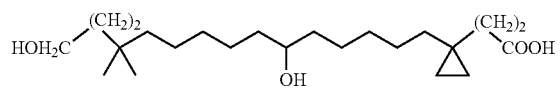

3-[1-(6,15-Dihydroxy-12,12-dimethyl-pentadecyl)-cyclopropyl]-propionic acid

Compound 83

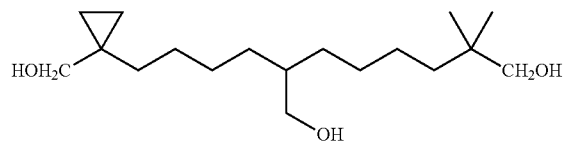

7-[4-(1-Hydroxymethyl-cyclopropyl)-butyl]2,2-dimethyl-octane-1,8-diol

Compound 85

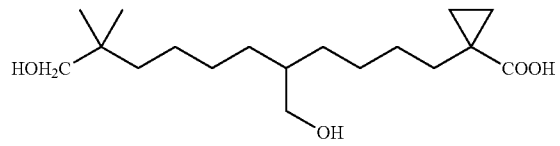

1-(11-Hydroxy-5-hydroxymethyl-10,10-dimethyl-undecyl)-cyclopropanecarboxylic acid Compound 87

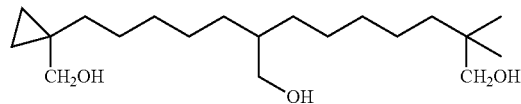

8-[5-(1-Hydroxymethyl-cyclopropyl)-pentyl]-2,2-dimethyl-nonane-1,9-diol

Compound 89

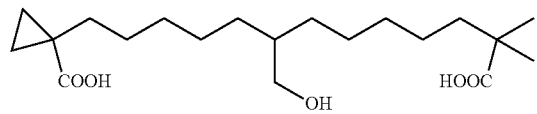

1-(12-Carboxy-6-hydroxymethyl-12-methyl-tridecyl)-cyclopropanecarboxylic acid

Compound 80

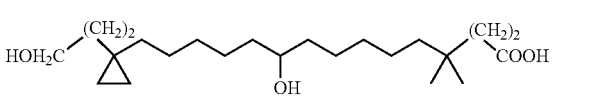

4,4-Dimethyl-10-hydroxy-15-[1-(3-hydroxy-propyl)-cyclopropyl]-pentadecanoic acid Compound 82

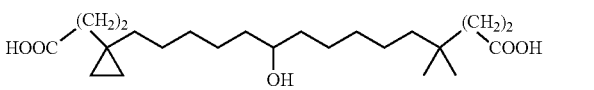

15;-[1-(2-Carboxyethyl)-cyclopropyl]-10-hydroxy-4,4-dimethyl-tridecanoic acid

Compound 84

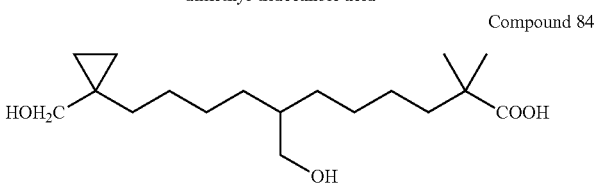

7-Hydroxymethyl-11-(1-hydroxymethyl-cyclopropyl)-2,2-dimethyl-undecanoic acid

Compound 86

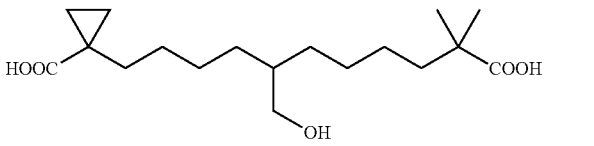

1-(1,0-Carboxy-5-hydroxymethyl-10-methyl-undecyl)-cyclopropanecarboxylic acid

Compound 88

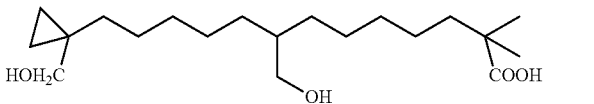

8-Hydroxymethyl-13-(1-hydroxymethyl-cyclopropyl)-2,2-dimethyl-tridecanoic acid

5.1 Synthesis of the Compounds of the Invention

The compounds of the invention can be obtained via the synthetic methodology illustrated in Scheme 1. Starting materials useful for preparing the compounds of the invention and intermediates thereof, are commercially available or can be prepared form commercially available materials using known synthetic methods and reagents.

Scheme 1 illustrates the synthesis of cycloalkyl-hydroxyl compounds of the formula 2 and 4 wherein n is an integer in the range from 2-12 and m is an integer in the range from 1-4.

Scheme 1: Synthesis of compounds of formula 2 and 4

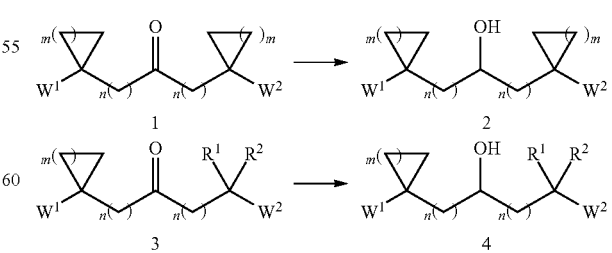

Compounds 1 and 3 are prepared as described in Dasseux et al. U.S. patent application Ser. No. 09/976,938, filed Oct. 11, 2001, which is incorporated herein by reference in its entirety. Compounds 2 and 4 are prepared from ketones of type 1 and 3, respectively by well-known reductive methods (see, Larock, R. C. *Comprehensive Organic Transformations; A Guide To Functional Group Preparations,* 1989, pp 527-548, for a discussion of various methods for conversion of ketones to alcohols see, March, J. *Advanced Organic Chemistry; Reactions, Mechanisms, and structure,* 4th ed., 1992, pp 910-918). For example, metalhydride reductions (e.g. lithium aluminum hydride, see Takazawa, O.; Kogami, K.; Hayashi, K., *Chem. Lett.,* 1983, 63-64, lithium tri-tert-butoxyaluminohydride, see Mander, L. N.; Palmer, L. T., *Aust. J. Chem.,* 1979, 32, 823-832 or sodium borohydride (Kishimoto, S.; et al., *Chem. Pharm. Bull.,* 1974, 22, 2231-2241, Mohr, P., *Tetrahedron Lett.,* 1995, 36, 7221-7224, Metzger, J. O.; Biermann, U., *Liebigs Ann. Chem.,* 1993, 6, 645-650, Kennedy, J.; et al., *J. Chem. Soc.,* 1961, 4945-4948)), catalytic hydrogenation catalyzed by transition metals (e.g. Raney nickel, see Zakharkin, L. I.; Guseva, V. V.; Churilova, I. M.; *J. Org. Chem. USSR,* 1983, 19, 1632-1634, platinum, see Ficini, J.; et al., *J. Am. Chem. Soc.,* 1974, 96, 1213-1214 or ruthenium, see Bowden, R. D.; Cooper, R. D. G.; Harris, C. J.; Moss, G. P.; Weedon, B. C. L.; Jackman, L. M., *J. Chem. Soc. Perkin Trans.* 1, 1983, 7, 1465-1474), metal or dissolving metal reductions (e.g. lithium, see Maiti, S. B.; Kundu, A. P.; Chatterjee, A.; Raychaudhuri, S. R., *Indian J. Chem. Sect. B,* 1986, 15-21) and reductions catalyzed by enzymes (e.g. Baker's yeast, see Utaka, M.; Watabu, H.; Takeda, A., *J. Org. Chem.,* 1987, 52, 4363-4368).

In a typical example, compound of formula 2 is prepared starting from the corresponding ketone 1 by treatment with lithium aluminum hydride (Takazawa, O.; Kogami, K.; Hayashi, K., *Chem. Lett.,* 1983, 63-64), lithium tri-tert-butoxyaluminohydride (Mander, L. N.; Palmer, L. T., *Aust. J. Chem.,* 1979, 32, 823-832), or preferably sodium borohydride (Kishimoto, S.; et al., Chem. Pharm. Bull., 1974, 22, 2231-2241, Mohr, P., Tetrahedron Lett., 1995, 36, 7221-7224, Metzger, J. O.; Biermann, U., *Liebigs Ann. Chem.,* 1993, 6, 645-650, Kennedy, J.; et al., *J. Chem. Soc.,* 1961, 4945-4948), preferably though not limited to temperatures between 0° C. and room temperature. Preferably though not limited, the reaction is run in a protic solvent where ethanol or isopropanol are the most preferred ones. Further, the reaction can be performed in the presence of a basic aqueous solution; preferably a solution of sodium hydroxide in water or a Lewis acid catalyst, preferably $CeCl_3$ (Gemal, A. L.; Luche, J.-L., *J. Am. Cem. Soc.,* 1981, 103, 5454, Cooley, G.; Kirk, D. N., *J. Chem. Soc. Perkin Trans. I,* 1984, 6, 1205-1212). Each of the references disclosed herein are incorporated by reference in their entirety.

5.2 Therapeutic Uses of Compounds or Compositions of the Invention

In accordance with the invention, a compound of the invention or a composition of the invention, comprising a compound of the invention and a pharmaceutically acceptable vehicle, is administered to a patient, preferably a human, with or at risk of aging, Alzheimer's Disease, cancer, cardiovascular disease, diabetic nephropathy, diabetic retinopathy, a disorder of glucose metabolism, dyslipidemia, dyslipoproteinemia, enhancing bile production, enhancing reverse lipid transport, hypertension, impotence, inflammation, insulin resistance, lipid elimination in bile, modulating C reactive protein, obesity, oxysterol elimination in bile, pancreatitis, Parkinson's disease, a peroxisome proliferator activated receptor-associated disorder, phospholipid elimination in bile, renal disease, septicemia, metabolic syndrome disorders (e.g., Syndrome X), a thrombotic disorder, gastrointestinal disease, irritable bowel syndrome (IBS), inflammatory bowel disease (e.g., Crohn's Disease, ulcerative colitis), arthritis (e.g., rheumatoid arthritis, osteoarthritis), autoimmune disease (e.g., systemic lupus erythematosus), scleroderma, ankylosing spondylitis, gout and pseudogout, muscle pain: polymyositis/polymyalgia rheumatica/fibrositis; infection and arthritis, juvenile rheumatoid arthritis, tendonitis, bursitis and other soft tissue rheumatism. In one embodiment, "treatment" or "treating" refers to an amelioration of a disease or disorder, or at least one discernible symptom thereof. In another embodiment, "treatment" or "treating" refers to inhibiting the progression of a disease or disorder, either physically, e.g., stabilization of a discernible symptom, physiologically, e.g., stabilization of a physical parameter, or both.

In certain embodiments, the compounds of the invention or the compositions of the invention are administered to a patient, preferably a human, as a preventative measure against such diseases. As used herein, "prevention" or "preventing" refers to a reduction of the risk of acquiring a given disease or disorder. In a preferred mode of the embodiment, the compositions of the present invention are administered as a preventative measure to a patient, preferably a human having a genetic predisposition to a aging, Alzheimer's Disease, cancer, cardiovascular disease, diabetic nephropathy, diabetic retinopathy, a disorder of glucose metabolism, dyslipidemia, dyslipoproteinemia, enhancing bile production, enhancing reverse lipid transport, hypertension, impotence, inflammation, insulin resistance, lipid elimination in bile, modulating C reactive protein, obesity, oxysterol elimination in bile, pancreatitis, Parkinson's disease, a peroxisome proliferator activated receptor-associated disorder, phospholipid elimination in bile, renal disease, septicemia, metabolic syndrome disorders (e.g., Syndrome X), a thrombotic disorder, inflammatory processes and diseases like gastrointestinal disease, irritable bowel syndrome (IBS), inflammatory bowel disease (e.g., Crohn's Disease, ulcerative colitis), arthritis (e.g., rheumatoid arthritis, osteoarthritis), autoimmune disease (e.g., systemic lupus erythematosus), scleroderma, ankylosing spondylitis, gout and pseudogout, muscle pain: polymyositis/polymyalgia rheumatica/fibrositis; infection and arthritis, juvenile rheumatoid arthritis, tendonitis, bursitis and other soft tissue rheumatism. Examples of such genetic predispositions include but are not limited to the ε4 allele of apolipoprotein E, which increases the likelihood of Alzheimer's Disease; a loss of function or null mutation in the lipoprotein lipase gene coding region or promoter (e.g., mutations in the coding regions resulting in the substitutions D9N and N291 S; for a review of genetic mutations in the lipoprotein lipase gene that increase the risk of cardiovascular diseases, dyslipidemias and dyslipoproteinemias, see Hayden and Ma, 1992, Mol. Cell. Biochem. 113:171-176); and familial combined hyperlipidemia and familial hypercholesterolemia.

In another preferred mode of the embodiment, the compounds of the invention or compositions of the invention are administered as a preventative measure to a patient having a non-genetic predisposition to a aging, Alzheimer's Disease, cancer, cardiovascular disease, diabetic nephropathy, diabetic retinopathy, a disorder of glucose metabolism, dyslipidemia, dyslipoproteinemia, enhancing bile production, enhancing reverse lipid transport, hypertension, impotence, inflammation, insulin resistance, lipid elimination in bile, modulating C reactive protein, obesity, oxysterol elimination in bile, pancreatitis, Parkinson's disease, a peroxisome proliferator activated receptor-associated disorder, phospholipid elimination in bile, renal disease, septicemia, metabolic syndrome disorders (e.g., Syndrome X), a thrombotic disorder, inflammatory processes and diseases like gastrointestinal disease, irritable bowel syndrome (IBS), inflammatory bowel disease (e.g., Crohn's Disease, ulcerative colitis), arthritis (e.g., rheumatoid arthritis, osteoarthritis), autoimmune disease (e.g., systemic lupus erythematosus), scleroderma, ankylosing spondylitis, gout and pseudogout, muscle pain: polymyositis/polymyalgia rheumatica/fibrositis; infection and arthritis, juvenile rheumatoid arthritis, tendonitis, bursitis and other soft tissue rheumatism. Examples of such non-genetic predispositions include but are not limited to cardiac bypass surgery and percutaneous transluminal coronary angioplasty, which often lead to restenosis, an accelerated form of atherosclerosis; diabetes in women, which often leads to polycystic ovarian disease; and cardiovascular disease, which often leads to impotence. Accordingly, the compositions of the invention may be used for the prevention of one disease or disorder and concurrently treating another (e.g., prevention of polycystic ovarian disease while treating diabetes; prevention of impotence while treating a cardiovascular disease).

5.2.1 Treatment of Cardiovascular Diseases

The present invention provides methods for the treatment or prevention of a cardiovascular disease, comprising administering to a patient a therapeutically effective amount of a compound or a composition comprising a compound of the invention and a pharmaceutically acceptable vehicle. As used herein, the term "cardiovascular diseases" refers to diseases of the heart and circulatory system. These diseases are often associated with dyslipoproteinemias and/or dyslipidemias. Cardiovascular diseases which the compositions of the present invention are useful for preventing or treating include but are not limited to arteriosclerosis; atherosclerosis; stroke; ischemia; endothelium dysfunctions, in particular those dysfunctions affecting blood vessel elasticity; peripheral vascular disease; coronary heart disease; myocardial infarcation; cerebral infarction and restenosis.

5.2.2 Treatment of Dyslipidemias

The present invention provides methods for the treatment or prevention of a dyslipidemia comprising administering to a patient a therapeutically effective amount of a compound or a composition comprising a compound of the invention and a pharmaceutically acceptable vehicle.

As used herein, the term "dyslipidemias" refers to disorders that lead to or are manifested by aberrant levels of circulating lipids. To the extent that levels of lipids in the blood are too high, the compositions of the invention are administered to a patient to restore normal levels. Normal levels of lipids are reported in medical treatises known to those of skill in the art. For example, recommended blood levels of LDL, HDL, free triglycerides and others parameters relating to lipid metabolism can be found at the web site of the American Heart Association and that of the National Cholesterol Education Program of the National Heart, Lung and Blood Institute (http://www.americanheart.org/cholesterol/about_level.html and http://www.nhlbi.nih.gov/health/public/heart/chol/hbc_what.html, respectively). At the present time, the recommended level of HDL cholesterol in the blood is above 35 mg/dL; the recommended level of LDL cholesterol in the blood is below 130 mg/dL; the recommended LDL:HDL cholesterol ratio in the blood is below 5:1, ideally 3.5:1; and the recommended level of free triglycerides in the blood is less than 200 mg/dL.

Dyslipidemias which the compositions of the present invention are useful for preventing or treating include but are not limited to hyperlipidemia and low blood levels of high density lipoprotein (HDL) cholesterol. In certain embodiments, the hyperlipidemia for prevention or treatment by the compounds of the present invention is familial hypercholesterolemia; familial combined hyperlipidemia; reduced or deficient lipoprotein lipase levels or activity, including reductions or deficiencies resulting from lipoprotein lipase mutations; hypertriglyceridemia; hypercholesterolemia; high blood levels of urea bodies (e.g. β-OH butyric acid); high blood levels of Lp(a) cholesterol; high blood levels of low density lipoprotein (LDL) cholesterol; high blood levels of very low density lipoprotein (VLDL) cholesterol and high blood levels of non-esterified fatty acids.

The present invention further provides methods for altering lipid metabolism in a patient, e.g., reducing LDL in the blood of a patient, reducing free triglycerides in the blood of a patient, increasing the ratio of HDL to LDL in the blood of a patient, and inhibiting saponified and/or non-saponified fatty acid synthesis, said methods comprising administering to the patient a compound or a composition comprising a compound of the invention in an amount effective alter lipid metabolism.

5.2.3 Treatment of Dyslipoproteinemias

The present invention provides methods for the treatment or prevention of a dyslipoproteinemia comprising administering to a patient a therapeutically effective amount of a compound or a composition comprising a compound of the invention and a pharmaceutically acceptable vehicle.

As used herein, the term "dyslipoproteinemias" refers to disorders that lead to or are manifested by aberrant levels of circulating lipoproteins. To the extent that levels of lipoproteins in the blood are too high, the compositions of the invention are administered to a patient to restore normal levels. Conversely, to the extent that levels of lipoproteins in the blood are too low, the compositions of the invention are administered to a patient to restore normal levels. Normal levels of lipoproteins are reported in medical treatises known to those of skill in the art.

Dyslipoproteinemias which the compositions of the present invention are useful for preventing or treating include but are not limited to high blood levels of LDL; high blood levels of apolipoprotein B (apo B); high blood levels of Lp(a); high blood levels of apo(a); high blood levels of VLDL; low blood levels of HDL; reduced or deficient lipoprotein lipase levels or activity, including reductions or deficiencies resulting from lipoprotein lipase mutations; hypoalphalipoproteinemia; lipoprotein abnormalities associated with diabetes; lipoprotein abnormalities associated with obesity; lipoprotein abnormalities associated with Alzheimer's Disease; and familial combined hyperlipidemia.

The present invention further provides methods for reducing apo C-II levels in the blood of a patient; reducing apo C-III levels in the blood of a patient; elevating the levels of HDL associated proteins, including but not limited to apo A-I, apo A-II, apo A-N and apo E in the blood of a patient; elevating the levels of apo E in the blood of a patient, and promoting clearance of triglycerides from the blood of a patient, said methods comprising administering to the patient a compound or a composition comprising a compound of the invention in an amount effective to bring about said reduction, elevation or promotion, respectively.

5.2.4 Treatment of Glucose Metabolism Disorders

The present invention provides methods for the treatment or prevention of a glucose metabolism disorder, comprising administering to a patient a therapeutically effective amount of a compound or a composition comprising a compound of the invention and a pharmaceutically acceptable vehicle. As used herein, the term "glucose metabolism disorders" refers to disorders that lead to or are manifested by aberrant glucose storage and/or utilization. To the extent that indicia of glucose metabolism (i.e., blood insulin, blood glucose) are too high, the compositions of the invention are administered to a patient to restore normal levels. Conversely, to the extent that indicia of glucose metabolism are too low, the compositions of the invention are administered to a patient to restore normal levels. Normal indicia of glucose metabolism are reported in medical treatises known to those of skill in the art.

Glucose metabolism disorders which the compositions of the present invention are useful for preventing or treating include but are not limited to impaired glucose tolerance; insulin resistance; insulin resistance related breast, colon or prostate cancer; diabetes, including but not limited to non-insulin dependent diabetes mellitus (NIDDM), insulin dependent diabetes mellitus (IDDM), gestational diabetes mellitus (GDM), and maturity onset diabetes of the young (MODY); pancreatitis; hypertension; polycystic ovarian disease; and high levels of blood insulin and/or glucose.

The present invention further provides methods for altering glucose metabolism in a patient, for example to increase insulin sensitivity and/or oxygen consumption of a patient, said methods comprising administering to the patient a compound or a composition comprising a compound of the invention in an amount effective to alter glucose metabolism.

5.2.5 Treatment of PPAR-Associated Disorders

The present invention provides methods for the treatment or prevention of a PPAR-associated disorder, comprising administering to a patient a therapeutically effective amount of a compound or a composition comprising a compound of the invention and a pharmaceutically acceptable vehicle. As used herein, "treatment or prevention of PPAR associated disorders" encompasses treatment or prevention of rheumatoid arthritis; multiple sclerosis; psoriasis; inflammatory bowel diseases; breast; colon or prostate cancer; low levels of blood HDL; low levels of blood, lymph and/or cerebrospinal fluid apo E; low blood, lymph and/or cerebrospinal fluid levels of apo A-I; high levels of blood VLDL; high levels of blood LDL; high levels of blood triglyceride; high levels of blood apo B; high levels of blood apo C-III and reduced ratio of post-heparin hepatic lipase to lipoprotein lipase activity. HDL may be elevated in lymph and/or cerebral fluid.

5.2.6 Treatment of Renal Diseases

The present invention provides methods for the treatment or prevention of a renal disease, comprising administering to a patient a therapeutically effective amount of a compound or a composition comprising a compound of the invention and a pharmaceutically acceptable vehicle. Renal diseases that can be treated by the compounds of the present invention include glomerular diseases (including but not limited to acute and chronic glomerulonephritis, rapidly progressive glomerulonephritis, nephrotic syndrome, focal proliferative glomerulonephritis, glomerular lesions associated with systemic disease, such as systemic lupus erythematosus, Goodpasture's syndrome, multiple myeloma, diabetes, neoplasia, sickle cell disease, and chronic inflammatory diseases), tubular diseases (including but not limited to acute tubular necrosis and acute renal failure, polycystic renal diseasemedullary sponge kidney, medullary cystic disease, nephrogenic diabetes, and renal tubular acidosis), tubulointerstitial diseases (including but not limited to pyelonephritis, drug and toxin induced tubulointerstitial nephritis, hypercalcemic nephropathy, and hypokalemic nephropathy) acute and rapidly progressive renal failure, chronic renal failure, nephrolithiasis, or tumors (including but not limited to renal cell carcinoma and nephroblastoma). In a most preferred embodiment, renal diseases that are treated by the compounds of the present invention are vascular diseases, including but not limited to hypertension, nephrosclerosis, microangiopathic hemolytic anemia, atheroembolic renal disease, diffuse cortical necrosis, and renal infarcts.

5.2.7 Treatment of Cancer

The present invention provides methods for the treatment or prevention of cancer, comprising administering to a patient a therapeutically effective amount of a compound or a composition comprising a compound of the invention and a pharmaceutically acceptable vehicle. Types of cancer that can be treated using a Compound of the Invention include, but are not limited to, those listed in Table 2.

TABLE 2

| Solid tumors, including but not limited to |
|---|
| fibrosarcoma |
| myxosarcoma |
| liposarcoma |
| chondrosarcoma |
| osteogenic sarcoma |
| chordoma |
| angiosarcoma |
| endotheliosarcoma |
| lymphangiosarcoma |
| lymphangioendotheliosarcoma |
| synovioma |
| mesothelioma |
| Ewing's tumor |
| leiomyosarcoma |
| rhabdomyosarcoma |
| colon cancer |
| colorectal cancer |
| kidney cancer |
| pancreatic cancer |
| bone cancer |
| breast cancer |
| ovarian cancer |
| prostate cancer |
| esophogeal cancer |
| stomach cancer |
| oral cancer |
| nasal cancer |
| throat cancer |
| squamous cell carcinoma |
| basal cell carcinoma |
| adenocarcinoma |
| sweat gland carcinoma |
| sebaceous gland carcinoma |
| papillary carcinoma |
| papillary adenocarcinomas |
| cystadenocarcinoma |
| medullary carcinoma |
| bronchogenic carcinoma |
| renal cell carcinoma |
| hepatoma |
| bile duct carcinoma |
| choriocarcinoma |
| seminoma |
| embryonal carcinoma |
| Wilms' tumor |
| cervical cancer |
| uterine cancer |
| testicular cancer |
| small cell lung carcinoma |

TABLE 2-continued bladder carcinoma
lung cancer
epithelial carcinoma
glioma
glioblastoma multiforme
astrocytoma
medulloblastoma
craniopharyngioma
ependymoma
pinealoma
hemangioblastoma
acoustic neuroma
oligodendroglioma
meningioma
skin cancer
melanoma
neuroblastoma
retinoblastoma
Blood-borne cancers, including but not limited to:

acute lymphoblastic B-cell leukemia
acute lymphoblastic T-cell leukemia
acute myeloblastic leukemia "AML"
acute promyelocytic leukemia "APL"
acute monoblastic leukemia
acute erythroleukemic leukemia
acute megakaryoblastic leukemia
acute myelomonocytic leukemia
acute nonlymphocytic leukemia
acute undifferentiated leukemia
chronic myelocytic leukemia "CML"
chronic lymphocytic leukemia "CLL"
hairy cell leukemia
multiple myeloma
Acute and chronic leukemias Lymphoblastic
myelogenous
lymphocytic
myelocytic leukemias
Lymphomas:

Hodgkin's disease
non-Hodgkin's Lymphoma
Multiple myeloma
Waldenström's macroglobulinemia
Heavy chain disease
Polycythemia vera Cancer, including, but not limited to, a tumor, metastasis, or any disease or disorder characterized by uncontrolled cell growth, can be treated or prevented by administration of a Compound of the Invention.

5.2.8 Treatment of Other Diseases

The present invention provides methods for the treatment or prevention of Alzheimer's Disease, Syndrome X, septicemia, thrombotic disorders, obesity, pancreatitis, hypertension, inflammation, and impotence, comprising administering to a patient a therapeutically effective amount of a compound or a composition comprising a compound of the invention and a pharmaceutically acceptable vehicle.

As used herein, "treatment or prevention of Alzheimer's Disease" encompasses treatment or prevention of lipoprotein abnormalities associated with Alzheimer's Disease.

As used herein, "treatment or prevention of Syndrome X or Metabolic Syndrome" encompasses treatment or prevention of a symptom thereof, including but not limited to impaired glucose tolerance, hypertension and dyslipidemia/dyslipoproteinemia.

As used herein, "treatment or prevention of septicemia" encompasses treatment or prevention of septic shock.

As used herein, "treatment or prevention of thrombotic disorders" encompasses treatment or prevention of high blood levels of fibrinogen and promotion of fibrinolysis.

In addition to treating or preventing obesity, the compositions of the invention can be administered to an individual to promote weight reduction of the individual.

As used herein, "treatment or prevention of diabetic nephropathy" encompasses treating or preventing kidney disease that develops as a result of diabetes mellitus (DM). Diabetes mellitus is a disorder in which the body is unable to metabolize carbohydrates (e.g., food starches, sugars, cellulose) properly. The disease is characterized by excessive amounts of sugar in the blood (hyperglycemia) and urine; inadequate production and/or utilization of insulin; and by thirst, hunger, and loss of weight. Thus, the compounds of the invention can also be used to treat or prevent diabetes mellitus.

As used herein, "treatment or prevention of diabetic retinopathy" encompasses treating or preventing complications of diabetes that lead to or cause blindness. Diabetic retinopathy occurs when diabetes damages the tiny blood vessels inside the retina, the light-sensitive tissue at the back of the eye.

As used herein, "treatment or prevention of impotence" includes treating or preventing erectile dysfunction, which encompasses the repeated inability to get or keep an erection firm enough for sexual intercourse. The word "impotence" may also be used to describe other problems that interfere with sexual intercourse and reproduction, such as lack of sexual desire and problems with ejaculation or orgasm. The term "treatment or prevention of impotence includes, but is not limited to impotence that results as a result of damage to nerves, arteries, smooth muscles, and fibrous tissues, or as a result of disease, such as, but not limited to, diabetes, kidney disease, chronic alcoholism, multiple sclerosis, atherosclerosis, vascular disease, and neurologic disease.

As used herein, "treatment or prevention of hypertension" encompasses treating or preventing blood flow through the vessels at a greater than normal force, which strains the heart; harms the arteries; and increases the risk of heart attack, stroke, and kidney problems. The term hypertension includes, but is not limited to, cardiovascular disease, essential hypertension, hyperpiesia, hyperpiesis, malignant hypertension, secondary hypertension, or white-coat hypertension.

As used herein, "treatment or prevention of inflammation" encompasses treating or preventing inflammation diseases including, but not limited to, chronic inflammatory disorders of the joints including arthritis, e.g., rheumatoid arthritis and osteoarthritis; respiratory distress syndrome, inflammatory bowel diseases such as ileitis, ulcerative colitis and Crohn's disease; and inflammatory lung disorders such as asthma and chronic obstructive airway disease, inflammatory disorders of the eye such as corneal dystrophy, trachoma, onchocerciasis, uveitis, sympathetic ophthalmitis, and endophthalmitis; inflammatory disorders of the gum, e.g., periodontitis and gingivitis; tuberculosis; leprosy; inflammatory diseases of the kidney including glomerulonephritis and nephrosis; inflammatory disorders of the skin including acne, sclerodermatitis, psoriasis, eczema, photoaging and wrinkles; inflammatory diseases of the central nervous system, including AIDS-related neurodegeneration, stroke, neurotrauma, Alzheimer's disease, encephalomyelitis and viral or autoimmune encephalitis; autoimmune diseases including immune-complex vasculitis, systemic lupus and erythematodes; systemic lupus erythematosus (SLE); and inflammatory diseases of the heart such as cardiomyopathy.

5.3 Combination Therapy

In certain embodiments of the present invention, the compounds and compositions of the invention can be used in combination therapy with at least one other therapeutic agent.

The compound of the invention and the therapeutic agent can act additively or, more preferably, synergistically. In a preferred embodiment, a compound or a composition comprising a compound of the invention is administered concurrently with the administration of another therapeutic agent, which can be part of the same composition as the compound of the invention or a different composition. In another embodiment, a compound or a composition comprising a compound of the invention is administered prior or subsequent to administration of another therapeutic agent. As many of the disorders for which the compounds and compositions of the invention are useful in treating are chronic disorders, in one embodiment combination therapy involves alternating between administering a compound or a composition comprising a compound of the invention and a composition comprising another therapeutic agent, e.g., to minimize the toxicity associated with a particular drug. The duration of administration of each drug or therapeutic agent can be, e.g., one month, three months, six months, or a year. In certain embodiments, when a composition of the invention is administered concurrently with another therapeutic agent that potentially produces adverse side effects including but not limited to toxicity, the therapeutic agent can advantageously be administered at a dose that falls below the threshold at which the adverse side is elicited.

The present compositions can be administered together with a statin. Statins for use in combination with the compounds and compositions of the invention include but are not limited to atorvastatin, pravastatin, fluvastatin, lovastatin, simvastatin, and cerivastatin.

The present compositions can also be administered together with a PPAR agonist, for example a thiazolidinedione or a fibrate. Thiazolidinediones for use in combination with the compounds and compositions of the invention include but are not limited to 5 ((4 (2 (methyl 2 pyridinylamino)ethoxy)phenyl)methyl) 2,4 thiazolidinedione, troglitazone, pioglitazone, ciglitazone, WAY 120,744, englitazone, AD 5075, darglitazone, and rosiglitazone. Fibrates for use in combination with the compounds and compositions of the invention include but are not limited to gemfibrozil, fenofibrate, clofibrate, or ciprofibrate. As mentioned previously, a therapeutically effective amount of a fibrate or thiazolidinedione often has toxic side effects. Accordingly, in a preferred embodiment of the present invention, when a composition of the invention is administered in combination with a PPAR agonist, the dosage of the PPAR agonist is below that which is accompanied by toxic side effects.

The present compositions can also be administered together with a bile acid binding resin. Bile acid binding resins for use in combination with the compounds and compositions of the invention include but are not limited to cholestyramine and colestipol hydrochloride. The present compositions can also be administered together with niacin or nicotinic acid. The present compositions can also be administered together with a RXR agonist. RXR agonists for use in combination with the compounds of the invention include but are not limited to LG 100268, LGD 1069, 9-cis retinoic acid, 2 (1 (3,5,5,8,8 pentamethyl 5,6,7,8 tetrahydro 2 naphthyl) cyclopropyl)pyridine 5 carboxylic acid, or 4 ((3,5,5,8,8 pentamethyl 5,6,7,8 tetrahydro 2 naphthyl)$_2$ carbonyl)benzoic acid. The present compositions can also be administered together with an anti-obesity drug. Anti-obesity drugs for use in combination with the compounds of the invention include but are not limited to β-adrenergic receptor agonists, preferably β-3 receptor agonists, fenfluramine, dexfenfluramine, sibutramine, bupropion, fluoxetine, and phentermine. The present compositions can also be administered together with a hormone. Hormones for use in combination with the compounds of the invention include but are not limited to thyroid hormone, estrogen and insulin. Preferred insulins include but are not limited to injectable insulin, transdermal insulin, inhaled insulin, or any combination thereof. As an alternative to insulin, an insulin derivative, secretagogue, sensitizer or mimetic may be used. Insulin secretagogues for use in combination with the compounds of the invention include but are not limited to forskolin, dibutryl cAMP or isobutylmethylxanthine (IBMX).

The present compositions can also be administered together with a phosphodiesterase type 5 ("PDE5") inhibitor to treat or prevent disorders, such as but not limited to, impotence. In a particular, embodiment the combination is a synergistic combination of a composition of the invention and a PDE5 inhibitor.

The present compositions can also be administered together with a tyrophostine or an analog thereof. Tyrophostines for use in combination with the compounds of the invention include but are not limited to tryophostine 51.

The present compositions can also be administered together with sulfonylurea-based drugs. Sulfonylurea-based drugs for use in combination with the compounds of the invention include, but are not limited to, glisoxepid, glyburide, acetohexamide, chlorpropamide, glibornuride, tolbutamide, tolazamide, glipizide, gliclazide, gliquidone, glyhexamide, phenbutamide, and tolcyclamide. The present compositions can also be administered together with a biguanide. Biguanides for use in combination with the compounds of the invention include but are not limited to metformin, phenformin and buformin.

The present compositions can also be administered together with an α-glucosidase inhibitor. α-glucosidase inhibitors for use in combination with the compounds of the invention include but are not limited to acarbose and miglitol.

The present compositions can also be administered together with an apo A-I agonist. In one embodiment, the apo A-I agonist is the Milano form of apo A-I (apo A-IM). In a preferred mode of the embodiment, the apo A-IM for administration in conjunction with the compounds of the invention is produced by the method of U.S. Pat. No. 5,721,114 to Abrahamsen. In a more preferred embodiment, the apo A-I agonist is a peptide agonist. In a preferred mode of the embodiment, the apo A-I peptide agonist for administration in conjunction with the compounds of the invention is a peptide of U.S. Pat. No. 6,004,925 or 6,037,323 to Dasseux.

The present compositions can also be administered together with apolipoprotein E (apo E). In a preferred mode of the embodiment, the apoE for administration in conjunction with the compounds of the invention is produced by the method of U.S. Pat. No. 5,834,596 to Ageland.

In yet other embodiments, the present compositions can be administered together with an HDL-raising drug; an HDL enhancer; or a regulator of the apolipoprotein A-I, apolipoprotein A-IV and/or apolipoprotein genes.

In one embodiment, the other therapeutic agent can be an antiemetic agent. Suitable antiemetic agents include, but are not limited to, metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine and tropisetron.

In another embodiment, the other therapeutic agent can be an hematopoietic colony stimulating factor. Suitable hematopoietic colony stimulating factors include, but are not limited to, filgrastim, sargramostim, molgramostim and erythropoietin alfa.

In still another embodiment, the other therapeutic agent can be an opioid or non-opioid analgesic agent. Suitable opioid analgesic agents include, but are not limited to, morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone and propoxyphene. Suitable non-opioid analgesic agents include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam and sulindac.

5.3.1 Combination Therapy of Cardiovascular Diseases

The present compositions can be administered together with a known cardiovascular drug. Cardiovascular drugs for use in combination with the compounds of the invention to prevent or treat cardiovascular diseases include but are not limited to peripheral antiadrenergic drugs, centrally acting antihypertensive drugs (e.g., methyldopa, methyldopa HCl), antihypertensive direct vasodilators (e.g., diazoxide, hydralazine HCl), drugs affecting renin-angiotensin system, peripheral vasodilators, phentolamine, antianginal drugs, cardiac glycosides, inodilators (e.g., aminone, milrinone, enoximone, fenoximone, imazodan, sulmazole), antidysrhythmic drugs, calcium entry blockers, ranitine, bosentan, and rezulin.

5.3.2 Combination Therapy of Cancer

The present invention includes methods for treating cancer, comprising administering to an animal in need thereof an effective amount of a Compound of the Invention and another therapeutic agent that is an anti-cancer agent. Suitable anti-cancer agents include, but are not limited to, those listed in Table 3.

TABLE 3

| Alkylating agents | |
|---|---|
| Nitrogen mustards: | Cyclophosphamide |
| | Ifosfamide |
| | trofosfamide |
| | Chlorambucil |
| | Treos |
| Nitrosoureas: | carbustine (BCNU) |
| | Lomustine (CCNU) |
| Alkylsulphonates | Busulfan |
| | Treosulfan |
| Triazenes: | Dacarbazine |
| Platinum containing compounds: | Cisplatin |
| | carboplatin |
| Plant Alkaloids | |
| Vinca alkaloids: | Vicristine |
| | Vinblastine |
| | Vindesine |
| | Vinorelbine |
| Taxoids: | paclitaxel |
| | Docetaxol |

TABLE 3-continued

| DNA Topoisomerase Inhibitors | |
|---|---|
| Epipodophyllins: | Etoposide |
| | Teniposide |
| | Topotecan |
| | 9-aminocamptothecin |
| | camptothecin |
| | crisnatol |
| mitomycins: | Mitomycin C |
| Anti-metabolites | |
| Anti-folates: | |
| DHFR inhibitors: | METHOTREXATE |
| | Trimetrexate |
| IMP dehydrogenase Inhibitors: | Mycophenolic acid |
| | Tiazofurin |
| | Ribavirin |
| | EICAR |
| Ribonuclotide reductase Inhibitors: | Hydroxyurea |
| | deferoxamine |
| Pyrimidine analogs: | |
| Uracil analogs | 5-Fluorouracil |
| | Floxuridine |
| | Doxifluridine |
| | Ratitrexed |
| Cytosine analogs | cytarabine (ara C) |
| | Cytosine arabinoside |
| | fludarabine |
| Purine analogs: | mercaptopurine |
| | Thioguanine |
| Hormonal therapies: | |
| Receptor antagonists: | |
| Anti-estrogen | Tamoxifen |
| | Raloxifene |
| | megestrol |
| | goscrclin |
| | Leuprolide acetate |
| LHRH agonists: | flutamide |
| | bicalutamide |
| Retinoids/Deltoids | |
| Vitamin D3 analogs: | EB 1089 |
| | CB 1093 |
| | KH 1060 |
| Photodynamic therapies: | vertoporfin (BPD-MA) |
| | Phthalocyanine |
| | photosensitizer Pc4 |
| | Demethoxy-hypocrellin A |
| | (2BA-2-DMHA) |
| Cytokines: | Interferon-α |
| | Interferon-γ |
| | Tumor necrosis factor |
| Others: | |
| Isoprenylation inhibitors: | Lovastatin |
| Dopaminergic neurotoxins: | 1-methyl-4-phenylpyridinium ion |
| Cell cycle inhibitors: | staurosporine |
| Actinomycines: | Actinomycin D |
| | Dactinomycin |
| Bleomycins: | bleomycin A2 |
| | Bleomycin B2 |
| | Peplomycin |
| Anthracyclines: | daunorubicin |
| | Doxorubicin (adriamycin) |
| | Idarubicin |
| | Epirubicin |
| | Pirarubicin |
| | Zorubicin |
| | Mitoxantrone |
| MDR inhibitors | verapamil |
| $Ca^{2+}$ ATPase inhibitors: | thapsigargin |

In a specific embodiment, a composition of the invention further comprises one or more chemotherapeutic agents and/or is administered concurrently with radiation therapy. In another specific embodiment, chemotherapy or radiation therapy is administered prior or subsequent to administration of a present composition, preferably at least an hour, five hours, 12 hours, a day, a week, a month, more preferably several months (e.g., up to three months), subsequent to administration of a composition of the invention.

In other embodiments, the invention provides methods for treating or preventing cancer, comprising administering to an animal in need thereof an effective amount of a Compound of the Invention and a chemotherapeutic agent. In one embodiment the chemotherapeutic agent is that with which treatment of the cancer has not been found to be refractory. In another embodiment, the chemotherapeutic agent is that with which the treatment of cancer has been found to be refractory. The Compounds of the Invention can be administered to an animal that has also undergone surgery as treatment for the cancer.

In one embodiment, the additional method of treatment is radiation therapy.

In a specific embodiment, the Compound of the Invention is administered concurrently with the chemotherapeutic agent or with radiation therapy. In another specific embodiment, the chemotherapeutic agent or radiation therapy is administered prior or subsequent to administration of a Compound of the Invention, preferably at least an hour, five hours, 12 hours, a day, a week, a month, more preferably several months (e.g., up to three months), prior or subsequent to administration of a Compound of the Invention.

A chemotherapeutic agent can be administered over a series of sessions, any one or a combination of the chemotherapeutic agents listed in Table 3 can be administered. With respect to radiation, any radiation therapy protocol can be used depending upon the type of cancer to be treated. For example, but not by way of limitation, x-ray radiation can be administered; in particular, high-energy megavoltage (radiation of greater that 1 MeV energy) can be used for deep tumors, and electron beam and orthovoltage x-ray radiation can be used for skin cancers. Gamma-ray emitting radioisotopes, such as radioactive isotopes of radium, cobalt and other elements, can also be administered.

Additionally, the invention provides methods of treatment of cancer with a Compound of the Invention as an alternative to chemotherapy or radiation therapy where the chemotherapy or the radiation therapy has proven or can prove too toxic, e.g., results in unacceptable or unbearable side effects, for the subject being treated. The animal being treated can, optionally, be treated with another cancer treatment such as surgery, radiation therapy or chemotherapy, depending on which treatment is found to be acceptable or bearable.

The Compounds of the Invention can also be used in an in vitro or ex vivo fashion, such as for the treatment of certain cancers, including, but not limited to leukemias and lymphomas, such treatment involving autologous stem cell transplants. This can involve a multi-step process in which the animal's autologous hematopoietic stem cells are harvested and purged of all cancer cells, the patient's remaining bone-marrow cell population is then eradicated via the administration of a high dose of a Compound of the Invention with or without accompanying high dose radiation therapy, and the stem cell graft is infused back into the animal. Supportive care is then provided while bone marrow function is restored and the animal recovers.

5.4 Surgical Uses

Cardiovascular diseases such as atherosclerosis often require surgical procedures such as angioplasty. Angioplasty is often accompanied by the placement of a reinforcing a metallic tube shaped structure known as a "stent" into a damaged coronary artery. For more serious conditions, open heart surgery such as coronary bypass surgery may be required. These surgical procedures entail using invasive surgical devices and/or implants, and are associated with a high risk of restenosis and thrombosis. Accordingly, the compounds and compositions of the invention may be used as coatings on surgical devices (e.g., catheters) and implants (e.g., stents) to reduce the risk of restenosis and thrombosis associated with invasive procedures used in the treatment of cardiovascular diseases.

5.5 Veterinary and Livestock Uses

A composition of the invention can be administered to a non-human animal for a veterinary use for treating or preventing a disease or disorder disclosed herein.

In a specific embodiment, the non-human animal is a household pet. In another specific embodiment, the non-human animal is a livestock animal. In a preferred embodiment, the non-human animal is a mammal, most preferably a cow, horse, sheep, pig, cat, dog, mouse, rat, rabbit, or guinea pig. In another preferred embodiment, the non-human animal is a fowl species, most preferably a chicken, turkey, duck, goose, or quail.

In addition to veterinary uses, the compounds and compositions of the invention can be used to reduce the fat content of livestock to produce leaner meats. Alternatively, the compounds and compositions of the invention can be used to reduce the cholesterol content of eggs by administering the compounds to a chicken, quail, or duck hen. For non-human animal uses, the compounds and compositions of the invention can be administered via the animals' feed or orally as a drench composition.

5.6 Therapeutic/Prophylactic Administration and Compositions

Due to the activity of the compounds and compositions of the invention, they are useful in veterinary and human medicine. As described above, the compounds and compositions of the invention are useful for the treatment or prevention of aging, Alzheimer's Disease, cancer, cardiovascular disease, diabetic nephropathy, diabetic retinopathy, a disorder of glucose metabolism, dyslipidemia, dyslipoproteinemia, hypertension, impotence, inflammation, insulin resistance, lipid elimination in bile, modulating C reactive protein, obesity, oxysterol elimination in bile, pancreatitis, Parkinson's disease, a peroxisome proliferator activated receptor-associated disorder, phospholipid elimination in bile, renal disease, septicemia, metabolic syndrome disorders (e.g., Syndrome X), a thrombotic disorder, enhancing bile production, enhancing reverse lipid transport, inflammatory processes and diseases like gastrointestinal disease, irritable bowel syndrome (IBS), inflammatory bowel disease (e.g., Crohn's Disease, ulcerative colitis), arthritis (e.g., rheumatoid arthritis, osteoarthritis), autoimmune disease (e.g., systemic lupus erythematosus), scleroderma, ankylosing spondylitis, gout and pseudogout, muscle pain: polymyositis/polymyalgia rheumatica/fibrositis; infection and arthritis, juvenile rheumatoid arthritis, tendonitis, bursitis and other soft tissue rheumatism.

The invention provides methods of treatment and prophylaxis by administration to a patient of a therapeutically effective amount of a compound or a composition comprising a compound of the invention. The patient is an animal, including, but not limited, to an animal such a cow, horse, sheep, pig, chicken, turkey, quail, cat, dog, mouse, rat, rabbit, guinea pig, etc., and is more preferably a mammal, and most preferably a human.

The compounds and compositions of the invention, are preferably administered orally. The compounds and compositions of the invention may also be administered by any other convenient route, for example, by intravenous infusion or bolus injection, by absorption through epithelial or mucocutaneous linings (e.g., oral mucosa, rectal and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer a compound of the invention. In certain embodiments, more than one compound of the invention is administered to a patient. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The preferred mode of administration is left to the discretion of the practitioner, and will depend in-part upon the site of the medical condition. In most instances, administration will result in the release of the compounds of the invention into the bloodstream.

In specific embodiments, it may be desirable to administer one or more compounds of the invention locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of an atherosclerotic plaque tissue.

In certain embodiments, for example, for the treatment of Alzheimer's Disease, it may be desirable to introduce one or more compounds of the invention into the central nervous system by any suitable route, including intraventricular, intrathecal and epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds of the invention can be formulated as a suppository, with traditional binders and vehicles such as triglycerides.

In another embodiment, the compounds and compositions of the invention can be delivered in a vesicle, in particular a liposome (see Langer, 1990, Science 249:1527 1533; Treat et al., in Liposomes in the Therapy of Infectious Disease and Cancer, Lopez-Berestein and Fidler (eds.), Liss, New York, pp. 353 365 (1989); Lopez Berestein, ibid., pp. 317 327; see generally ibid.).

In yet another embodiment, the compounds and compositions of the invention can be delivered in a controlled release system. In one embodiment, a pump may be used (see Langer, supra; Sefton, 1987, CRC Crit. Ref. Biomed. Eng. 14:201; Buchwald et al., 1980, Surgery 88:507 Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled-release system can be placed in proximity of the target area to be treated, e.g., the liver, thus requiring only a fraction of the systemic dose (see, e.g., Goodson, in Medical Applications of Controlled Release, supra, vol. 2, pp. 115 138 (1984)). Other controlled-release systems discussed in the review by Langer, 1990, Science 249:1527 1533) may be used.

The present compositions will contain a therapeutically effective amount of a compound of the invention, optionally more than one compound of the invention, preferably in purified form, together with a suitable amount of a pharmaceutically acceptable vehicle so as to provide the form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the compounds and compositions of the invention and pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in "Remington's Pharmaceutical Sciences" by E.W. Martin.

In a preferred embodiment, the compounds and compositions of the invention are formulated in accordance with routine procedures as a pharmaceutical composition adapted for intravenous administration to human beings. Typically, compounds and compositions of the invention for intravenous administration are solutions in sterile isotonic aqueous buffer. Where necessary, the compositions may also include a solubilizing agent. Compositions for intravenous administration may optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound of the invention is to be administered by intravenous infusion, it can be dispensed, for example, with an infusion bottle containing sterile pharmaceutical grade water or saline. Where the compound of the invention is administered by injection, an ampoule of sterile water for injection or saline can be provided so that the ingredients may be mixed prior to administration.

Compounds and compositions of the invention for oral delivery may be in the form of tablets, lozenges, aqueous or oily suspensions, granules, powders, emulsions, capsules, syrups, or elixirs. Compounds and compositions of the invention for oral delivery can also be formulated in foods and food mixes. Orally administered compositions may contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds and compositions of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

The amount of a compound of the invention that will be effective in the treatment of a particular disorder or condition disclosed herein will depend on the nature of the disorder or condition, and can be determined by standard clinical techniques. In addition, in vitro or in vivo assays may optionally be employed to help identify optimal dosage ranges. The precise dose to be employed in the compositions will also depend on the route of administration, and the seriousness of the disease or disorder, and should be decided according to the judgment of the practitioner and each patient's circumstances. However, suitable dosage ranges for oral administration are generally about 0.001 milligram to 2000 milligrams of a compound of the invention per kilogram body weight. In specific preferred embodiments of the invention, the oral dose is 0.01 milligram to 1000 milligrams per kilogram body weight, more preferably 0.1 milligram to 100 milligrams per kilogram body weight, more preferably 0.5 milligram to 25 milligrams per kilogram body weight, and yet more preferably 1 milligram to 10 milligrams per kilogram body weight. In a most preferred embodiment, the oral dose is 5 milligrams of a compound of the invention per kilogram body weight.

The dosage amounts described herein refer to total amounts administered; that is, if more than one compound of the invention is administered, the preferred dosages correspond to the total amount of the compounds of the invention administered. Oral compositions preferably contain 10% to 95% active ingredient by weight.

Suitable dosage ranges for intravenous (i.v.) administration are 0.01 milligram to 1000 milligrams per kilogram body weight, 0.1 milligram to 350 milligrams per kilogram body weight, and 1 milligram to 100 milligrams per kilogram body weight. Suitable dosage ranges for intranasal administration are generally about 0.01 pg/kg body weight to 1 mg/kg body weight. Suppositories generally contain 0.01 milligram to 50 milligrams of a compound of the invention per kilogram body weight and comprise active ingredient in the range of 0.5% to 10% by weight. Recommended dosages for intradermal, intramuscular, intraperitoneal, subcutaneous, epidural, sublingual, intracerebral, intravaginal, transdermal administration or administration by inhalation are in the range of 0.001 milligram to 200 milligrams per kilogram of body weight. Suitable doses of the compounds of the invention for topical administration are in the range of 0.001 milligram to 1 milligram, depending on the area to which the compound is administered. Effective doses may be extrapolated from dose-response curves derived from in vitro or animal model test systems. Such animal models and systems are well known in the art.

The invention also provides pharmaceutical packs or kits comprising one or more containers filled with one or more compounds of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In a certain embodiment, the kit contains more than one compound of the invention. In another embodiment, the kit comprises a compound of the invention and another lipid-mediating compound, including but not limited to a statin, a thiazolidinedione, or a fibrate.

The compounds of the invention are preferably assayed in vitro and in vivo, for the desired therapeutic or prophylactic activity, prior to use in humans. For example, in vitro assays can be used to determine whether administration of a specific compound of the invention or a combination of compounds of the invention is preferred for lowering fatty acid synthesis. The compounds and compositions of the invention may also be demonstrated to be effective and safe using animal model systems.

Other methods will be known to the skilled artisan and are within the scope of the invention.

The following examples are provided by way of illustration and not limitation.

6. SYNTHETIC EXAMPLES

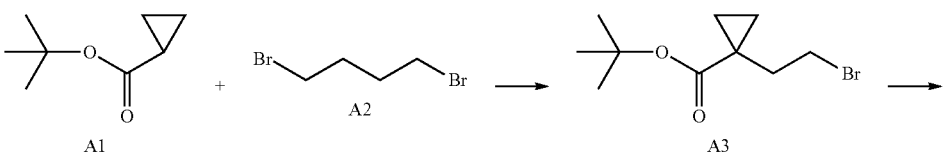

-continued

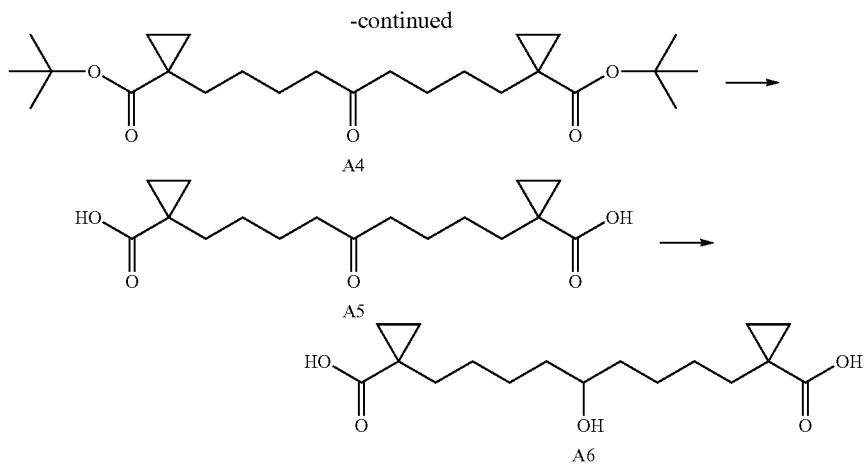

6.1 Tert-Butyl 1-(4-bromo-butyl)-cyclopropanecarboxylate

Under a $N_2$ atmosphere at −60° C., a solution of tert-butyl cyclopropanecarboxylate (80.05 g, 0.507 mol) and 1,4-dibromobutane (219.3 g, 1.01 mol) in dry THF (800 mL) was added drop wise to a solution of LDA (2 M in THF/heptane/ethylbenzene, 380 mL, 0.76 mol) in 1.5 h. Stirring was continued for 5 h, during which the reaction mixture was allowed to slowly reach rt. After that, the reaction mixture was poured into saturated aqueous $NH_4Cl$ (1 L). The organic layer was separated and concentrated in vacuo to a smaller volume. The aqueous layer was extracted with $Et_2O$ (3×200 mL). The combined organic layers were washed with saturated aqueous $NH_4Cl$ (2×400 mL) and brine (400 mL), dried ($Na_2SO_4$) and evaporated in vacuo. The remaining residue was purified by fractional distillation under reduced pressure to give tert-Butyl 1-(4-bromo-butyl)-cyclopropanecarboxylate (51.4 g, 94% pure by GC, 34%) as a slightly yellow oil. bp: T=93-96° C. (p=0.075-0.087 Torr), $^1$HNMR ($CDCl_3$): δ=3.40 (t, J=6.8 Hz, 2H), 1.85 (quintet, J=7.1 Hz, 2H), 1.65-1.46 (m, 4H), 1.43 (s, 9H), 1.12 (q, J=3.5 Hz, 2H), 0.60 (q, J=3.5 Hz, 2H). $^{13}$C NMR ($CDCl_3$): δ=174.0, 79.8, 33.6, 33.2, 32.8, 27.9 (3×), 26.3, 23.9, 15.1 (2×). HRMS calcd for $C_{12}H_2$:$BrO_2$ (MH$^+$): 277.0803, found: 277.0807.

6.2 Tert-butyl 1-[9-[1-(tert-butoxycarbonyl)cyclopropyl]-5-oxononyl]-1-cyclopropanecarboxylate Under a $N_2$ atmosphere, NaH (60% (w/w) in mineral oil, 2.91 g, 72.8 mmol) was added portion wise to a solution of TosMIC (5.85 g, 30.0 mmol) and $Bu_4NI$ (1.10 g, 2.98 mmol) in dry DMSO (100 mL) while stirring vigorously and cooling with a water bath. After 10 min, tert-Butyl 1-(4-bromo-butyl)-cyclopropanecarboxylate (16.56 g, 94% pure by GC, 56.2 mmol) was added drop wise in 20 min and stirring was continued for 1 h and 50 min. Then, $H_2O$ (100 mL) was added drop wise and the resulting mixture was extracted with $Et_2O$ (3×100 mL). The combined organic layers were washed with brine (2×100 mL), dried ($Na_2SO_4$) and evaporated in vacuo. The remaining oil was purified by column chromatography (silica, heptane:EtOAc=6:1) to give tert-butyl 1-{9-[1-(tert-butoxycarbonyl)cyclopropyl]-5-isocyano-5-[(4-methylphenyl)sulfonyl]nonyl}-1-cyclopropanecarboxylate (10.00 g) as a slightly yellow oil. The above mentioned oil (10.00 g) was dissolved in $CH_2Cl_2$ (200 mL) and conc aqueous HCl (4 mL) was added. After stirring vigorously for 1 h, $H_2O$ (100 mL) was added and the layers were separated. The aqueous phase was extracted with $CH_2Cl_2$ (100 mL) and the combined organic layers were washed with saturated aqueous $NaHCO_3$ (3×100 mL), dried ($Na_2SO_4$) and evaporated in vacuo. The remaining residue was purified by column chromatography (silica, heptane:EtOAc=10:1) to give tert-butyl 1-[9-[1-(tert-butoxycarbonyl)cyclopropyl]-5-oxononyl]-1-cyclopropanecarboxylate (5.80 g, 49%) as a colorless oil. $^1$H NMR ($CDCl_3$): δ=2.39 (t, J=7.3 Hz, 4H), 1.63-1.38 (m, 30H), 1.10 (dd, J=6.6, 3.9 Hz, 4H), 0.59 (dd, J=6.7, 3.9 Hz, 4H). $^{13}$C NMR ($CDCl_3$): δ=211.1, 174.4 (2×), 79.9 (2×), 42.7 (2×), 33.9 (2×), 28.0 (6×), 27.4 (2×), 24.1 (2×), 24.0 (2×), 15.2 (4×). HRMS calcd for $C_{25}H_{43}O_5$ (MH$^+$): 423.3111, found: 423.3111.

6.3 1-[9-(1-Carboxycyclopropyl)-5-oxononyl]-1-cyclopropanecarboxylic acid

A solution of tert-butyl 1-[9-[1-(tert-butoxycarbonyl)cyclopropyl]-5-oxononyl]-1-cyclopropanecarboxylate (5.31 g, 12.6 mmol) in $HCO_2H$ (50 mL) was stirred for 3 h, evaporated in vacuo and coevaporated from toluene (3×25 mL) to give 1-[9-(1-carboxycyclopropyl)-5-oxononyl]-1-cyclopropanecarboxylic acid (3.89 g, 99%) as a white solid. An analytical sample was obtained after recrystallization from $iPr_2O$/heptane. mp: 132-134° C. $^1$H NMR ($CD_3OD$): δ=2.45 (t, J=6.9 Hz, 4H), 1.58-1.39 (m, 12H), 1.14 (dd, J=6.6, 3.7 Hz, 4H), 0.70 (dd, J=6.8, 3.9 Hz, 4H). $^{13}$C NMR ($CD_3OD$): δ=214.4, 179.4 (2×), 43.5 (2×), 34.9 (2×), 28.5 (2×), 25.1 (2×), 24.2 (2×), 16.2 (4×). Anal. calcd for $C_{17}H_{26}O_5$: C, 65.78; H, 8.44, found: C, 65.40; H, 8.37.

6.4 1-[9-(1-Carboxycyclopropyl)-5-hydroxynonyl]-1-cyclopropanecarboxylic acid To a suspension of 1-[9-(1-carboxycyclopropyl)-5-oxononyl]-1-cyclopropanecarboxylic acid (6.95 g, 22.4 mmol) in iPrOH (40 mL) and $H_2O$ (40 mL) was added NaOH (1.80 g, 45.0 mmol). After 30 min of stirring, $NaBH_4$ (0.45 g, 11.8 mmol) was added to the resulting clear solution. After 3 h and 15 min, the mixture was acidified to pH~1 with aqueous HCl (1M) and extracted with $Et_2O$ (3×100 mL). The combined organic phases were dried ($Na_2SO_4$) and evaporated in vacuo to give 1-[9-(1-carboxycyclopropyl)-5-hydroxynonyl]-1-cyclopropanecarboxylic acid (6.02 g, 86%) as a slightly yellow oil. $^1$H NMR ($CD_3OD$): δ=3.49 (br s, 1H), 1.57-1.25 (m, 16H), 1.14 (dd, J=3.6, 6.3, 4H), 0.70 (dd, J=3.3, 6.3, 4H). $^{13}$C NMR ($CD_3OD$): δ=178.9 (2×), 72.2, 38.4 (2×), 35.1 (2×), 28.9 (2×), 27.0 (2×), 24.3 (2×), 16.3 (2×), 16.2 (2×).

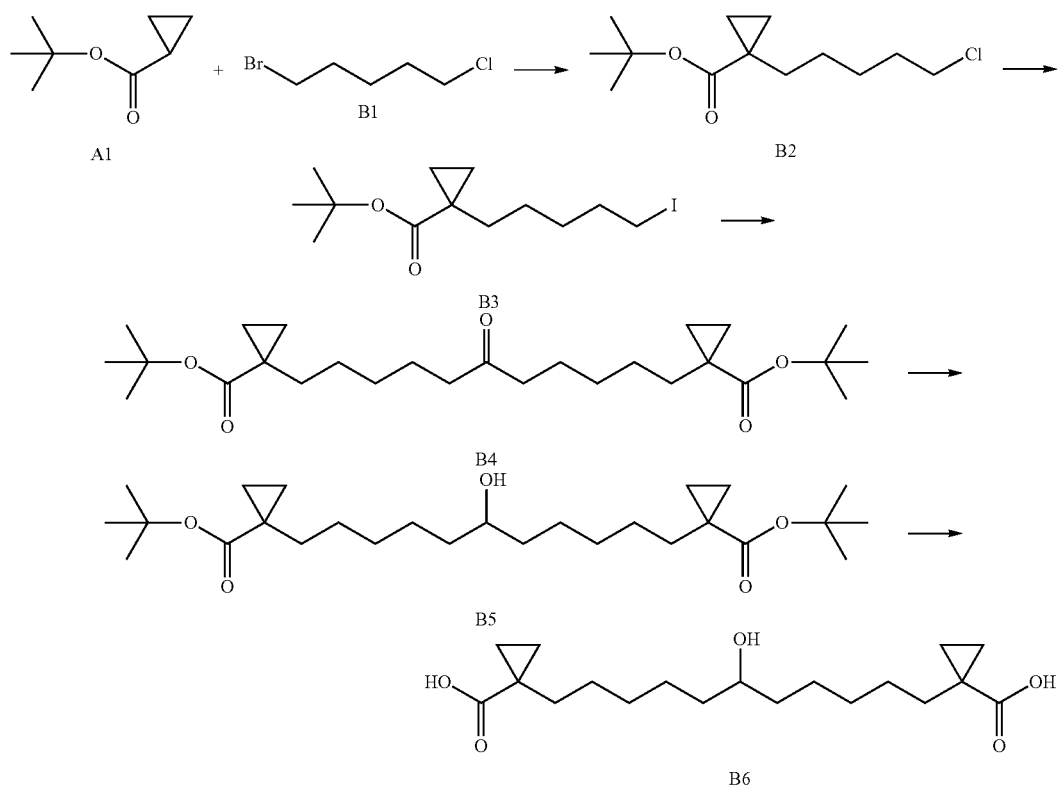

6.5 Tert-butyl 1-(5-chloropentyl)-1-cyclopropanecarboxylate

Under an Ar atmosphere at 0° C., BuLi (2.5M in hexanes, 80 mL, 0.20 mol) was added dropwise to a solution of iPr$_2$NH (27.2 mL, 194 mmol, distilled from NaOH) in dry THF (200 mL) in 30 min. The reaction mixture was stirred for 30 min, cooled to −70° C. and then, tert-butyl cyclopropanecarboxylate (prepared according to Kohlrausch, K. W. F.; Skrabal, R., Z. *Elektrochem. Angew. Phys. Chem.*, 1937, 43, 282-285, 25.0 g, 176 mmol) was added dropwise in 30 min. The resultant mixture was allowed to warm up to −35° C., cooled again to −70° C. and then 1-bromo-5-chloropentane (36 mL, 50.7 g, 273 mmol) was added dropwise in 15 min. The reaction mixture was allowed to reach −5° C., stirred for 3 h, poured into a mixture of ice (100 mL), H$_2$O (100 mL), brine (200 mL) and aqueous HCl (2M, 200 mL) and extracted with Et$_2$O (2×300 mL). The combined organic layers were washed with a mixture of brine and saturated aqueous NaHCO$_3$ (10:1, 300 mL), dried (Na$_2$SO$_4$) and evaporated in vacuo. The remaining oil was purified by fractional distillation under reduced pressure to give tert-butyl 1-(5-chloropentyl)-1-cyclopropanecarboxylate (31.5 g 73%) as a colorless liquid. bp: T=67-74° C. (p=0.001 mbar). $^1$H NMR (CDCl$_3$): δ=3.52 (t, J=6.6 Hz, 2H), 1.77 (quintet, J=6.8 Hz, 2H), 1.48-1.38 (m, 6H), 1.42 (s, 9H), 1.10 (dd, J=6.5 Hz, 3.8 Hz, 2H), 0.59 (dd, J=6.6, 3.9 Hz, 2H). $^{13}$C NMR (CDCl$_3$): δ=174.1, 79.9, 45.2, 34.2, 32.7, 28.2 (3×), 27.20, 27.17, 24.3, 15.4 (2×). HRMS calcd for C$_{13}$H$_{24}$ClO$_2$ (MH$^+$): 247.1465, found: 247.1465.

6.6 Tert-butyl 1-(5-iodopentyl)-1-cyclopropanecarboxylate

To a solution of tert-butyl 1-(5-chloropentyl)-1-cyclopropanecarboxylate (31.5 g, 128 mmol) in 2-butanone (150 mL) was added NaI (24.9 g, 166 mmol). The reaction mixture was stirred under reflux for 24 h, diluted with heptane (220 mL) and filtered through a layer of silica (~2 cm) in a glassfilter. The residue was eluted with a mixture of heptane and EtOAc (3:1, 5×100 mL). The combined filtrate and elutes were evaporated in vacuo to give tert-butyl 1-(5-iodopentyl)-1-cyclopropanecarboxylate (42.3 g, 99%) as a slightly yellow liquid. $^1$H NMR (CDCl$_3$): δ=3.18 (t, J=7.1 Hz, 2H), 1.82 (quintet, J=7.1 Hz, 2H), 1.48-1.33 (m, 6H), 1.42 (s, 9H), 1.10 (dd, J=6.8 Hz, Hz, 2H), 0.58 (dd, J=6.6, 3.9 Hz, 2H). $^{13}$C NMR (CDCl$_3$): δ=174.0, 79.9, 34.1, 33.6, 30.8, 28.2 (3×), 26.8, 24.3, 15.4 (2×), 7.4. HRMS calcd for C$_{13}$H$_{23}$IO$_2$ (M$^+$): 338.0743, found: 338.0743.

6.7 Tert-butyl 1-11-[1-(tert-butoxycarbonyl)cyclopropyl]-6-oxoundecyl-1-cyclopropyanecarboxylate Under a N$_2$ atmosphere at 0° C., KOtBu (8.35 g, 74.6 mmol) was added to a solution of TosMIC (13.84 g, 70.9 mmol) in DMAc (100 mL). Then tert-butyl 1-(5-iodopentyl)-1-cyclopropanecarboxylate (24.0 g, 71.0 mmol) was added dropwise in 15 min and the reaction mixture was allowed to warm to rt, stirred for 0.5 h and cooled again to 0° C. Another portion of KOtBu (8.35 g, 74.6 mmol) and tert-butyl 1-(5-iodopentyl)-1-cyclopropanecarboxylate (24 g, 71 mmol, in 15 min) were added and the resultant mixture was allowed to warm to rt. After 2 h, the reaction mixture was poured into an ice/H$_2$O (300 mL) mixture and extracted with Et$_2$O (3×150 mL). To the combined organic layers was added EtOAc (100 mL) and the resultant solution was washed with a mixture of brine (100 mL), H$_2$O (100 mL) and aqueous Na$_2$SO$_3$ (10%, 50 mL), dried (Na$_2$SO$_4$) and evaporated in vacuo. The remaining residue was taken up in EtOAc (100 mL) and filtered through a layer of silica in a glassfilter (elute: heptane:

EtOAc=1:1, 5×80 mL). The combined filtrate and washings were evaporated in vacuo. The remaining oil was dissolved in CH$_2$Cl$_2$ (400 mL) and conc aqueous HCl (11.4 mL) was added. After 0.5 h, the reaction mixture was treated with saturated aqueous NaHCO$_3$ (250 mL) and stirred for 0.5 h. The layers were separated and the aqueous phase was extracted with CH$_2$Cl$_2$ (200 mL). The combined organic layers were dried (Na$_2$SO$_4$) and evaporated in vacuo. The remaining residue was dissolved in heptane and set aside for 3 d upon which precipitation occurred. The residue was separated by decantation and washed with heptane (3×75 mL). The combined heptane layers were evaporated in vacuo and the resultant oil was purified by column chromatography (silica, heptane:EtOAc=12:1) to give tert-butyl 1-11-[1-(tert-butoxycarbonyl)cyclopropyl]-6-oxoundecyl-1-cyclopropanecarboxylate (16.3 g, >90% pure by $^1$H NMR, 46%) as a colorless oil. $^1$H NMR (CDCl$_3$): δ=2.37 (t, J=7.4 Hz, 4H), 1.62-1.49 (quintet, J=7.4 Hz, 4H), 1.48-1.36 (m, 8H), 1.41 (s, 18H), 1.33-1.20 (m, 4H) 1.09 (dd, J=6.5, 3.8 Hz, 4H), 0.58 (dd, J=6.6, 3.9 Hz, 4H). $^{13}$C NMR (CDCl$_3$): δ=210.9, 174.1 (2×), 79.8 (2×), 42.9 (2×), 34.1 (2×), 29.6 (2×), 28.2 (6×), 27.7 (2×), 24.4 (2×), 24.0 (2×), 15.4 (4×). HRMS calcd for C$_{27}$H$_{46}$O$_5$Na (MNa$^+$): 473.3243, found 473.3233.

6.8 Tert-butyl 1-11-[1-(tert-butoxycarbonyl)cyclopropyl]-6-hydroxyundecyl-1-cyclopropanecarboxylate A solution of tert-butyl 1-11-[1-(tert-butoxycarbonyl)cyclopropyl]-6-oxoundecyl-1-cyclopropanecarboxylate (7.87 g, 17.4 mmol) in EtOH (40 mL) was treated portion wise with NaBH$_4$ (0.726 g, 19.2 mmol) in ~2 min at 0° C. The reaction mixture was stirred at it for 1.5 h, and then poured into a mixture of H$_2$O and ice (200 mL). The resultant mixture was extracted with Et$_2$O (2×200 mL), and the combined organic layers were dried (Na$_2$SO$_4$) and concentrated in vacuo. The remaining residue was purified by column chromatography (silica, heptane:EtOAc=8:1) to give tert-butyl 1-11-[1-(tert-butoxycarbonyl)cyclopropyl]-6-hydroxyundecyl-1-cyclopropanecarboxylate (7.00 g, 89%) as a colorless oil. $^1$H NMR (CDCl$_3$) δ=3.61-3.51 (m, 1H), 1.49-1.21 (m, 39H) 1.09 (dd, J=6.5, 3.8 Hz, 4H), 0.58 (dd, J=6.5, 3.8 Hz, 4H). $^{13}$C NMR (CDCl$_3$) δ=174.2 (2×), 79.7 (2×), 71.9, 37.6 (2×), 34.2 (2×), 30.0 (2×), 28.2 (6×), 27.9 (2×), 25.8 (2×), 24.4 (2×), 15.4 (2×), 15.3 (2×). HRMS calcd for C$_{27}$H$_{49}$O$_5$ (M+H)$^+$: 453.3580, found 453.3550.

6.9 1-[11-(1-Carboxycyclopropyl)-6-hydroxyundecyl]-1-cyclopropanecarboxylic acid A solution of tert-butyl 1-11-[1-(tert-butoxycarbonyl)cyclopropyl]-6-hydroxyundecyl-1-cyclopropanecarboxylate (6.49 g, 14.4 mmol) in 1,4-dioxane (70 mL) was treated with conc HCl (70 mL) and stirred overnight. Then the mixture was treated with a mixture of ice and H$_2$O (1:1, 300 mL), and extracted with EtOAc (3×100 mL). The combined organic layers were washed with brine (3×100 mL), dried (Na$_2$SO$_4$), and concentrated in vacuo. The remaining oil was coevaporated in vacuo from toluene (2×50 mL), CH$_2$Cl$_2$ (50 mL) and Et$_2$O (3×50 mL), and finally further concentrated in vacuo at 65° C. for 3 h, to give 1-[11-(1-carboxycyclopropyl)-6-hydroxyundecyl]-1-cyclopropane-carboxylic acid (5.08 g, 100%) as a slightly yellow oil, contaminated with Et$_2$O (4% (w/w)) and toluene (0.5% (w/w)). The thick oil started to crystallize spontaneously after 10 d, after which H$_2$O (100 mL) was added. The resulting mixture was left standing for 3 d, and the so obtained crystalline material was filtered and air dried to give 1-[11-(1-carboxycyclopropyl)-6-hydroxyundecyl]-1-cyclopropanecarboxylic acid (4.64 g, 95%) as colorless crystals. mp: 87-91° C. $^1$H NMR (CDCl$_3$) δ=5.50 (br s, 3H), 3.58, (br s, 1H), 1.53-1.22 (m, 20H) 1.25 (dd, J=6.6, 3.9 Hz, 4H), 0.74 (dd, J=6.9, 3.9 Hz, 4H). $^{13}$C NMR (CDCl$_3$) δ=181.6 (2×), 72.0, 37.3 (2×), 33.7 (2×), 29.9 (2×), 27.6 (2×), 25.6 (2×), 23.5 (2×), 16.7 (2×), 16.6 (2×). Anal. calcd for C$_{19}$H$_{32}$O$_5$: C, 67.03; H, 9.47. Found: C, 66.83; H, 9.24.

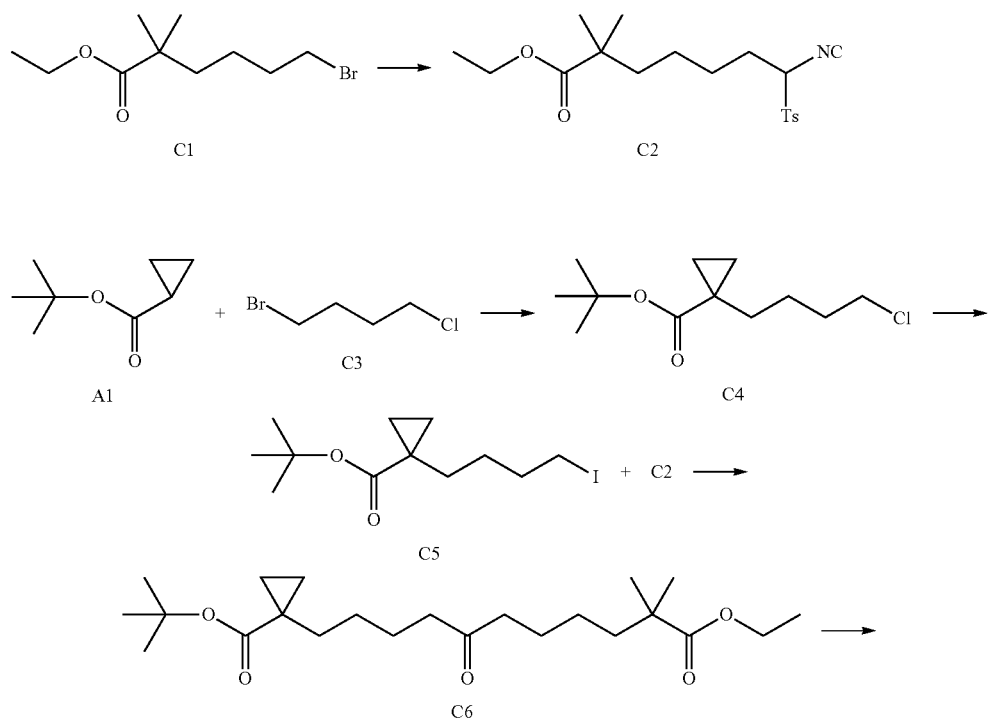

-continued

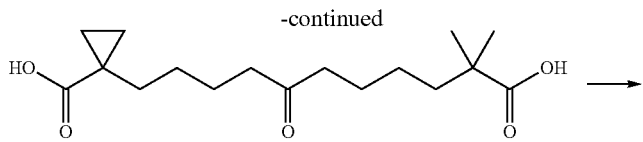

C7

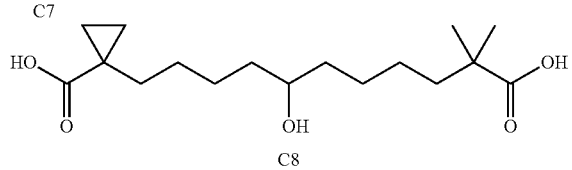

C8

6.10 {7-Ethoxy-6,6-dimethyl-1-[(4-methylphenyl)sulfonyl]-7-oxoheptyl}(methylidyne)ammonium To a mixture of $K_2CO_3$ (13.18 g, 95.6 mmol) and $Bu_4NI$ (2.35 g, 6.36 mmol) in dry DMF (50 mL) was added a solution of ethyl 2,2-dimethyl-6-bromohexanoate (prepared according to Ackerley, N.; Brewster, A. G.; Brown, G. R.; Clarke, D. S.; Foubister, A. J., Griffin, S. J.; Hudson, J. A.; Smithers, M. J.; Whittamore, P. R. O., *J. Med. Chem.*, 1995, 38, 1608-1628, 24.00 g, 95.6 mmol) and TosMIC (12.41 g, 63.7 mmol) in dry DMF (50 mL) in 20 min under a $N_2$ atmosphere while stirring vigorously. After 4 d, $H_2O$ (100 mL) was added drop wise while keeping the temperature below 25° C. by cooling with an ice-bath. The resulting mixture was extracted with $Et_2O$ (3×200 mL). The combined organic layers were washed with saturated aqueous $NaHCO_3$ (2×200 mL), dried ($Na_2SO_4$), and evaporated in vacuo. The remaining residue was purified by column chromatography (silica; heptane:EtOAc=6:1; a layer of $NaHCO_3$ was put on the base of the column) to give {7-ethoxy-6,6-dimethyl-1-[(4-methylphenyl)sulfonyl]-7-oxoheptyl}(methylidyne) ammonium (15.68 g, 42.8 mmol, 67%) as a slightly yellow oil which slowly solidified on standing. An analytical sample was obtained after recrystallization (0.43 g) from $iPr_2O$/heptane at ~4° C. to give {7-ethoxy-6,6-dimethyl-1-[(4-methylphenyl)sulfonyl]-7-oxoheptyl}(methylidyne)ammonium (0.30 g) as a white solid. mp: 38-39° C. NMR ($CDCl_3$): δ=7.84 (d, J=8.4 Hz, 2H), 7.40 (d, J=7.8 Hz, 2H), 4.43 (dd, J=3.3, 10.8 Hz, 1H), 4.10 (q, J=7.1 Hz, 2H), 2.48 (s, 3H), 2.23-2.12 (m, 1H), 1.90-1.77 (m, 1H), 1.66-40 (m, 4H), 1.38-1.22 (m, 2H), 1.24 (t, J=7.1 Hz, 3H), 1.15 (s, 6H). $^{13}$C NMR ($CDCl_3$): δ=177.3, 164.6, 146.3, 131.0, 129.93 (2×), 129.87 (2×), 72.8, 60.4, 42.2, 40.2, 28.4, 26.0, 25.35, 25.30, 24.2, 22.0, 14.5. Anal. calcd for $C_{19}H_{27}NO_4S$: C, 62.44; H, 7.45; N, 3.83, found: C, 62.57; H, 7.57; N, 3.96.

6.11 Tert-butyl 1-(4-chlorobutyl)-1-cyclopropanecarboxylate

Under an Ar atmosphere at 0° C., BuLi (2.5M in hexanes, 37 mL, 92.5 mmol) was added drop wise to a solution of $iPr_2NH$ (12.3 mL, 88 mmol, distilled from NaOH) in dry THF (150 mL) in 10 min. The reaction mixture was stirred for 20 min, cooled to −70° C. and then, tert-butyl cyclopropanecarboxylate (prepared according to Kohlrausch, K. W. F.; Skrabal, R., Z. *Elektrochem. Angew. Phys. Chem.*, 1937, 43, 282-285, 12.5 g, 88 mmol) was added drop wise in 20 min. After 3 min, 1-bromo-4-chlorobutane (13.7 mL, 20.1 g, 117 mmol) was added drop wise in 15 min. The reaction mixture was allowed to reach rt, poured into a mixture of aqueous saturated $NH_4Cl$ (200 mL) and ice (50 mL) and extracted with $Et_2O$ (1×200 mL, 1×100 mL). The combined organic layers were washed with brine, dried ($Na_2SO_4$) and evaporated in vacuo. The remaining oil, was purified by fractional distillation to give tert-butyl 1-(4-chlorobutyl)-1-cyclopropanecarboxylate (10.73 g, 52%) as a colorless oil. bp: T=57-61° C. (p=0.001 mbar). $^1$H NMR ($CDCl_3$): δ=3.52 (t, J=6.6 Hz, 2H), 1.76 (quintet, J=6.8 Hz, 2H), 1.64-1.54 (m, 2H), 1.51-1.46 (m, 2H), 1.42 (s, 9H), 1.12 (dd, J=6.6, 3.9 Hz, 2H), 0.60 (dd, J=6.6, 3.9 Hz, 2H). $^{13}$C NMR ($CDCl_3$): δ=173.9, 80.0, 45.1, 33.6, 32.9, 28.2 (3×), 25.3, 24.2, 15.4 (2×). HRMS calcd for $C_{12}H_{22}ClO_2$ ($MH^+$): 233.1308, found: 233.1308.

6.12 Tert-butyl 1-(4-iodobutyl)-1-cyclopropanecarboxylate

To a solution of tert-butyl 1-(4-chlorobutyl)-1-cyclopropanecarboxylate (10.6 g, 45.7 mmol) in 2-butanone (50 mL) was added NaI (8.23 g, 54.5 mmol). The reaction mixture was stirred under reflux overnight, diluted with $Et_2O$ (100 mL), washed with a mixture of $H_2O$ (100 mL) and aqueous $Na_2S_2O_4$ (0.5 M, 10 mL) and brine (50 mL). The organic phase was dried ($Na_2SO_4$) and evaporate in vacuo to give tert-butyl 1-(4-iodobutyl)-1-cyclopropanecarboxylate (14.8 g, 94% pure by GC, 94%) as a slightly yellow liquid. $^1$H NMR ($CDCl_3$): δ=3.18 (t, J=6.9 Hz, 2H), 1.76 (quintet, J=7.1 Hz, 2H), 1.62-1.45 (m, 4H), 1.43 (s, 9H), 1.12 (dd, J=6.7 Hz, 3.8 Hz, 2H), 0.60 (dd, J=6.6 Hz, 3.9 Hz, 2H). $^{13}$C NMR ($CDCl_3$): δ=173.9, 80.0, 33.8, 33.3, 28.9, 28.2 (3×), 24.2, 15.5 (2×), 7.2. HRMS calcd for $C_{12}H_{21}IO_2$ ($M^+$): 324.0587, found: 324.0587.

6.13 Ethyl 11-[1-(t-butoxycarbonyyl)cyclopropyl]-2,2-dimethyl-7-oxoundecanoate Under a $N_2$ atmosphere at 0° C., a solution of {7-ethoxy-6,6-dimethyl-1-[(4-methylphenyl)sulfonyl]-7-oxoheptyl}(methylidyne)ammonium (20.5 g, 55.9 mmol) in N,N-dimethylacetamide (DMAc, 125 mL) followed by a solution of tert-butyl 1-(4-iodobutyl)-1-cyclopropanecarboxylate (18.11 g, 55.9 mmol) in DMAc (125 mL) were added drop wise in 30 and 20 min, respectively to a solution of KOtBu (6.57 g, 58.7 mmol) in DMAc (250 mL). The mixture was allowed to reach rt and stirring was continued for 100 min. Then, the reaction mixture was quenched by the drop wise addition of $H_2O$ (250 mL) while cooling with an ice-bath. The resulting mixture was extracted with $Et_2O$ (3×250 mL) and the combined organic layers were washed with brine (2×250 mL), dried ($Na_2SO_4$) and evaporated in vacuo to give a yellow oil (31.79 g). Part of this oil (30.63 g) was dissolved in $CH_2Cl_2$ (300 mL) and conc aqueous HCl (23 mL) was added. After 2 h of vigorous stirring, $H_2O$ (250 mL) was added. The layers were separated and the aqueous phase was extracted with $CH_2Cl_2$ (3×250 mL). The combined organic phases were washed with saturated aqueous NaHCO$_3$ (250 mL), dried (Na$_2$SO$_4$) and evaporated in vacuo. To the remaining suspension of a yellow oil with a white solid was added heptane (~50 mL) and the white solid was filtered off and washed with heptane (~50 mL). The filtrate was stored at rt for 2 d and more white solid was formed, which was filtered off through a layer of silica (~1 cm) and washed with heptane (~50 mL). The combined filtrates were evaporated in vacuo to give impure ethyl 11-[1-(t-butoxycarbonyl)cyclopropyl]-2,2-dimethyl-7-oxoundecanoate (17.90 g) as a colorless oil. This batch was further purified by column chromatography (silica, heptane: EtOAc=40:1) to give ethyl 11-[1-(t-butoxycarbonyl)cyclopropyl]-2,2-dimethyl-7-oxoundecanoate (9.83 g, >90% pure by NMR, 43%) as a colorless oil. $^1$H NMR (CDCl$_3$): δ=4.09 (q, J=7.2 Hz, 2H), 2.38 (t, J=7.2 Hz, 4H), 1.62-1.35 (m, 10H), 1.41 (s, 9H), 1.26-1.17 (m, 2H), 1.24 (t, J=7.2 Hz, 3H), 1.14 (s, 6H), 1.09 (dd, J=6.9, 4.2 Hz, 2H), 0.59 (dd, J=6.3, 3.6 Hz, 2H). $^{13}$C NMR: δ 210.5, 177.4, 174.0, 79.8, 60.2, 42.8, 42.6, 42.1, 40.5, 34.0, 28.2 (3×), 27.5, 25.2 (2×), 24.7, 24.3, 24.2, 24.1, 15.3 (2×), 14.4. HRMS calcd for C$_{23}$H$_{41}$O$_5$ (MH$^+$): 397.2954, found: 397.2956.

6.14 11-(1-Carboxycyclopropyl)-2,2-dimethyl-7-oxoundecanoic acid

A solution of ethyl 11-[1-(t-butoxycarbonyl)cyclopropyl]-2,2-dimethyl-7-oxoundecanoate (9.27 g, >90% pure by NMR, 21.0 mmol) in HCO$_2$H (50 mL) was stirred for 1.5 h, evaporated in vacuo and coevaporated from toluene (10 mL). The remaining residue was dissolved in a mixture of EtOH and H$_2$O (2:1, 100 mL) and NaOH (5.33 g, 132 mmol) was added. The resulting clear solution was warmed to 80° C. and after 5 h EtOH was evaporated in vacuo. The remaining solution was diluted with H$_2$O to ~100 mL, extracted with Et$_2$O (3×100 mL), acidified to pH ~1 with cone aqueous HCl (~9 mL) and extracted with Et$_2$O (3×100 mL). The latter organic layers were combined, dried (Na$_2$SO$_4$) and evaporated in vacuo. The remaining residue was purified by column chromatography (silica, heptane:EtOAc=2:1 (containing 1% (v/v) HOAc)) to give 11-(1-carboxycyclopropyl)-2,2-dimethyl-7-oxoundecanoic acid (5.83 g, >90% pure by $^1$H NMR, 80%) as a slightly yellow oil which turns solid when stored at −18° C. for several days. mp: 49-52° C. $^1$H NMR (CD$_3$OD): δ=2.44 (t, J=7.2 Hz, 4H), 1.57-1.42 (m, 10H), 1.30-1.19 (m, 2H), 1.17-1.07 (m, 2H), 1.14 (s, 6H), 0.59 (dd, J=6.6, 3.9 Hz, 2H). $^{13}$C NMR (CD$_3$OD): δ=213.5, 181.4, 178.9, 43.5, 43.4, 43.0, 41.7, 34.9, 28.5, 25.9 (3×), 25.5, 25.2, 24.3, 16.4 (2×). Anal. calcd for C$_{17}$H$_{28}$O$_5$: C, 65.36; H, 9.03, found: C, 65.06; H, 9.02.

6.15 11-(1-Carboxycyclopropyl)-7-hydroxy-2,2-dimethylundecanoic acid

To a mixture of 11-(1-carboxycyclopropyl)-2,2-dimethyl-7-oxoundecanoic acid (3.63 g, >90% pure by NMR, 10.4 mmol) in iPrOH (20 mL) and H$_2$O (20 mL) was added NaOH (0.94 g, 23.5 mmol). After 5 min of stirring, NaBH$_4$ (0.24 g, 6.3 mmol) was added to the resulting clear solution. After 19 h, the mixture was acidified to pH~1 with aqueous HCl (2M) and extracted with Et$_2$O (3×50 mL). The combined organic phases were washed with brine (1×50 mL), dried (Na$_2$SO$_4$) and evaporated in vacuo. The remaining residue was coevaporated in vacuo from EtOAc to give 11-(1-carboxycyclopropyl)-7-hydroxy-2,2-dimethylundecanoic acid (3.43 g, 93%, contains 8% (w/w) EtOAc and 3% (w/w) iPrOH) as a viscous colorless oil. $^1$H NMR (CD$_3$OD): δ=3.5 (br s, 1H), 1.56-1.27 (m, 16H), 1.16 (s, 6H), 1.16-1.14 (m, 2H), 0.72 (dd, J=3.4, 6.6 Hz, 2H). $^{13}$C NMR (CD$_3$OD): δ=181.6, 179.1, 72.3, 43.1, 42.0, 38.5, 38.4, 35.2, 29.0, 27.5, 27.1, 26.4, 26.0, 25.9, 24.4, 16.43, 16.38. HRMS calcd for C$_{12}$H$_{31}$O$_5$ (M+H$^+$): 315.2171, found 315.2175.

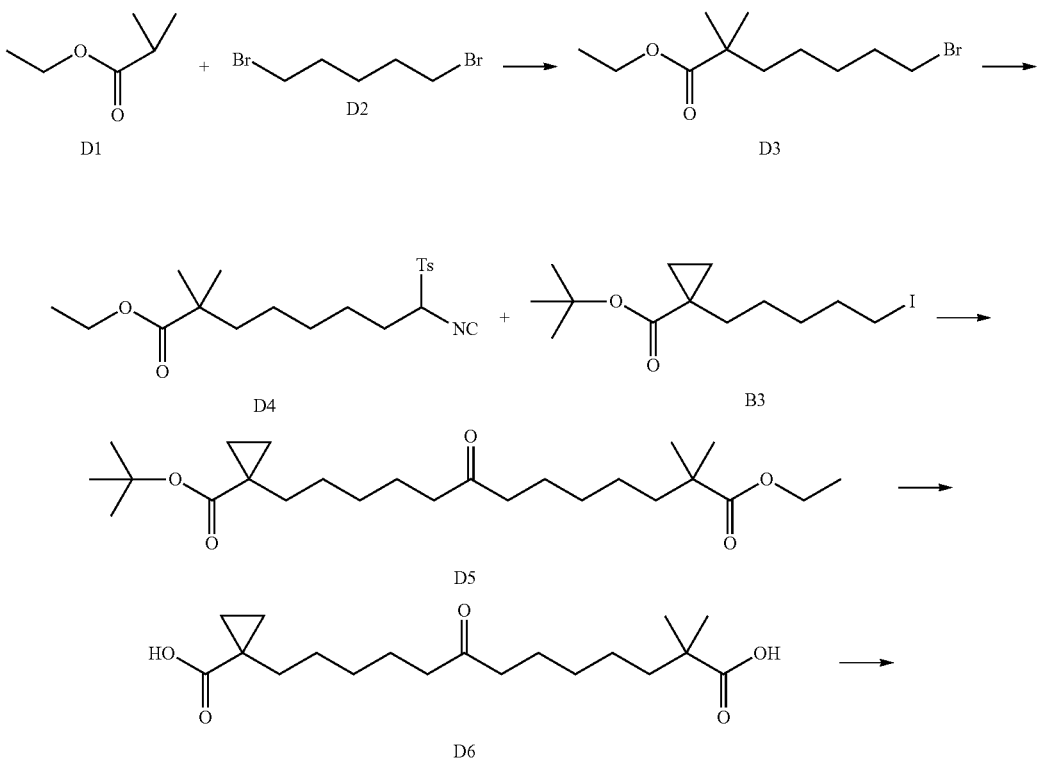

-continued

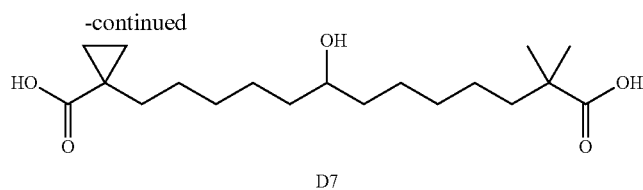

D7

6.16 Ethyl 7-bromo-2,2-dimethylheptanoate

Under Ar atmosphere at −78° C., to a solution of ethyl isobutyrate (124.0 g, 1.06 mol) and DMPU (5 mL) in THF (160 mL) was added LDA (750 mL, 2M). After 30 min, 1,5-dibromopentane (313 g, 1.32 mol) was added in a single portion. The reaction mixture was allowed to stir overnight, gradually warming to rt. The mixture was hydrolyzed with ice (500 g), saturated NH$_4$Cl (400 mL) and aqueous HCl (6M, 400 mL), and the solution was extracted with Et$_2$O (3×300 mL). The organic layers were washed with half saturated NaCl (2×300 mL), dried (MgSO$_4$) and evaporated in vacuo. The remaining residue was purified by distillation under reduced pressure to give ethyl 7-bromo-2,2-dimethylheptanoate (97.4 g, 32%) as a colorless oil. bp: T=109-110° C. (p=1.5-2 Ton). $^1$H NMR (CDCl$_3$): δ=4.15 (q, J=7.2 Hz, 2H), 3.40 (t, J=6.9 Hz, 2H), 1.90-1.83 (m, 2H), 1.55-1.37 (m, 4H), 1.25 (t, J=6.9 Hz, 3H), 1.30-1.22 (m, 2H), 1.16 (s, 6H). $^{13}$C NMR (CDCl$_3$): δ=177.9, 60.3, 42.2, 40.5, 33.7, 32.7, 28.6, 25.2, 24.2, 14.3. HRMS calcd for C$_{11}$H$_{22}$BrO$_2$ (MH$^+$): 265.0803, found: 265.0816.

6.17 {8-Ethoxy-7,7-dimethyl-1-[(4-methylphenyl)sulfonyl]-8-xooctyl}(methylidvne)ammonium Under a N$_2$ atmosphere, TosMIC (10.01 g, 51.3 mmol) and ethyl 7-bromo-2,2-dimethylheptanoate (20.41 g, 77.0 mmol) were dissolved in dry DMF (100 mL) and Bu$_4$NI (1.89 g, 5.12 mmol) and K$_2$CO$_3$ (10.62 g, 76.8 mmol) were added while stirring vigorously. After 5 d, the reaction mixture was poured in an ice/H$_2$O mixture (500 mL), extracted with Et$_2$O (1×200 mL, 2×100 mL) The combined organic layers were washed with brine (2×50 mL), dried (Na$_2$SO$_4$), and evaporated in vacuo. The remaining residue was purified by column chromatography (silica, heptane:EtOAc=3:1) to give in order of elution ethyl 7-bromo-2,2-dimethylheptanoate (5.67 g, 90% pure by GC), an impure batch of {8-ethoxy-7,7-dimethyl-1-[(4-methylphenyl)sulfonyl]-8-oxooctyl}(methylidyne)ammonium (0.94 g), and pure {8-ethoxy-7,7-dimethyl-1-[(4-methylphenyl)sulfonyl]-8-oxooctyl}(methylidyne)ammonium (11.83 g, 61%) as a colorless oil. $^1$H NMR (CDCl$_3$): δ=7.86 (d, J=8.1 Hz, 2H), 7.43 (d, J=8.1 Hz, 2H), 4.45 (dd, J=10.9, 3.5 Hz, 1H), 4.11 (q, J=7.2 Hz, 2H), 2.49 (s, 3H), 2.22-2.11 (m, 1H), 1.90-1.77 (m, 1H), 1.67-1.57 (m, 1H), 1.53-1.42 (m, 3H), 1.24 (t, J=7.2 Hz, 3H), 1.39-1.20 (m, 4H), 1.15 (s, 6H). $^{13}$C NMR (CDCl$_3$): δ=177.8, 164.8, 146.5, 131.1, 130.1 (2×), 130.0 (2×), 72.8, 60.2, 42.0, 40.3, 29.0, 28.3, 25.12, 25.06 (2×), 24.5, 21.7, 14.2. HRMS calcd for C$_{20}$H$_{29}$NNaO$_4$S (MNa$^+$): 402.1715, found: 402.1736.

6.18 Ethyl 13-[1-(t-butoxycarbonyl)cyclopropyl]-2,2-dimethyl-8-oxotridecanoate Under a N$_2$ atmosphere at 0° C., a solution of {8-ethoxy-7,7-dimethyl-1-[(4-methylphenyl)sulfonyl]-8-oxooctyl}(methylidyne)ammonium (28.4 g, 75.0 mmol) in N,N-dimethylacetamide (DMAc, 125 mL) followed by a solution of tert-butyl 1-(5-iodopentyl)-1-cyclopropanecarboxylate (B3, 25.4 g, 75.0 mmol) in DMAc (125 mL) were added dropwise in 60 and 30 min, respectively to a solution of KOtBu (8.83 g, 79.0 mmol) in DMAc (250 mL). The mixture was allowed to reach rt and stirring was continued for 2 h. Then, the reaction mixture was quenched by the dropwise addition of H$_2$O (250 mL) while cooling with an ice-bath. The resulting mixture was extracted with Et$_2$O (3×250 mL) and the combined organic layers were washed with brine (2×250 mL), dried (Na$_2$SO$_4$) and evaporated in vacuo to give a yellow oil (43.02 g). Part of this oil (42.50 g) was dissolved in CH$_2$Cl$_2$ (250 mL) and conc aqueous HCl (34 mL) was added. After 1.5 h of vigorous stirring, H$_2$O (250 mL) was added. The layers were separated and the aqueous phase was extracted with CH$_2$Cl$_2$ (3×250 mL). The combined organic phases were washed with saturated aqueous NaHCO$_3$ (250 mL), dried (Na$_2$SO$_4$) and evaporated in vacuo. To the remaining residue was purified by column chromatography (silica, heptane:EtOAc=8:1) to give ethyl 13-[1-(t-butoxycarbonyl)cyclopropyl]-2,2-dimethyl-8-oxotridecanoate (19.0 g, 95% pure by $^1$H NMR, 57%) as a slightly yellow oil. $^1$H NMR (CDCl$_3$): δ=4.09 (q, J=7.2 Hz, 2H), 2.37 (t, J=7.2 Hz, 2H), 2.36 (t, J=7.2 Hz, 2H), 1.62-1.35 (m, 10H), 1.41 (s, 9H), 1.30-1.21 (m, 6H), 1.24 (t, J=7.2 Hz, 3H), 1.14 (s, 6H), 1.09 (dd, J=6.6, 3.9 Hz, 2H), 0.58 (dd, J=6.3, 3.6 Hz, 2H). $^{13}$C NMR (CDCl$_3$): δ=210.8, 177.6, 174.1, 79.8, 60.2, 42.9. 42.8, 42.2, 40.6, 34.1, 29.8, 29.6, 28.2 (3×), 27.6, 25.3 (2×), 24.9, 24.3, 23.9, 23.8, 15.3 (2×), 14.4. HRMS calcd for C$_{25}$H$_{45}$O$_5$ (MH$^+$): 425.3267, found: 425.3267.

6.19 13-(1-Carboxycyclopropyl)-2,2-dimethyl-8-oxotridecanoic acid

A solution of ethyl 13-[1-(t-butoxycarbonyl)cyclopropyl]-2,2-dimethyl-8-oxotridecanoate (18.34 g, 43.3 mmol) in HCO$_2$H (50 mL) was stirred for 1.5 h, evaporated in vacuo and coevaporated in vacuo from toluene (10 mL). The remaining residue was dissolved in a mixture of EtOH and H$_2$O (2:1, 250 mL) and NaOH (9.68 g, 241 mmol) was added. The resulting clear solution was warmed to 80° C. and after 5 h EtOH was evaporated in vacuo. The remaining solution was diluted with H$_2$O to ~250 mL, extracted with Et$_2$O (3×250 mL), acidified to pH~1 with conc aqueous HCl (~18 mL) and extracted with Et$_2$O (3×250 mL). The latter organic layers were combined, dried (Na$_2$SO$_4$) and evaporated in vacuo to give a yellow oil which solidified overnight. The remaining residue was recrystallized from iPr$_2$O/heptane to give 13-(1-carboxycyclopropyl)-2,2-dimethyl-8-oxotridecanoic acid (9.47 g, 57%) as a white solid. The mother liquor was evaporated in vacuo and the remaining residue was purified by column chromatography (heptane:EtOAc=2:1 (containing 1% (v/v) HOAc)) and recrystallization from iPr$_2$O/heptane to give a second batch 13-(1-carboxycyclopropyl)-2,2-dimethyl-8-oxotridecanoic acid (2.23 g, 14%) as a white solid. mp=65-66° C. $^1$H NMR: (CD$_3$OD): δ=2.43 (t, J=7.2 Hz, 4H), 1.58-1.42 (m, 10H), 1.35-1.20 (m, 6H), 1.14 (s, 6H), 1.15-1.06 (m, 2H), 0.70 (dd, J=6.6, 3.9 Hz, 2H). $^{13}$C NMR:

(CD$_3$OD): δ=213.8, 181.6, 179.0, 43.6, 43.5, 43.1, 41.9, 35.1, 31.0, 30.6, 28.7, 26.2, 25.9 (2×), 25.02, 24.96, 24.4, 16.4 (2×). Anal. calcd for C$_{19}$H$_{32}$O$_5$: C, 67.03; H, 9.47, found: C, 66.86; H, 9.50.

6.20 13-(1-Carboxycyclopropyl)-8-hydroxy-2,2-dimethyltridecanoic acid

To a mixture of 13-(1-carboxycyclopropyl)-2,2-dimethyl-8-oxotridecanoic acid (3.67 g, 10.8 mmol) in iPrOH (20 mL) and H$_2$O (20 mL) was added NaOH (0.90 g, 22.5 mmol). After 5 min of stirring, NaBH$_4$ (0.20 g, 5.3 mmol) was added to the resulting clear solution. Additional NaBH$_4$ (0.10 g) was added after 100 min of stirring. After 16 h, the mixture was acidified to pH~1 with aqueous HCl (1M) and extracted with Et$_2$O (3×50 mL). The combined organic phases were washed with brine (2×50 mL), dried (Na$_2$SO$_4$), evaporated in vacuo and coevaporated in vacuo from EtOAc (2×15 mL) to give 13-(1-carboxycyclopropyl)-8-hydroxy-2,2-dimethyltridecanoic acid (3.99 g, 97%, contains 10% %(w/w) EtOAc) as a viscous colorless oil. $^1$H NMR (CD$_3$OD): δ=3.48 (m, 1H), 1.50-1.21 (m, 20H), 1.14 (s, 6H), 1.14-1.12 (m, 2H), 0.70 (dd, J=3.9, 6.3 Hz, 2H). $^{13}$C NMR (CD$_3$OD): δ=181.6, 179.0, 72.4, 43.2, 42.0, 38.6, 38.5, 35.2, 31.5, 31.2, 28.9, 26.94, 26.87, 26.3, 25.94, 25.92, 24.4, 13.67, 16.36. HRMS calcd for C$_{19}$H$_{35}$O$_5$ (M+H)$^+$: 343.2484, found 343.2487.

Molnár, Á., J. Chem. Soc. Perkin Trans. 1, 1993, 7, 801-804, 14.05 g, 110 mmol) in dry THF (30 mL) was added dropwise in 20 min. The resulting mixture was allowed to warm to 0° C. in 20 min., cooled again to −60° C. and then, a solution of 1-bromo-4-chlorobutane (19.1 mL, 165 mmol) in dry THF (30 mL) was added dropwise in 20 min, after which the temperature was raised to −20° C. in 15 min. After 1.5 h, the temperature was raised to −10° C. and stirring was continued for 1 h. The reaction mixture was allowed to reach rt, poured into a mixture of aqueous saturated NH$_4$Cl (200 mL) and ice (50 mL) and extracted with Et$_2$O (500 mL). The organic layer was washed with brine (250 mL), dried (Na$_2$SO$_4$) and evaporated in vacuo. The remaining oil was purified by fractional distillation under reduced pressure to give ethyl 1-(4-chlorobutyl)-1-cyclobutanecarboxylate (20.53 g, 86%) as a thin, colorless oil. $^1$H NMR (CDCl$_3$): δ=4.13 (q, J=7.1 Hz, 2H), 3.51 (t, J=6.8 Hz, 2H), 2.50-2.32 (m, 2H), 1.96-1.70 (m, 8H), 1.40-1.20 (m, 2H), 1.26 (t, J=7.2 Hz, 3H). $^{13}$C NMR (CDCl$_3$): δ=176.6, 60.3, 47.6, 44.8, 37.3, 32.8, 30.1 (2×), 22.4, 15.8, 14.4. HRMS calcd for C$_{11}$H$_{20}$($^{37}$Cl)O$_2$ (WO: 221.1122, found: 221.1116.

6.22 Ethyl 1-(4-iodobutyl)-1-cyclobutanecarboxylate

To a solution of ethyl 1-(4-chlorobutyl)-1-cyclobutanecarboxylate (21.21 g, 97.0 mmol) in 2-butanone (125 mL) was

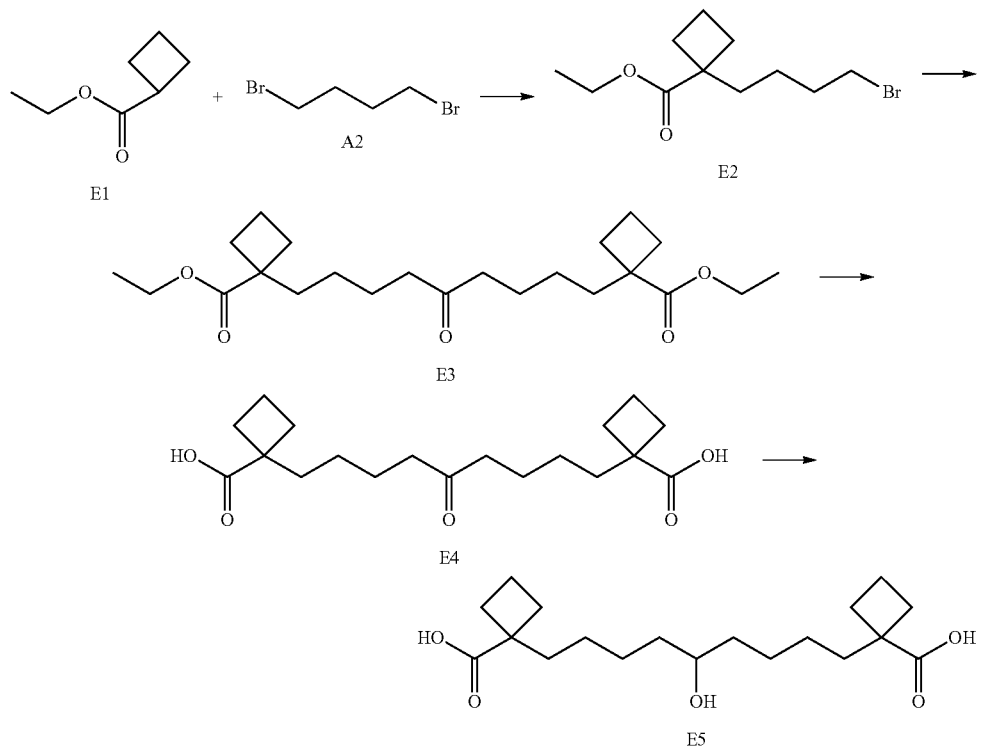

6.21 Ethyl 1-(4-chlorobutyl)-1-cyclobutanecarboxylate

Under an N$_2$ atmosphere at ~7° C., BuLi (2.5M in hexanes, 52.8 mL, 132 mmol) was added drop wise to a solution of iPr$_2$NH (18.52 mL, 132 mmol, distilled from NaOH) in dry THF (70 mL) in 10 min. The reaction mixture was allowed to warm to rt, stirred for 0.5 h, cooled to −60° C. and then, ethyl 1-cyclobutanecarboxylate (prepared according to Török, B.;

added NaI (19.07 g, 127 mmol). The reaction mixture was stirred under reflux for 20 h and diluted with Et$_2$O (500 mL). The resulting mixture was washed with aqueous Na$_2$S$_2$O$_3$ (10% (w/w), 250 mL), brine (250 mL), dried (Na$_2$SO$_4$) and evaporated in vacuo to give ethyl 1-(4-iodobutyl)-1-cyclobutanecarboxylate (29.91 g, 99%) as a slightly yellow oil. $^1$H NMR (CDCl$_3$): δ=4.14 (q, J=7.1 Hz, 2H), 3.17 (t, J=6.9 Hz, 2H), 2.49-2.32 (m, 2H), 1.98-1.69 (m, 8H), 1.37-1.19 (m, 2H), 1.27 (t, J=7.1 Hz, 3H). $^{13}$C NMR (CDCl$_3$): δ=176.5, 60.3, 47.5, 36.9, 33.7, 30.1 (2×), 26.0, 15.7, 14.5, 6.8. HRMS calcd for $C_{11}H_{20}IO_2$ (MH$^+$): 311.0508, found: 311.0511.

6.23 Ethyl 1-9-[1-(ethoxycarbonyl)cyclobutyl]-5-oxononyl-1-cyclobutanecarboxylate Under a N$_2$ atmosphere at 0° C., KOtBu (8.61 g, 76.7 mmol) was added portion wise to a solution of ethyl 1-(4-iodobutyl)-1-cyclobutanecarboxylate (24.83 g, 80.1 mmol) and TosMIC (7.26 g, 36.4 mmol) in DMAc (150 mL). After 30 min, the reaction mixture was allowed to warm to rt, stirred for 1.5 h and diluted with DMAc (10 mL). Then, ethyl 1-(4-iodobutyl)-1-cyclobutanecarboxylate (2.01 g, 6.5 mmol) and KOtBu (0.81 g, 7.2 mmol) were added followed by another portion of ethyl 1-(4-iodobutyl)-1-cyclobutanecarboxylate (1.00 g, 3.2 mmol) and KOtBu (0.86 g, 7.7 mmol) after 1 h. After 1 h, the reaction mixture was poured into a mixture of Et$_2$O (700 mL) and aqueous NaCl (10%, 500 mL) and the layers were separated. The organic layer was washed with brine (1×500 mL, 1×300 mL), dried (Na$_2$SO$_4$) and evaporated in vacuo. The remaining residue was purified by column chromatography (silica, heptane:EtOAc=6:1) to give ethyl 1-9-[1-(ethoxycarbonyl)cyclobutyl]-5-isocyano-5-[(4-methylphenyl)sulfonyl]nonyl-1-cyclobutanecarboxylate (18.35 g) as a slightly yellow oil. Part of this oil (15.62 g, 27.9 mmol) was dissolved in CH$_2$Cl$_2$ (200 mL) and conc aqueous HCl (75 mL) was added. After stirring vigorously for 2 h, H$_2$O (300 mL) was added and the layers were separated. The aqueous layer was extracted with CH$_2$Cl$_2$ (2×100 mL) and the combined CH$_2$Cl$_2$ layers were washed with saturated aqueous NaHCO$_3$ (2×250 mL) and brine (250 mL). All aqueous layers were combined and extracted with Et$_2$O (2×200 mL). The combined Et$_2$O layers were washed with saturated aqueous NaHCO$_3$ (200 mL) and brine (200 mL). The CH$_2$Cl$_2$ layers and Et$_2$O layers were combined, dried (Na$_2$SO$_4$) and evaporated in vacuo. To the remaining residue heptane (150 mL) was added, and the mixture was filtered through two stacked folded filter papers. The hazy filtrate was filtered again to give a clear filtrate, which was evaporated in vacuo. The remaining residue was purified by column chromatography (silica, heptane:EtOAc=6:1) to give ethyl 1-9-[1-(ethoxycarbonyl)cyclobutyl]-5-oxononyl-1-cyclobutanecarboxylate (9.99 g, 82%) as a slightly yellow liquid, after evaporation from CH$_2$Cl$_2$ (100 mL). $^1$H NMR (CDCl$_3$): δ=4.12 (q, J=7.1 Hz, 4H), 2.44-2.32 (m, 8H), 1.93-1.79 (m, 8H), 1.77-1.72 (m, 4H), 1.55 (quintet, J=7.5 Hz, 4H), 1.25 (t, J=7.1 Hz, 6H), 1.21-1.10 (m, 4H). $^{13}$C NMR (CDCl$_3$): δ=210.2, 176.7 (2×), 60.2 (2×), 47.6 (2×), 42.6 (2×), 37.9 (2×), 30.1 (4×), 24.7 (2×), 24.1 (2×), 15.7 (2×), 14.4 (2×). HRMS calcd for $C_{23}H_{38}O_5$ (M$^+$): 394.2719, found: 394.2703.

6.24 1-[9-(1-Carboxycyclobutyl)-5-oxononyl]-1-cyclo-butanecarboxylic acid

LiOH.H$_2$O (3.94 g, 93.9 mmol) and H$_2$O (30 mL) were added to a solution of ethyl 1-9-[1-(ethoxycarbonyl)cyclobutyl]-5-oxononyl-1-cyclobutanecarboxylate (9.20 g, 23.3 mmol) in EtOH (90 mL) and the resulting mixture was stirred at reflux temperature for 17 h, allowed to cool to rt and concentrated in vacuo to a smaller volume. H$_2$O (150 mL) was added and the resulting mixture was extracted with Et$_2$O (50 mL), acidified with aqueous HCl (6 M, 25 mL) and extracted with Et$_2$O (1×100 mL, 2×50 mL). The latter organic layers were combined, washed with brine (50 mL), dried (Na$_2$SO$_4$) and evaporated in vacuo. The remaining residue was recrystallized from a mixture of iPr$_2$O and heptane to give 1-[9-(1-carboxycyclobutyl)-5-oxononyl]-1-cyclo-butanecarboxylic acid (4.41 g, 56%) as small, white granules. mp 69-70° C. $^1$H NMR (CDCl$_3$): δ=11.2 (br s, 2H), 2.50-2.37 (m, 4H), 2.39 (t, J=7.2 Hz, 4H), 1.96-1.84 (m, 8H), 1.81-1.75 (m, 4H), 1.57 (quintet, J=7.4 Hz, 4H), 1.26-1.12 (m, 4H). $^{13}$C NMR (CDCl$_3$): δ=210.6, 183.4 (2×), 47.6 (2×), 42.7 (2×), 37.8 (2×), 30.1 (4×). 24.7 (2×), 24.1 (2×), 15.7 (2×). Anal. calcd for $C_{19}H_{30}O_5$: C, 67.43; H, 8.93, found: C, 67.19; H, 8.97.

6.25 1-[9-(1-Carboxycyclobutyl)-5-hydroxynonyl]-1-cyclobutanecarboxylic acid To a solution of 1-[9-(1-carboxycyclobutyl)-5-oxononyl]-1-cyclo-butanecarboxylic acid (7.83 g, 23.1 mmol) in aqueous NaOH (1M, 70 mL) and i-PrOH (70 mL) was added NaBH$_4$ (0.659 g, 17.3 mmol). After stirring for 3.5 h, the reaction mixture was acidified to pH~1 with conc HCl and extracted with Et$_2$O (1×250 mL, 2×150 mL). The combined organic layers were washed with brine (250 mL), dried (Na$_2$SO$_4$) and concentrated in vacuo. The remaining residue was dried under high vacuum to give 1-[9-(1-carboxycyclobutyl)-5-hydroxynonyl]-1-cyclobutanecarboxylic acid (8.17 g, 97%, contains 7% (w/w) Et$_2$O) as a thick, colorless oil. $^1$H NMR (CDCl$_3$): δ=8.56 (br s, 3H), 3.58 (br s, 1H), 2.55-2.30 (m, 4H), 2.00-1.80 (m, 8H), 1.78 (t, J=7.7 Hz, 4H), 1.52-1.15 (m, 12H). $^{13}$C NMR (CDCl$_3$): δ=183.0 (2×), 71.7, 47.7 (2×), 38.0 (2×), 37.1 (2×), 30.2 (2×), 30.1 (2×), 25.9 (2×), 25.0 (2×), 15.7 (2×).

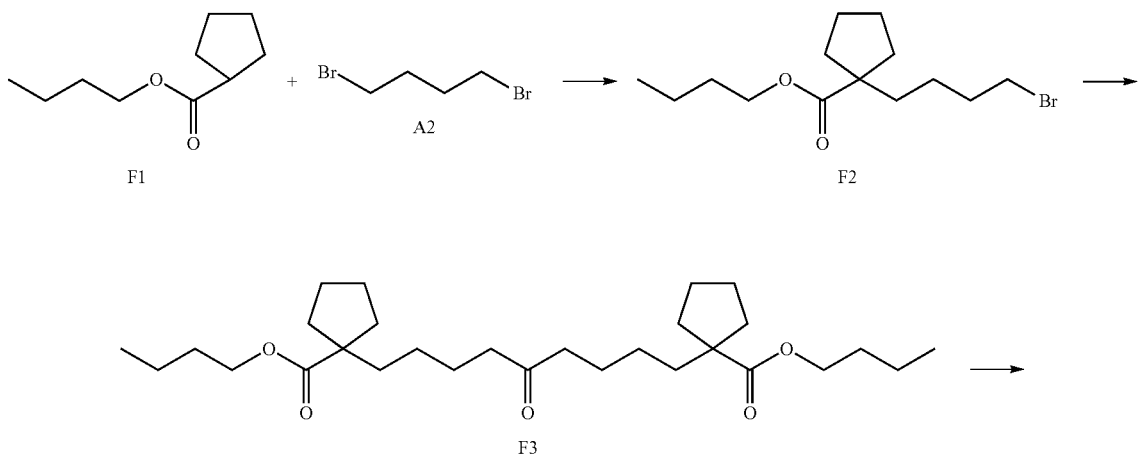

F1

F2

F3

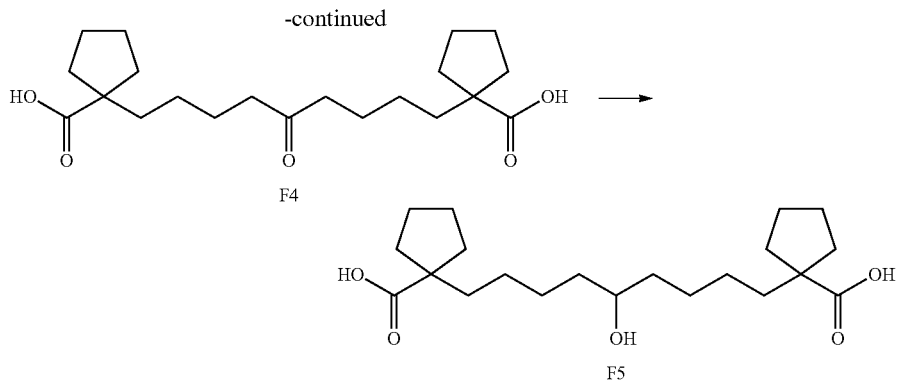

F4

F5

6.26 Butyl 1-(4-bromo-butyl)-cyclopentanecarboxylate

Under a $N_2$ atmosphere at −60° C., a solution of butyl cyclopentanecarboxylate (prepared according to Payne, G. B.; Smith, C. W., *J. Org. Chem.*, 1957, 22, 1680-1682, 80.0 g, 0.42 mol) and 1,4-dibromobutane (183.3 g, 0.84 mol) in dry THF (700 mL) was added drop wise to a mixture of LDA (2M in THF/heptane/ethylbenzene, 250 mL, 0.50 mol) and dry THF (250 mL) in 1.5 h. After that, the reaction mixture was allowed to slowly reach rt during 3.5 h. Then, the reaction mixture was poured into ice-cold saturated aqueous $NH_4Cl$ (1 L). The organic layer was decanted and concentrated in vacuo to a smaller volume. The aqueous layer was extracted with $Et_2O$ (3×250 mL). The combined organic layers were washed with saturated aqueous $NH_4Cl$ (250 mL) and brine (2×250 mL), dried ($Na_2SO_4$) and evaporated in vacuo. The remaining residue was purified by fractional distillation to give butyl 1-(4-bromo-butyl)-cyclopentanecarboxylate (62.8 g, 49%) as a light yellow liquid. bp: T=116-117° C. (p=0.040-0.051 Torr). $^1$H NMR ($CDCl_3$): δ=4.07 (t, J=6.6 Hz, 2H), 3.38 (t, J=6.8 Hz, 2H), 2.16-2.10 (m, 2H), 1.83 (quintet, J=7.1 Hz, 2H), 1.65-1.59 (m, 8H), 1.50-1.31 (m, 6H), 0.94 (t, J=7.2 Hz, 3H). $^{13}$C NMR ($CDCl_3$): δ=177.6, 64.1, 53.9, 38.2, 36.0 (2×), 33.3, 33.0, 30.6, 24.8 (2×), 24.6, 19.1, 13.6. HRMS calcd for $C_{14}H_{25}BrO_2$ ($M^+$): 304.1038, found: 304.1042.

6.27 Butyl 1-9-[1-(butoxycarbonyl)cyclopentyl]-5-oxononyl-1-cyclopentanecarboxylate Under a $N_2$ atmosphere, NaH (60% (w/w) in mineral oil, 3.20 g, 80.0 mmol) was added portion wise to a solution of TosMIC (6.58 g, 33.0 mmol) and $Bu_4NI$ (1.31 g, 3.55 mmol) in dry DMSO (100 mL) while stirring vigorously and cooling with a water bath. After 30 min, butyl 1-(4-bromo-butyl)-cyclopentanecarboxylate (21.59 g, 67.2 mmol) was added drop wise to the mixture in 20 min and after 1 h of stirring, another portion of NaH (60% (W in mineral oil, 0.56 g, 14 mmol) was added. After 20 min, $H_2O$ (250 mL, ice-cold) was added drop wise while cooling with a water bath and the resulting mixture was extracted with $Et_2O$ (3×100 mL). The combined organic layers were washed with brine (2×100 mL), dried ($Na_2SO_4$) and filtered through a layer of silica. The residue was washed with $Et_2O$ (200 mL) and the combined filtrate and washings were evaporated in vacuo. The remaining oil was purified by column chromatography (silica, heptane/EtOAc=8:1) to give butyl 1-{9-[1-(butoxycarbonyl)cyclopentyl]-5-isocyano-5-[(4-methylphenyl)sulfonyl]nonyl}-1-cyclopentanecarboxylate as a yellow oil (13.38 g). This oil (13.38 g) was dissolved in $CH_2Cl_2$ (250 mL), and conc aqueous HCl (75 mL) was added. After stirring vigorously for 18 h, $H_2O$ (300 mL) was added and the layers were separated. The aqueous phase was extracted with $CH_2Cl_2$ (2×100 mL) and the combined organic layers were washed with saturated aqueous $NaHCO_3$ (2×250 mL) and brine (250 mL), dried ($Na_2SO_4$) and evaporated in vacuo. The remaining residue was suspended in heptane (100 mL) and filtered. The filtrate was evaporated in vacuo. The remaining residue was purified by column chromatography (silica, heptane/EtOAc=6:1) to give butyl 1-9-[1-(butoxycarbonyl)cyclopentyl]-5-oxononyl-1-cyclopentanecarboxylate (9.05 g, 56%) as a slightly yellow liquid. $^1$H NMR ($CDCl_3$): δ=4.05 (t, J=6.5 Hz, 4H), 2.36 (t, J=7.5 Hz, 4H), 2.14-2.05 (m, 4H), 1.65-1.32 (m, 28H), 1.24-1.16 (m, 4H), 0.96 (t, J=7.2 Hz, 6H). $^{13}$C NMR ($CDCl_3$): δ=210.8, 177.8 (2×), 64.1 (2×), 54.0 (2×), 42.6 (2×), 39.0 (2×), 36.0 (4×), 30.7 (2×), 25.6 (2×), 24.9 (4×), 24.1 (2×), 19.1 (2×), 13.6 (2×). HRMS calcd for $C_{29}H_{50}O_5$ ($M^+$): 478.3658, found 478.3663.

6.28 1-[9-(1-Carboxycyclopentyl)-5-oxononyl]-1-cyclopentanecarboxylic acid $LiOH \cdot H_2O$ (3.21 g, 76.4 mmol) and $H_2O$ (40 mL) were added to a solution of butyl 1-9-[1-(butoxycarbonyl)cyclopentyl]-5-oxononyl-1-cyclopentanecarboxylate (7.25 g, 15.0 mmol) in EtOH (120 mL) and the resulting mixture was stirred at reflux temperature for 25 h, allowed to cool to rt and concentrated in vacuo to a smaller volume. $H_2O$ (100 mL) was added and the resulting mixture was extracted with $Et_2O$ (25 mL), acidified with aqueous HCl (6 M, 15 mL) and extracted with $Et_2O$ (3×50 mL). The latter organic layers were combined, dried ($Na_2SO_4$, to avoid loss of material, a minimal amount of $Na_2SO_4$ was used, with the desiccant becoming a white, oily paste. The organic layer was decanted from the desiccant.) and evaporated in vacuo to give 1-[9-(1-carboxycyclopentyl)-5-oxononyl]-1-cyclopentanecarboxylic acid (5.46 g, 95% pure by $^1$H NMR, 94%, mp=99-103° C.) as a white solid. An analytical sample was obtained after recrystallization from $iPr_2O$/heptane. mp=104-106° C. $^1$H NMR ($CDCl_3$): δ=2.39 (t, J=6.9 Hz, 4H), 2.18-2.10 (m, 4H), 1.69-141 (m, 20H), 1.27-1.14 (m, 4H). $^{13}$C NMR ($CDCl_3$): δ=211.1, 184.6 (2×), 53.9 (2×), 42.5 (2×), 39.0 (2×), 35.9 (4×), 25.7 (2×), 24.9 (4×), 24.0 (2×). Anal. calcd for $C_{21}H_{34}O_5$: C, 68.82; H, 9.35, found: C, 68.78; H, 9.47.

6.29 1-[9-(1-Carboxycyclopentyl)-5-hydroxynonyl]-1-cyclo-pentanecarboxylic acid To a mixture of 1-[9-(1-carboxycyclopentyl)-5-oxononyl]-1-cyclopentanecarboxylic acid (4.70 g, 11.5 mmol) in iPrOH (30 mL) and H$_2$O (30 mL) was added NaOH (1.10 g, 27 mmol). To the resulting clear solution, NaBH$_4$ (0.242 g, 6.4 mmol) was added. After 23 h, TLC analysis revealed the reaction to be incomplete, and an additional portion of NaBH$_4$ (0.036 g, 0.95 mmol) was added. Stirring was continued for 17 h and then, the reaction mixture was concentrated in vacuo. The remaining residue was dissolved in H$_2$O (80 mL) and washed with Et$_2$O (20 mL). The aqueous layer was acidified with aqueous HCl (6M, 15 mL) and then extracted with Et$_2$O (3×50 mL). The combined organic layers were washed with brine (2×50 mL), dried (Na$_2$SO$_4$) and concentrated in vacuo to give 1-[9-(1-carboxycyclopentyl)-5-hydroxynonyl]-1-cyclo-pentanecarboxylic acid (4.45 g, 98%, contains 7% (w/w) Et$_2$O) as a thick, slightly hazy, light yellow oil. $^1$H NMR (CDCl$_3$): δ=3.56 (br s, 1H), 2.16-2.10 (m, 4H), 1.65-1.60 (m, 12H), 1.51-1.18 (m, 16H). $^{13}$C NMR (CDCl$_3$): δ=184.1 (2×), 71.1, 54.2 (2×), 39.4 (2×), 37.1 (2×), 36.1 (2×), 35.7 (2×), 26.0 (2×), 25.8 (2×), 25.03 (2×), 25.00 (2×).

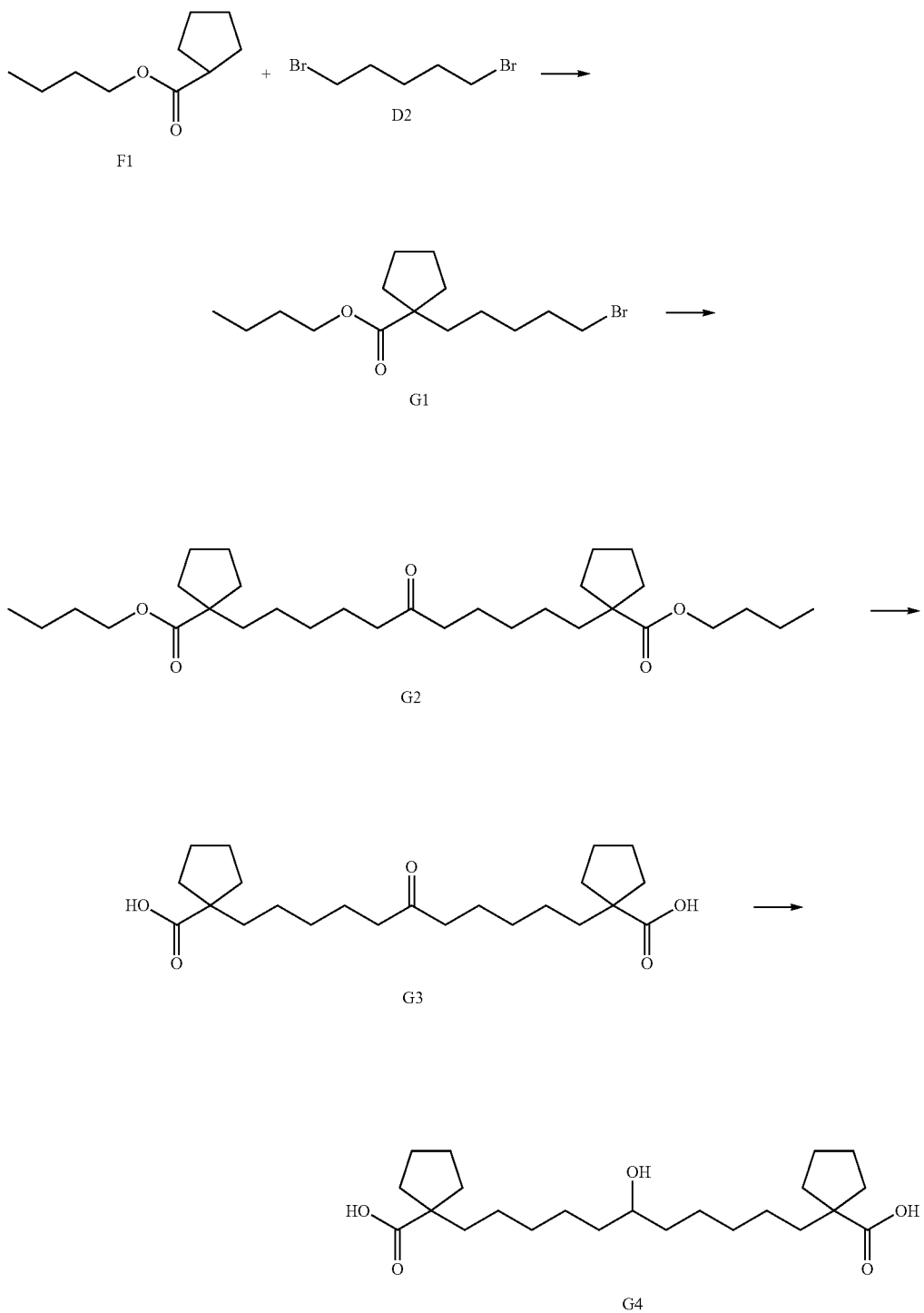

6.30 Butyl 1-(5-bromo-pentyl)-cyclopentanecarboxylate

Under a $N_2$ atmosphere at −60° C., a solution of butyl cyclopentanecarboxylate (prepared according to Payne, G. B.; Smith, C. W., *J. Org. Chem.*, 1957, 22, 1680-1682, 40.2 g, 0.236 mol) and 1,5-dibromopentane (64 mL, 0.45 mol) in dry THF (400 mL) was added drop wise to a solution of LDA (2M in THF/heptane/ethylbenzene, 200 mL, 0.40 mol) in 30 min. After 3 h, the reaction mixture was allowed to reach rt in 30 min. Then the reaction mixture was poured out into ice-cold saturated aqueous $NH_4Cl$ (1 L). The organic layer was decanted and concentrated in vacuo to a smaller volume. The aqueous layer was extracted with $Et_2O$ (3×150 mL). The combined organic layers were washed with saturated aqueous $NH_4Cl$ (3×150 mL), brine (150 mL), dried ($Na_2SO_4$) and evaporated in vacuo. The remaining residue was purified by fractional distillation to give butyl 1-(5-bromo-pentyl)-cyclopentanecarboxylate (49.1 g, >90% pure by GC, 59%) as a bright yellow liquid. bp: T=123° C. (p=0.001 Torr). $^1$H NMR ($CDCl_3$): δ=4.06 (t, J=6.6 Hz, 2H), 3.38 (t, J=6.9 Hz, 2H), 2.15-2.07 (m, 2H), 1.89-1.79 (quintet, J=7.1 Hz, 2H), 1.69-1.56 (m, 8H), 1.49-1.32 (m, 6H), 1.28-1.17 (m, 2H), 0.94 (t, J=7.4 Hz, 3H). $^{13}$C NMR ($CDCl_3$): δ=177.7, 64.0, 54.0, 39.0, 36.0 (2×), 33.6, 32.5, 30.7, 28.5, 25.1, 24.8 (2×), 19.1, 13.6. HRMS calcd for $C_{15}H_{27}BrO_2$ (M$^+$): 318.1195, found: 318.1192.

6.31 Butyl 1-{11-[1-(butoxycarbonyl)cyclopentyl]-6-oxoundecyl}-1-cyclopentanecarboxylate Under a $N_2$ atmosphere, NaH (60% (w/w) in mineral oil, 7.55 g, 189 mmol) was added portion wise to a solution of TosMIC (12.48 g, 62.6 mmol) and $Bu_4NI$ (2.56 g, 6.93 mmol) in dry DMSO (200 mL) while stirring vigorously and cooling with a water bath. After 30 min, butyl 1-(5-bromo-pentyl)-cyclopentanecarboxylate (44.46 g, >90% pure by GC, 125 mmol) was added drop wise to the mixture in 20 min and after 1 h of stirring, another portion of NaH (60% (w/w) in mineral oil, 1.20 g, 30.0 mmol) was added. After 1 h, the reaction mixture was slowly poured into ice-cold $H_2O$ (500 mL) and the resulting mixture was extracted with $Et_2O$ (3×250 mL). The combined organic layers were washed with aqueous NaCl (10%, 250 mL) and brine (2×200 mL), dried ($Na_2SO_4$) and filtered through a layer of silica (150 g). The residue was washed with $Et_2O$ (250 mL) and the combined filtrate and washings were evaporated in vacuo. The remaining oil was purified by column chromatography (silica, heptane:EtOAc=8:1) to give butyl 1-{11-[1-(butoxycarbonyl)cyclopentyl]-6-isocyano-6-[(4-methylphenyl)sulfonyl]undecyl}-1-cyclopentanecarboxylate as a yellow oil (32.79 g). This oil (32.79 g) was dissolved in $CH_2Cl_2$ (400 mL), and cont aqueous HCl (150 mL) was added. After stirring vigorously for 4.5 h, $H_2O$ (500 mL) was added and the layers were separated. The aqueous phase was extracted with $CH_2Cl_2$ (2×100 mL) and the combined organic layers were washed with saturated $H_2O$ (200 mL), saturated aqueous $NaHCO_3$ (500 mL) and brine (500 mL), dried ($Na_2SO_4$) and evaporated in vacuo. The remaining residue was purified by column chromatography (silica, heptane:EtOAc=6:1) to give butyl 1-{11-[1-(butoxycarbonyl)cyclopentyl]-6-oxoundecyl}-1-cyclopentanecarboxylate (24.11 g, 90% pure by $^1$H NMR, 69%) as a slightly yellow liquid. $^1$H NMR ($CDCl_3$): δ=4.06 (t, J=6.6 Hz, 4H), 2.36 (t, J=7.4 Hz, 4H), 2.15-2.06 (m, 4H), 1.65-1.52 (m, 20H), 1.49-1.32 (m, 8H), 1.27-1.19 (m, 8H), 0.94 (t, J=7.4 Hz, 6H). $^{13}$C NMR ($CDCl_3$): δ=210.9, 177.6 (2×), 63.8 (2×), 54.0 (2×), 42.5 (2×), 38.9 (2×), 35.8 (4×), 30.6 (2×), 29.5 (2×), 25.6 (2×), 24.7 (4×), 23.4 (2×), 19.0 (2×), 13.5 (2×). FIRMS calcd for $C_{31}H_{54}O_5$ (M$^+$): 506.3971, found: 506.3981.

6.32 1-[11-(1-Carboxycyclopentyl)-6-oxoundecyl]-1-cyclopentanecarboxylic acid $LiOH.H_2O$ (7.83 g, 187 mmol) and $H_2O$ (100 mL) were added to a solution of butyl 1-{11-[1-(butoxycarbonyl)cyclopentyl]-6-oxoundecyl}-1-cyclopentanecarboxylate (21.03 g, 90% pure by $^1$H NMR, 37.3 mmol) in EtOH (300 mL) and the resulting mixture was stirred at reflux temperature for 2 d, allowed to cool to rt and concentrated in vacuo to a smaller volume. $H_2O$ (100 mL) was added and the resulting mixture was extracted with $Et_2O$ (100 mL), acidified with conc aqueous HCl (25 mL) and extracted with $Et_2O$ (3×150 mL). The latter organic layers were combined, dried ($Na_2SO_4$; To avoid loss of material, a minimal amount of $Na_2SO_4$ was used, with the desiccant becoming a white, oily paste. The organic layer was decanted from the desiccant.) and evaporated in vacuo. The remaining residue was purified by recrystallization from a mixture of $iPr_2O$ and heptane to give 1-[11-(1-carboxycyclopentyl)-6-oxoundecyl]-1-cyclopentanecarboxylic acid (12.15 g, 83%) as white granules. mp=78-85° C. $^1$H NMR ($CDCl_3$): δ=2.37 (t, J=7.4 Hz, 4H), 2.18-2.10 (m, 4H), 1.65-1.45 (m, 20H), 1.29-1.25 (m, 8H). $^{13}$C NMR ($CDCl_3$): δ=211.5, 184.8 (2×), 54.0 (2×), 42.4 (2×), 38.9 (2×), 35.9 (4×), 29.2 (2×), 25.5 (2×), 24.9 (4×), 23.5 (2×). Anal. calcd for $C_{23}H_{38}O_5$: C, 70.02; H, 9.71, found: C, 70.37; H, 9.72.

6.33 1-[11-(1-Carboxycyclopentyl)-6-hydroxyundecyl]-1-cyclopentanecarboxylic acid To a mixture of 1-[11-(1-carboxycyclopentyl)-6-oxoundecyl]-1-cyclopentanecarboxylic acid (5.00 g, 12.7 mmol) in iPrOH (30 mL) and $H_2O$ (30 mL) was added NaOH (1.07 g, 26.3 mmol). To the resulting clear solution, $NaBH_4$ (0.38 g, 10.0 mmol) was added. After 19 h, the reaction mixture was concentrated in vacuo. The remaining residue was dissolved in $H_2O$ (50 mL) and acidified with aqueous HCl (6M, 15 mL). The resulting mixture was extracted with $Et_2O$ (100 mL, 2×50 mL), and the combined organic layers were washed with brine (2×50 mL), dried ($Na_2SO_4$) and concentrated in vacuo to give 1-[11-(1-carboxycyclopentyl)-6-hydroxyundecyl]-1-cyclopentanecarboxylic acid (5.18 g, 99%, contains 4% (%) $Et_2O$) as a thick, light yellow oil that slowly crystallized on standing. mp=: 76-77° C. $^1$H NMR ($CDCl_3$); δ=3.56 (br s, 1H), 2.16-2.11 (m, 4H), 1.64-1.61 (m, 12H), 1.51-1.18 (m, 20H). $^{13}$C NMR ($CDCl_3$): δ=184.3 (2×), 71.4, 54.2 (2×), 39.2 (2×), 36.9 (2×), 36.2 (2×), 35.7 (2×), 29.5 (2×), 25.9 (2×), 25.2 (2×), 25.1 (2×), 25.0 (2×).

7. BIOLOGICAL ASSAYS

7.1 Effects of Illustrative Compounds of the Invention on NonHDL Cholesterol, HDL Cholesterol, Triglyceride Levels, Glycemic Control indicators and Body Weight Control in Obese Female Zucker Rats In a number of different experiments, illustrative compounds of the invention are administered daily at a dose of up to 100 mg/kg to chow fed obese female Zucker rats for fourteen days in the morning by oral gavage in 1.5% carboxymethylcellulose/0.2% Tween 20 or 20% ethanol/80% polyethylene glycol (dosing vehicles). Animals are weighed daily.

Animals are allowed free access to rodent chow and water throughout the study except on days of blood sampling where food is restricted for six hours prior to blood sampling. Blood glucose is determined after the 6 hour fast in the afternoon without anesthesia from a tail vein. Serum is also prepared from pretreatment blood samples subsequently obtained from the orbital venous plexus (with $O_2/CO_2$ anesthesia) and following the fourteenth dose at sacrifice from the heart following $O_2/CO_2$ anesthesia. Serums are assayed for lipoprotein cholesterol profiles, triglycerides, total cholesterol, Non-HDL cholesterol, HDL cholesterol, the ratio of HDL cholesterol to that of Non-HDL cholesterol, insulin, non-esterified fatty acids, and beta-hydroxy butyric acid. The percent body weight gain and the ratio of liver to body weight is also determined. These are shown as absolute values or as a percent change of the pretreatment values in Table 1.

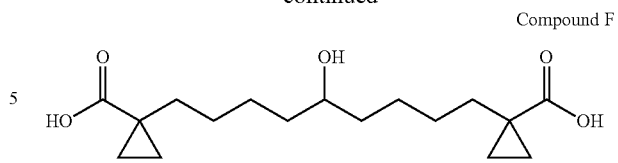

Compound F

TABLE 1

Examples of effects of oral daily treatment of obese female Zucker rats with illustrative compounds of the invention for fourteen days
Percent of Pre-treatment

| Compound | Expt. # | n | Dose (mg/kg/day) | % wt. gain | HDL-C/ non-HDL-C | TG | TC | Non-HDL-C | HDL-C | Glucose | Insulin | NEFA | BHA |
|---|---|---|---|---|---|---|---|---|---|---|---|---|---|
| Vehicle | LR132 | 4 |  | 10.50% | 4 | 3 | 5 | −8 | 10 | −2 | 42 | −3 | 78 |
| A |  | 4 | 30 | 12.3 | 4 | −23 | 37 | −20 | 76 | −1 | −8 | −30 | 150 |
| Vehicle | LR132 | 4 |  | 10.5 | 4 | 3 | 5 | −8 | 10 | −2 | 42 | −3 | 78 |
| B |  | 4 | 100 | 4.2 | 153 | −91 | 13 | −94 | 54 | −24 | −51 | −23 | 254 |
| Vehicle | LR132 | 4 |  | 10.5 | 4 | 3 | 5 | −8 | 10 | −2 | 42 | −3 | 78 |
| D |  | 4 | 100 | −1.7 | 785 | −97 | −11 | −98 | 15 | −13 | −70 | −44 | 195 |
| Vehicle | LR132 | 4 |  | 10.5 | 4 | 3 | 5 | −8 | 10 | −2 | 42 | −3 | 78 |
| E |  | 3 | 100 | 10.4 | 5 | −34 | 101 | 1 | 162 | −2 | 2 | −24 | 223 | n is number of animals per experiment

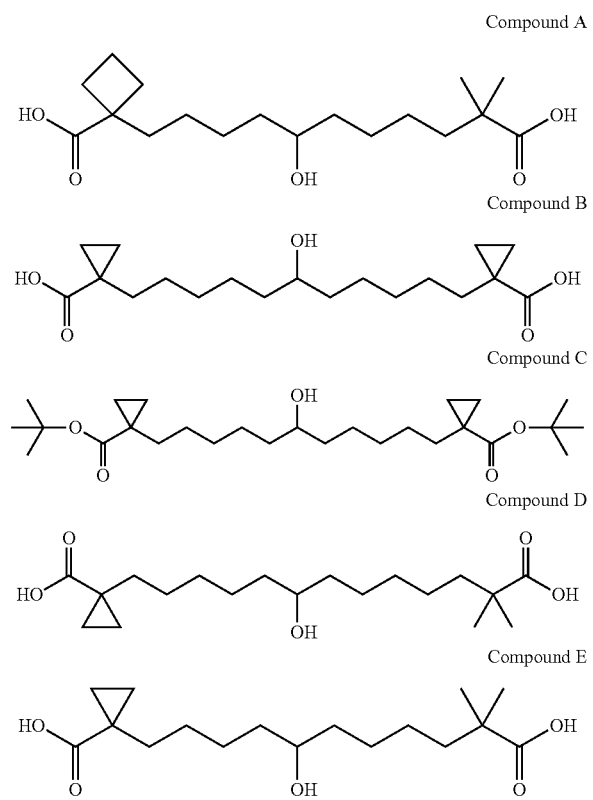

Compound A

Compound B

Compound C

Compound D

Compound E

7.2 Effects of Illustrative Compounds of the Invention on the In Vitro Lipid Synthesis in Isolated Hepatocytes Compounds were tested for inhibition of lipid synthesis in primary cultures of rat hepatocytes. Male Sprague-Dawley rats were anesthetized with intraperitoneal injection of sodium pentobarbital (80 mg/kg). Rat hepatocytes were isolated essentially as described by the method of Seglen (Seglen, P. O. Hepatocyte suspensions and cultures as tools in experimental carcinogenesis. *J. Toxicol. Environ. Health* 1979, 5, 551-560). Hepatocytes were suspended in Dulbecco's Modified Eagles Medium containing 25 mM D-glucose, 14 mM HEPES, 5 mM L-glutamine, 5 mM leucine, 5 mM alanine, 10 mM lactate, 1 mM pyruvate, 0.2% bovine serum albumin, 17.4 mM non-essential amino acids, 20% fetal bovine serum, 100 nM insulin and 20 µg/mL gentamycin) and plated at a density of $1.5 \times 10^5$ cells/cm² on collagen-coated 96-well plates. Four hours after plating, media was replaced with the same media without serum. Cells were grown overnight to allow formation of monolayer cultures. Lipid synthesis incubation conditions were initially assessed to ensure the linearity of [1-$^{14}$C]-acetate incorporation into hepatocyte lipids for up to 4 hours. Hepatocyte lipid synthesis inhibitory activity was assessed during incubations in the presence of 0.25 µCi [1-$^{14}$C]-acetate/well (final radiospecific activity in assay is 1 Ci/mol) and 0, 1, 3, 10, 30, 100 or 300 µM of compounds for 4 hours. At the end of the 4-hour incubation period, medium was discarded and cells were washed twice with ice-cold phosphate buffered saline and stored frozen prior to analysis. To determine total lipid synthesis, 170 µl of MicroScint-E® and 50 µl water was added to each well to extract and partition the lipid soluble products to the upper organic phase containing the scintillant. Lipid radioactivity was assessed by scintillation spectroscopy in a Packard TopCount NXT. Lipid synthesis rates were used to determine the $IC_{50}$s of the compounds that are presented in Table 2.

TABLE 2

Effect of Illustrative Compounds A, B, and D-F on Lipid Synthesis in Primary Rat Hepatocytes.

| Compound | $IC_{50}$ (μM) | 95% Confidence Interval Lower | 95% Confidence Interval Upper | $r^2$ |
|---|---|---|---|---|
| A | 12.0 | 5.4 | 26.3 | 0.98 |
| B | 0.9 | 0.8 | 1.1 | 0.99 |
| D | 1.4 | 1.2 | 1.6 | 0.99 |
| E | 3.0 | 2.6 | 3.4 | 0.98 |
| F | 1.8 | 1.4 | 2.3 | 0.96 |

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

What is claimed:

1. A method for treating or preventing diabetes, diabetic nephropathy, diabetic retinopathy, a disorder of glucose metabolism, or obesity in a patient in need of such treatment or prevention, comprising administering to the patient a therapeutically or prophylactically effective amount of a compound of formula I:

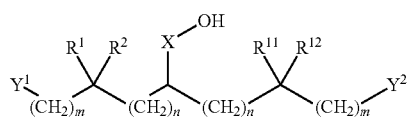

or a pharmaceutically acceptable salt, hydrate, solvate or a mixture thereof, wherein:
(a) each occurrence of m is independently an integer ranging from 0 to 5;
(b) each occurrence of n is independently an integer ranging from 3 to 7;
(c) X is $(CH_2)_z$ or Ph; wherein z is an integer from 0 to 4;
(d) each occurrence of $R^1$ and $R^2$ is independently $(C_1-C_6)$ alkyl, $(C_2-C_6)$alkenyl, $(C_2-C_6)$alkynyl, phenyl, benzyl, or $R^1$ and $R^2$ and the carbon to which they are both attached are taken together to form a $(C_3-C_7)$cycloakyl group;
(e) each occurrence of $R^{11}$ and $R^{12}$ and the carbon to which they are both attached are taken together to form a $(C_3-C_7)$cycloakyl group;
(f) each occurrence of $Y^1$ and $Y^2$ is independently $(C_1-C_6)$ alkyl, OH, COOH, $COOR^3$, $SO_3H$,

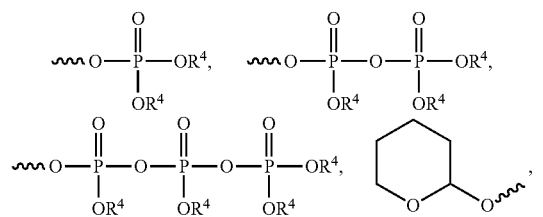

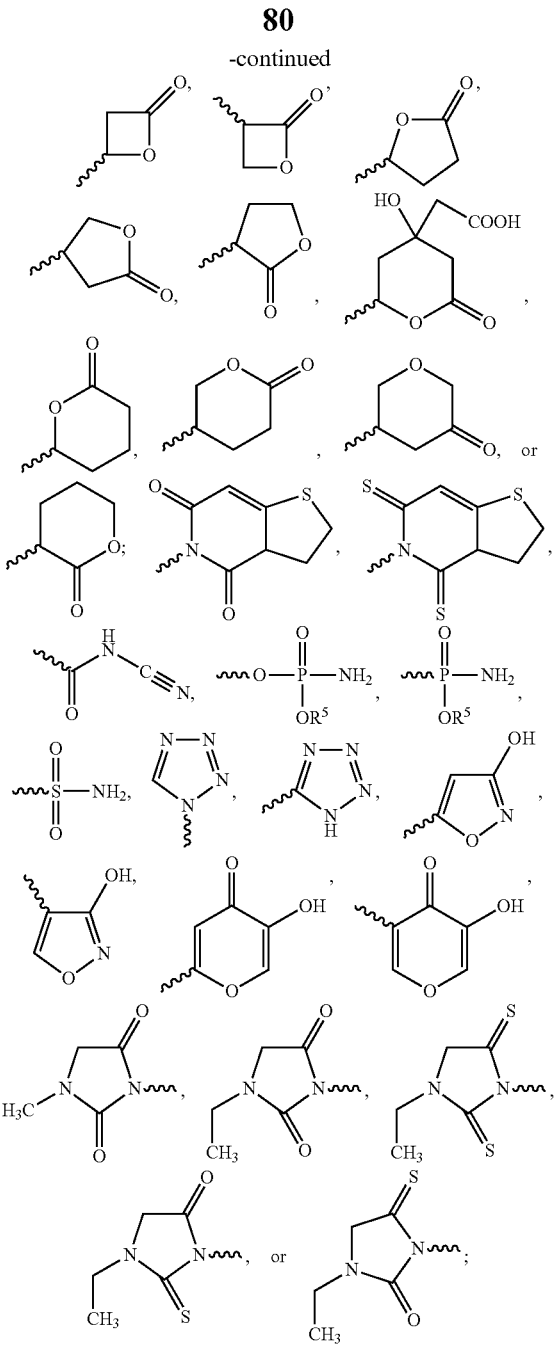

wherein:
(i) $R^3$ is $(C_1-C_6)$alkyl, $(C_2-C_6)$alkenyl, $(C_2-C_6)$alkynyl, phenyl, or benzyl and is unsubstituted or substituted with one or more halo, OH, $(C_1-C_6)$alkoxy, or phenyl groups,
(ii) each occurrence of $R^4$ is independently H, $(C_1-C_6)$ alkyl, $(C_2-C_6)$alkenyl, or $(C_2-C_6)$alkynyl and is unsubstituted or substituted with one or two halo, OH, $C_1-C_6$ alkoxy, or phenyl groups; and
(iii) each occurrence of $R^5$ is independently H, $(C_1-C_6)$ alkyl, $(C_2-C_6)$alkenyl, or $(C_2-C_6)$alkynyl.

2. The method compound of claim 1, wherein each occurrence of $Y^1$ and $Y^2$ is independently OH, $COOR^3$, or COOH.

3. The method of claim 1, wherein m is 0.

4. The method of claim 1, wherein m is 1.

5. The method of claim 1, wherein n is 4.

6. The method of claim 1, wherein n is 5.
7. The method of claim 1, wherein X is $(CH_2)_z$ and z is 0.
8. The method of claim 1, wherein each occurrence of $R^1$ and $R^2$ and the carbon to which they are both attached are taken together to form a $(C_3$-$C_7)$cycloakyl group.
9. The method of claim 1, wherein the compound of formula I is selected from the group consisting of
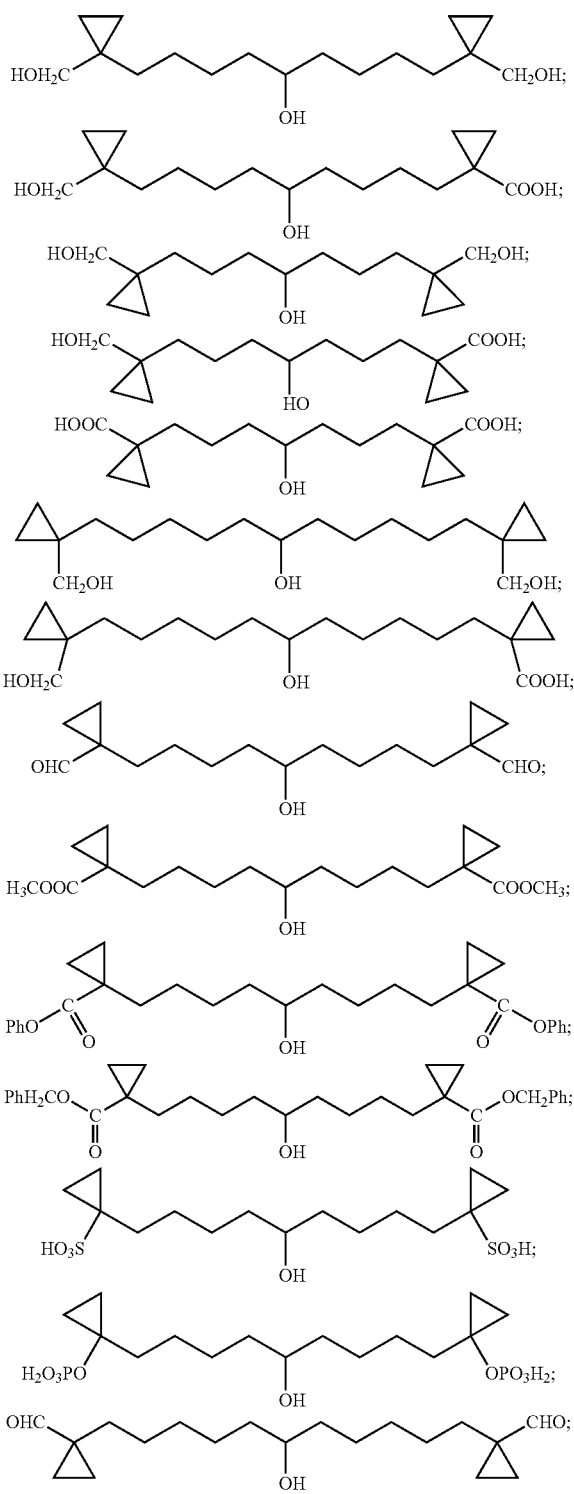
-continued
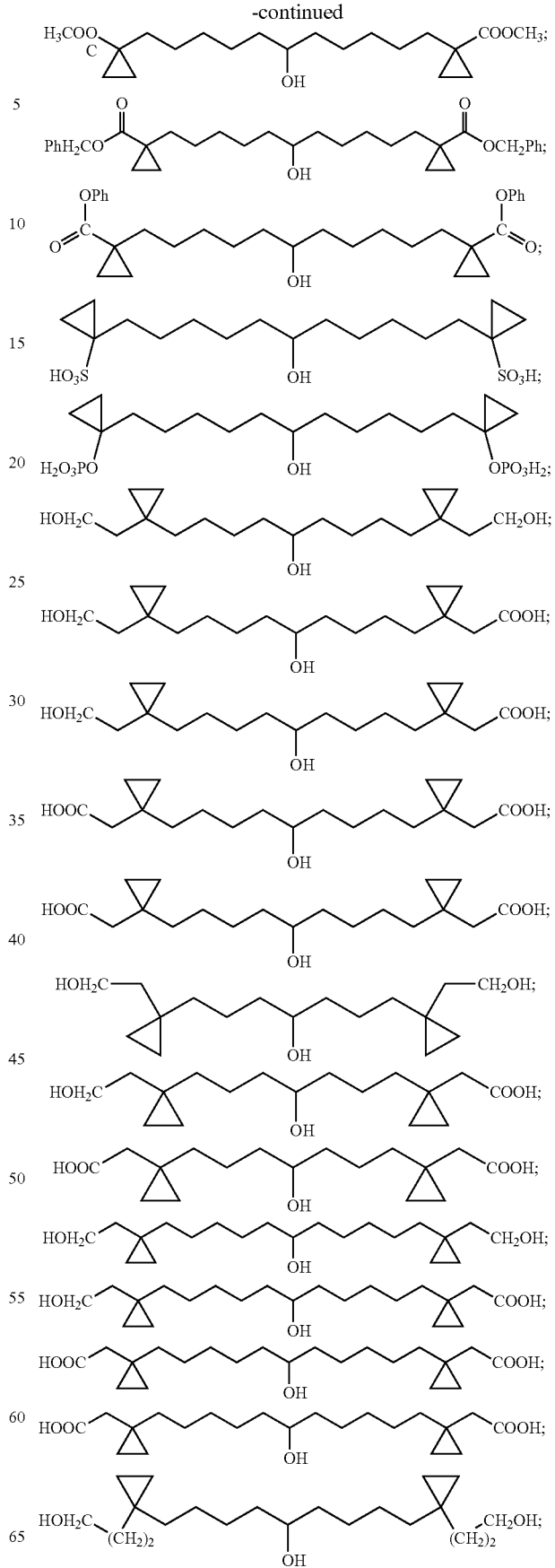

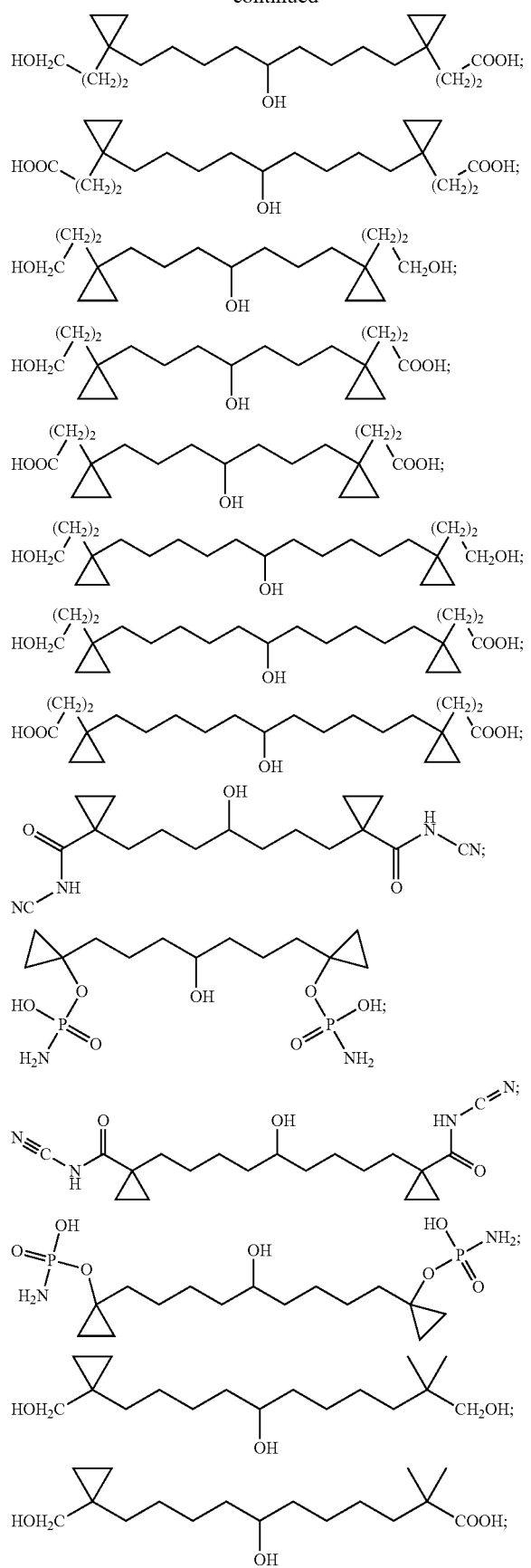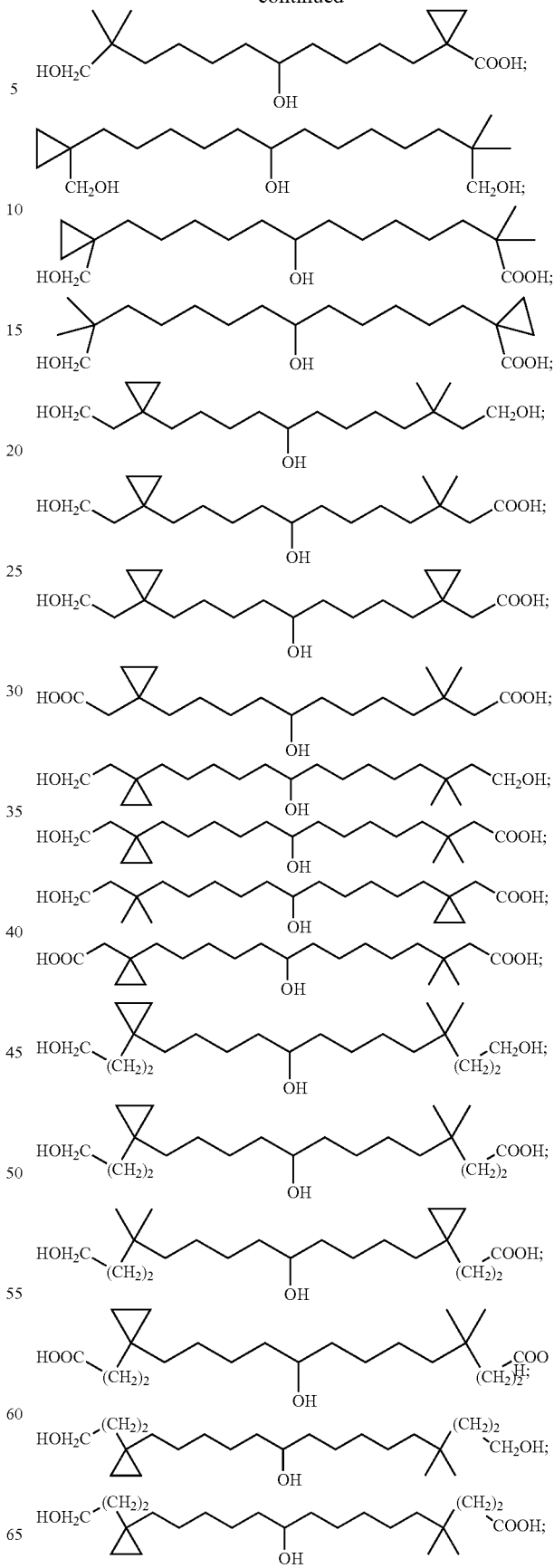

-continued

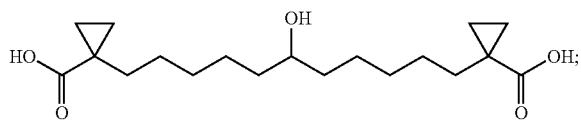

or a pharmaceutically acceptable salt thereof.

10. The method of claim 1, wherein the compound of formula I is

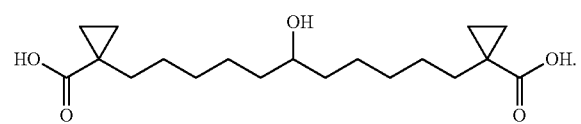

or a pharmaceutically acceptable salt thereof.

11. The method of claim 1, wherein the compound of formula I is

12. The method of claim 1, wherein the compound of formula I is

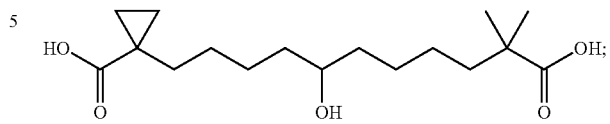

or a pharmaceutically acceptable salt thereof.

13. The method of claim 1, wherein the compound of formula I is

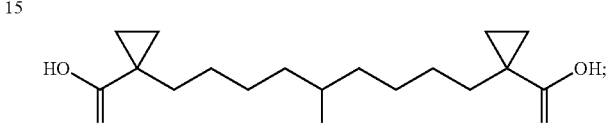

or a pharmaceutically acceptable salt thereof.

14. The method of claim 1, wherein the compound of formula I is

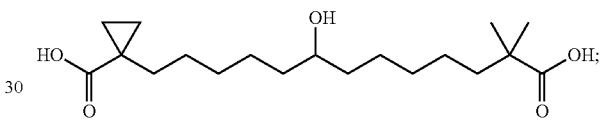

or a pharmaceutically acceptable salt thereof.

15. The method of claim 1, wherein the method comprises treating or preventing diabetes.

16. The method of claim 15, wherein the diabetes is selected from the group consisting non-insulin dependent diabetes mellitus, insulin dependent diabetes mellitus, gestational diabetes mellitus, and maturity onset diabetes of the young.

17. The method of claim 1, wherein the method comprises treating or preventing diabetic nephropathy or diabetic retinopathy.

18. The method of claim 1, wherein the method comprises treating or preventing a disorder of glucose metabolism.

19. The method of claim 18, wherein the disorder of glucose metabolism is selected from the group consisting of impaired glucose tolerance, insulin resistance, high levels of blood insulin, and high levels of blood glucose.

20. The method of claim 1, wherein the method comprises treating or preventing obesity.

* * * * *